US009721046B2

(12) United States Patent
Khainson et al.

(10) Patent No.: US 9,721,046 B2
(45) Date of Patent: Aug. 1, 2017

(54) SYSTEM AND METHOD FOR REALIZING A BUILDING SYSTEM THAT INVOLVES COMPUTER BASED MATCHING OF FORM TO FUNCTION

(71) Applicant: Aditazz, Inc., San Bruno, CA (US)

(72) Inventors: Alexander Khainson, San Carlos, CA (US); Zachary Deretsky, San Carlos, CA (US); Deepak Aatresh, Saratoga, CA (US); Ward A. Vercruysse, Portolla Valley, CA (US); Richard L. Sarao, San Francisco, CA (US); Sudha Hajela, Brisbane, CA (US)

(73) Assignee: ADITAZZ, INC., Brisbane, CA (US)

( * ) Notice: Subject to any disclaimer, the term of this patent is extended or adjusted under 35 U.S.C. 154(b) by 716 days.

(21) Appl. No.: 14/216,258

(22) Filed: Mar. 17, 2014

(65) Prior Publication Data

US 2014/0288890 A1 Sep. 25, 2014

Related U.S. Application Data

(63) Continuation-in-part of application No. 13/833,386, filed on Mar. 15, 2013.
(Continued)

(51) Int. Cl.
*G06F 17/50* (2006.01)
*G06Q 50/22* (2012.01)

(52) U.S. Cl.
CPC ......... *G06F 17/5004* (2013.01); *G06Q 50/22* (2013.01)

(58) Field of Classification Search
CPC .............. G06F 17/5004; H02J 3/14
See application file for complete search history.

(56) References Cited

U.S. PATENT DOCUMENTS 7,529,650 B2 5/2009 Wakelam et al.
2006/0282302 A1 12/2006 Hussain
(Continued)

OTHER PUBLICATIONS

Palonen, M. et al.; "A Genetic Algorithm for Optimization of Building Envelope and HVAC System Parameters"; Eleventh International IBPSA Conference, Glasgow, Scotland; pp. 159-166; Jul. 27-30, 2009.
Manthilake, M.M. Inoka Damayanthi; "Evolutionary building layout optimization"; Doctoral Thesis; Dept. of Civil and Building Engineering, Loughborough University; Mar. 2011.
(Continued)

*Primary Examiner* — Kandasamy Thangavelu

(57) ABSTRACT

Systems and methods for realizing a complex building system are disclosed. The systems and methods utilize computer-based techniques to rapidly explore large numbers of pattern matching scenarios on a scale which heretofore has not been attempted. In an embodiment, the computer-based technique performs large-scale pattern matching operations to find the best match between functional patterns and spatial patterns. For example, with reference to a particular building system, the technique involves operational modeling to identify the types and volumes of services to provide (functional patterns) and to characterize the physical relationships between the services (e.g., adjacency preferences), along with establishing libraries of three dimensional spaces (spatial patterns), in the form of room and department libraries and building massing configuration libraries. Large numbers of functional patterns and spatial patterns are then matched to each other using cost-based algorithms to find the best match or matches between the form and function.

31 Claims, 60 Drawing Sheets

Related U.S. Application Data

(60) Provisional application No. 61/799,554, filed on Mar. 15, 2013.

(56) References Cited

U.S. PATENT DOCUMENTS

| | | | | |
|---|---|---|---|---|
| 2010/0324956 | A1* | 12/2010 | Lopez | G06F 17/5004 705/7.37 |
| 2011/0166710 | A1* | 7/2011 | Kordik | H02J 3/14 700/277 |
| 2012/0065945 | A1 | 3/2012 | Brown et al. | |
| 2012/0239353 | A1* | 9/2012 | Vercruysse | G06F 17/5004 703/1 |
| 2012/0296611 | A1 | 11/2012 | Teller et al. | |
| 2014/0025347 | A1* | 1/2014 | Kim | G06F 17/5004 703/1 |
| 2014/0052416 | A1* | 2/2014 | Yu | G06F 17/5004 703/1 |

OTHER PUBLICATIONS

Bitterman, Michael S. et al.; "An Adaptive Multi-Objective Evolutionary Algorithm with Human-like Reasoning for Enhanced Decision-Making in Building Design"; IEEE, 8 pgs.; 2011.

Caldas, L.G. et al.; "Genetic Algorithms for Optimization of Building Envelopes and the Design and Control of HVAC Systems"; Journal of Solar Energy Engineering, vol. 125; pp. 343-351; Aug. 2003.

Oh, Se-Min et al.; "Process-Driven BIM-based optimal design using integration of energyplus, genetic algorithm, and Pareto Optimality"; Proceedings of Building Simulation 2011; 12th Conference of International Building Performanc Simulation Association, Sydney, Nov. 14-16; pp. 894-901; 2011.

Jo, Jun H. et al.; "Space Layout Planning using an Evolutionary Approach"; Artificial Intelligence in Engineering, vol. 12, Issue 3; pp. 149-1621 Jul. 1998.

International Search Report, PCT/US2014/030386, Aug. 13, 2014.

* cited by examiner

| FIG. 40B | FIG. 40C | FIG. 40D | FIG. 40E |
|---|---|---|---|
| FIG. 40F | FIG. 40G | FIG. 40H | FIG. 40I |

KEY — FIG. 40A

FIG. 40

KEY

| | OCCUPANCY TYPE | | ADJACENCY TYPE |
|---|---|---|---|
| A | ASSEMBLY | A | STRONG CONNECTION: ADJACENT/ABUTMENT |
| B | B-OCCUPANCY | B | STRONG CONNECTION: DIFFERENT FLOOR ACCEPTABLE/STACKED |
| F | FACTORY | C | CLOSE: SAME FLOOR REQUIRED |
| H | HAZARDOUS | D | CLOSE: DIFFERENT FLOOR ACCEPTABLE |
| I-2 | I-2 OCCUPANCY | E | SEPARATION: REQUIRED - NON-ADJACENT, SAME FLOOR ACCEPTABLE |
| S | STORAGE | F | SEPARATION: PREFERRED |
| | | G | INDIFFERENT |
| | | | SHELL/ FUTURE EXPANSION |
| | | H | SHELL SPACE REQUIRED: PLACE ADJACENT TO DEPARTMENT |
| | | X | FUTURE EXPANSION REQUIRED: PROVIDE PERIMETER FOR FUTURE GROWTH |

| | REASONS FOR ADJACENCY TYPE* |
|---|---|
| 1 | WORKFLOW SEQUENCE |
| 2 | URGENCY OF ACCESS |
| 3 | FREQUENCY OF USE |
| 4 | PATIENT CONVENIENCE |
| 5 | STAFF CONVENIENCE |
| 6 | NEED FOR SECURITY |
| 7 | ACCESSIBILITY OF SUPPLIES |
| 8 | NOISE OR VIBRATION |
| 9 | FUMES OR ODORS |
| 10 | CONTAMINATION RISK |
| 11 | OTHER |

* THESE MAY BE ADDED TO THE MATRIX IF NECESSARY

| | CONNECTIVITY / CIRCULATION TYPE | | ACCESS TYPE |
|---|---|---|---|
| h | HORIZONTAL - WALKING, GURNEY - TYP. | P | PATIENT** |
| v | VERTICAL - ELEVATOR CONNECTION ACCEPTABLE | V | VISITOR / PUBLIC** |
| p | PNEUMATIC TUBE REQUIRED | S | SERVICE / STAFF ONLY |
| r | ROBOTS - OPTIONAL | | |
| | NATURAL LIGHT REQUIREMENT | | |
| w | WINDOW REQUIRED - IMPLIES EXTERIOR WALL ABUTMENT | | |
| y | WINDOW PREFERRED - BORROWED LIGHT ACCEPTABLE | | |
| z | NOT REQUIRED | | |

** IMPLIES STAFF ALSO

FIG. 40A

| | | OCCUPANCY TYPE | PREFERRED BUILDING IF MULTIPLE BUILDINGS PLANNED | PREFERRED FLOOR LEVEL | NATURAL LIGHT REQUIREMENT | DEPARTMENT ACCESS | SHELL / FUTURE EXPANSION | |
|---|---|---|---|---|---|---|---|---|
| INPATIENT CARE BEDS | | | | | | | | |
| | 1 | ACUTE CARE | I | BED | >L1 | w | P | X |
| | 2 | CRITICAL CARE | I | BED | >L1 | w | P | |
| | 3 | INPATIENT REHAB | I | BED | | y | P | |
| | 4 | MEDITATION ROOM | B | | L1 | y | V | |
| | 5 | PROVIDER CALL ROOMS | | BED | | y | S | |
| BIRTHING CENTER BEDS | | | | | | | | |
| | 6 | LDRPs | I | D&T | >L1 | w | P | |
| | 7 | ANTE- & POST-PARTUM BEDS | I | BED | >L1 | w | P | |
| | 8 | NEWBORN NURSERY | I | BED | >L1 | w | P | |
| DIAGNOSTIC ZONE | | | | | | | | |
| | 9 | CLINICAL LAB/PATHOLOGY | | D&T | <L2 | w | S | H |
| | 10 | EMERGENCY | I | D&T | L1 | w | P | X |
| | 11 | ED OVERFLOW/OBSERVATION | I | D&T | L1 | w | P | X |
| | 12 | IMAGING | I | D&T | L1 | y | P | X |
| | 13 | MULTI-TESTING | | D&T | L1 | y | P | |
| | 14 | PATIENT ACCESS/ADMITTING | | D&T | L1 | y | P | |
| PROCEDURAL SERVICES | | | | | | | | |
| | 15 | IR/CATH (SHELL SPACE) | I | D&T | L1 OR L2 | z | P | H |
| | 16 | SURGICAL SERVICES | I | D&T | L1 OR L2 | y | P | X |
| | 17 | PRE- & POST- OP (INCL. PACU) | I | D&T | L1 OR L2 | y | P | X |
| ADMINISTRATIVE SERVICES | | | | | | | | |
| | 18 | CONFERENCE ROOMS | B | D&T | TOP | y | S | |
| | 19 | HEALTH INFORMATION MANAGEMENT (HIM) | B | D&T | TOP | y | S | |
| | 20 | HOSPITAL BASED PHYSICIANS | B | D&T | TOP | y | S | |
| | 21 | MANAGEMENT OFFICES | B | D&T | TOP | w | S | |
| | 22 | VOLUNTEERS | B | | <L2 | y | S | |

| | | | | | | | |
|---|---|---|---|---|---|---|---|
| SUPPORT SERVICES | | | | | | | |
| 23 | BIOMEDICAL ENGINEERING | D&T | L0 | z | S | | |
| 24 | BUILDING SERVICES | D&T | L0 | z | S | | |
| 25 | DIETARY SERVICES | | L1 | w | V, S | | |
| 26 | ENVIRONMENTAL SERVICES | D&T | L0 | z | S | | |
| 27 | IT & TELECOM | D&T | L0 | z | S | | |
| 28 | MATERIALS MANAGEMENT | D&T | L0 | z | S | | |
| 29 | PATIENT LIFT TEAMS | | <L2 | y | S | | |
| 30 | PATIENT TRANSPORT | | <L2 | y | S | | |
| 31 | PHARMACY | D&T | | y | S | H | |
| 32 | SECURITY | | <L2 | y | S | | |
| 33 | STAFF LOCKERS & LOUNGE | | L0 | y | S | | |
| 34 | STERILE PROCESSING DEPT. (SPD) | D&T | | z | S | | |
| 35 | MECH/ELECT | | L0 | z | S | | |
| OTHER FUNCTIONS | | | | | | | |
| 36 | LOBBY | D&T | L1 | w | V | | |
| 37 | MAIN ENTRY | D&T | L1 | | V | | |
| 38 | AMBULANCE ENTRY | D&T | L1 | | P | | |
| 39 | ED WALK-IN | D&T | L1 | | P | | |
| 40 | LOADING DOCK | D&T | L0 | | S | | |
| 41 | PUBLIC TOILETS | D&T | ALL | z | V | | |
| 42 | MOB | | | | V | | |
| CIRCULATION | | | | | | | |
| 43 | ELEVATOR - VISITOR | | | | V | | |
| 44 | ELEVATOR - PATIENT | | | | P | | |
| 45 | ELEVATOR - SERVICE | | | | S | | |

FIG. 40F

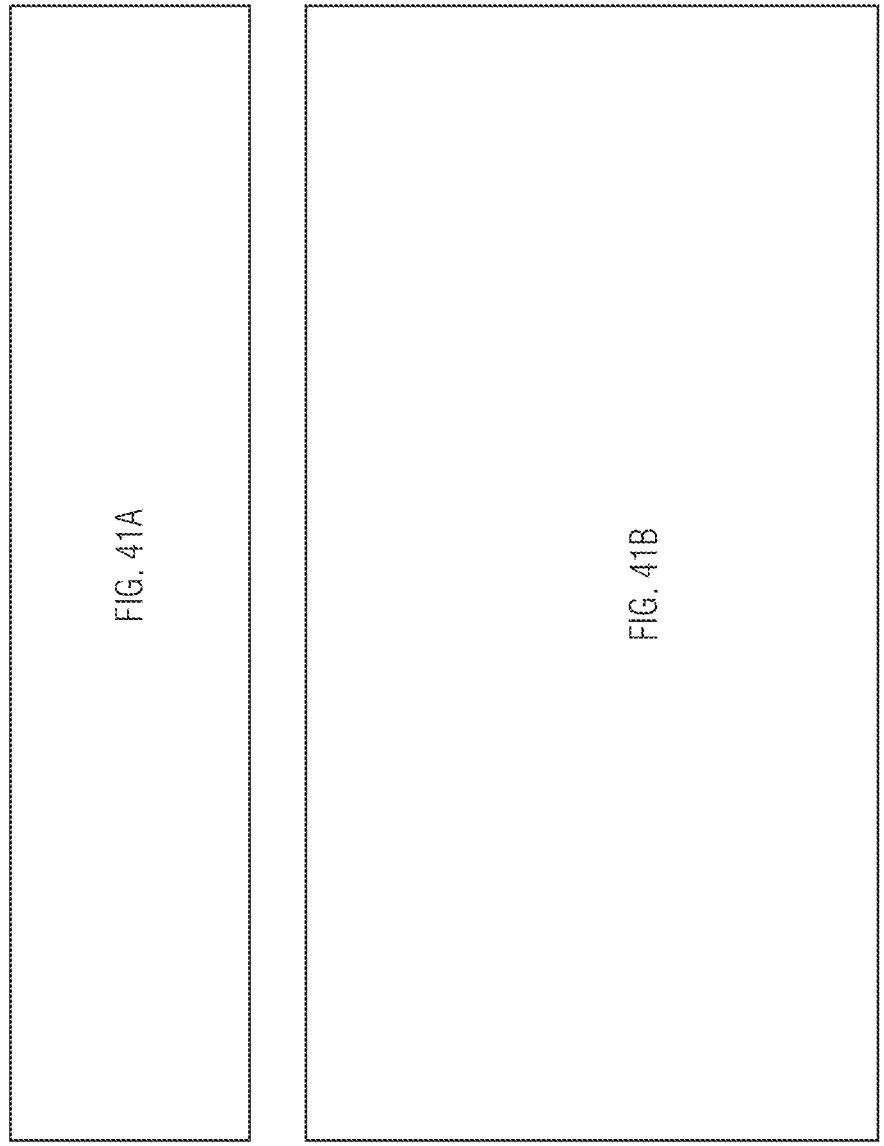

| KEY | | |
|---|---|---|
| | OCCUPANCY TYPE | ADJACENCY TYPE |
| A | ASSEMBLY | A STRONG CONNECTION: ADJACENT/ABUTMENT |
| B | B-OCCUPANCY | B STRONG CONNECTION: DIFFERENT FLOOR ACCEPTABLE/STACKED |
| F | FACTORY | C CLOSE: SAME FLOOR REQUIRED |
| H | HAZARDOUS | D CLOSE: DIFFERENT FLOOR ACCEPTABLE |
| I-2 | I-2 OCCUPANCY | E SEPARATION: REQUIRED - NON-ADJACENT, SAME FLOOR ACCEPTABLE |
| S | STORAGE | F SEPARATION: PREFERRED |
| | | G INDIFFERENT |
| | | SHELL/FUTURE EXPANSION |
| | | H SHELL SPACE REQUIRED: PLACE ADJACENT TO DEPARTMENT |
| | | X FUTURE EXPANSION REQUIRED: PROVIDE PERIMETER FOR FUTURE GROWTH |

| | REASONS FOR ADJACENCY TYPE* |
|---|---|
| 1 | WORKFLOW SEQUENCE |
| 2 | URGENCY OF ACCESS |
| 3 | FREQUENCY OF USE |
| 4 | PATIENT CONVENIENCE |
| 5 | STAFF CONVENIENCE |
| 6 | NEED FOR SECURITY |
| 7 | ACCESSIBILITY OF SUPPLIES |
| 8 | NOISE OR VIBRATION |
| 9 | FUMES OR ODORS |
| 10 | CONTAMINATION RISK |
| 11 | OTHER |

* THESE MAY BE ADDED TO THE MATRIX IF NECESSARY

FIG. 41A

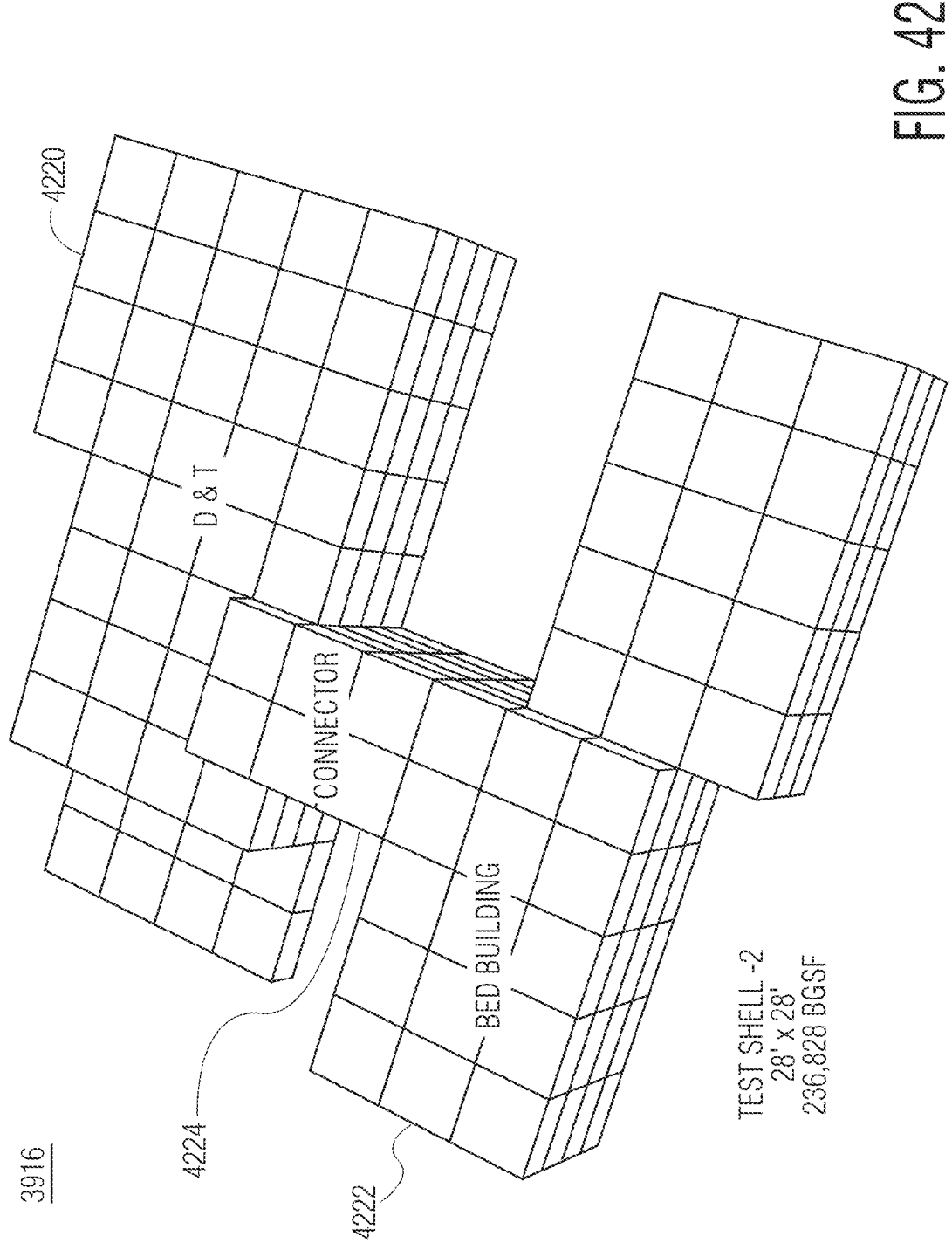

REPORT OUTPUT

BUILDING bldg_bed_i0

| STOREY | OVERALL BGSF | EXT WALL AREA | CORRIDORS AREA | DESIGNED DNSF | DESIGNED DGSF | UTILIZATION | AVAILABLE AREA |
|---|---|---|---|---|---|---|---|
| 4 | 11760 | 448 | 0 | 6670 | 9766 | 84% | 1546 |
| 3 | 23520 | 784 | 0 | 13340 | 19636 | 84% | 3102 |
| 2 | 23520 | 784 | 0 | 7220 | 21840 | 93% | 897 |
| 1 | 23520 | 784 | 0 | 23073 | 22226 | 95% | 512 |
| 0 | 3136 | 224 | 0 | 872 | 1119 | 36% | 1794 |
| TOTAL | 85456 | 3024 | 0 | 51175 | 74664 | 88% | 7849 |

BUILDING bldg_dnl_i1

| STOREY | OVERALL BGSF | EXT WALL AREA | CORRIDORS AREA | DESIGNED DNSF | DESIGNED DGSF | UTILIZATION | AVAILABLE AREA |
|---|---|---|---|---|---|---|---|
| 4 | 1568 | 168 | 0 | 0 | 0 | 0% | 1400 |
| 3 | 28224 | 728 | 0 | 6221 | 22156 | 79% | 5342 |
| 2 | 28224 | 728 | 0 | 12221 | 21560 | 77% | 5936 |
| 1 | 28224 | 728 | 0 | 13746 | 25253 | 90% | 2244 |
| 0 | 34496 | 840 | 0 | 10938 | 24598 | 72% | 9059 |
| TOTAL | 120736 | 3192 | 0 | 43124 | 93565 | 78% | 23980 |

BUILDING bldg_com_i2

| STOREY | OVERALL BGSF | EXT WALL AREA | CORRIDORS AREA | DESIGNED DNSF | DESIGNED DGSF | UTILIZATION | AVAILABLE AREA |
|---|---|---|---|---|---|---|---|
| 4 | 3136 | 224 | 0 | 0 | 0 | 0% | 2912 |
| 3 | 3136 | 224 | 0 | 0 | 0 | 0% | 2912 |
| 2 | 3136 | 224 | 0 | 0 | 0 | 0% | 2912 |
| 1 | 3136 | 224 | 0 | 410 | 792 | 26% | 2121 |
| 0 | 3136 | 224 | 0 | 0 | 0 | 0% | 2912 |
| TOTAL | 15680 | 1120 | 0 | 410 | 792 | 0% | 13769 |

FIG. 47

SYSTEM AND METHOD FOR REALIZING A BUILDING SYSTEM THAT INVOLVES COMPUTER BASED MATCHING OF FORM TO FUNCTION

CROSS-REFERENCE TO RELATED APPLICATION

This application is entitled to the benefit of provisional U.S. Patent Application Ser. No. 61/799,554, filed Mar. 15, 2013, entitled "System and method for realizing a building," which is incorporated by reference herein. This application is a continuation-in-part of U.S. patent application Ser. No. 13/833,386, filed Mar. 15, 2013.

FIELD OF THE INVENTION

The invention relates generally to buildings, and, more specifically to computer-based techniques for evaluating realizing a building system.

BACKGROUND

Buildings are an integral part of our everyday lives. The process of planning, designing and constructing these buildings has evolved over several thousands of years. Today, especially for modern facilities that are places from which to deliver complex services (like healthcare facilities), the steps followed to physically realize such buildings are very complicated and require a high degree of skilled labor that spans several different disciplines.

This complexity poses a huge challenge in terms of time, money and other resources expended in order to build a viable facility that can be used to deliver the intended services in an efficient and profitable way. Several industries and services have met similar complexity challenges by changing their work flow and adapting it to better exploit fast growing and inexpensive computational resources. This has resulted in an increased productivity in those industries.

However, the emergence of technological and computational capabilities has found limited adoption in the well established processes of building design and construction. As a result, there has been little gain in overall productivity, which is desperately needed today to meet the growing demand in complexity. For example, it has been found that while all other non-farming industries have doubled their productivity from 1964 to 2004, the building industry brethren have actually fallen behind.

While a plethora of reasons exist as to why construction productivity has not kept up with other areas, it is possible that conventional methods used in the building design and construction industry are not amenable to applying technology in general and computational technology in particular. Almost all other industries have gained in productivity due to the smart adaptation of computing technology, but, for reasons not immediately apparent, the construction industry has not seen any similar gains.

Buildings come in all different shapes and sizes and the complexity of buildings varies depending on their use. For example, from many different perspectives, a healthcare building such as a hospital is much more complex than an empty warehouse building. The complexity of a building becomes apparent when one tries to mathematically describe, model, simulate, optimize, and verify a building design such as the design of a hospital. In particular, the mathematical description, modeling, simulation, optimization, and verification are each a complex combination of three dimensional (3D) space and temporal operations. Characteristics of the 3D space include, for example, specifics of the building shell and core, the size and layout and function of the rooms, and routing of the building infrastructure. Characteristics of the temporal operations include, for example, the services provided within the building, load on the building (e.g., volume of patients), and dynamic environmental conditions (e.g., internal/external temperature, light, energy cost, etc).

Additionally, a fundamental challenge in complex building design is one of pattern matching. In particular, a fundamental challenge in designing a successful building is to match the expected temporal operations (e.g. human movement/workflow patterns) to the possible three-dimensional spaces (e.g., the physical space patterns). That is, the task of building design is a task of pattern matching in which patterns of function are matched to patterns of form.

In a healthcare facility, there are many complex functions (functional patterns) being performed simultaneously. For example, such functions include administration, admitting, diagnostic, imaging, acute care, observation, rehabilitation, surgery, laboratory, emergency, pharmacy, neonatal, delivery, information technology, sanitation, facilities, cafeteria, kitchen, etc. Each of the functions involves temporal operations that are performed within a particular physical three-dimensional space (spatial pattern) within the healthcare facility. In conventional building design processes, the three-dimensional spaces that are used to support the functions are selected by humans in a manual process from design templates that have been developed over time and have proven to be effective in supporting a particular function.

Because healthcare facilities can provide many complex functions (functional patterns), with each functional pattern utilizing a unique three-dimensional space (space pattern), the task of pattern matching can quickly become a very complex matching problem. Traditional manual building design techniques typically evaluate only a very small number of the total possible pattern matches.

SUMMARY

In accordance with an embodiment of the invention, systems and methods for realizing a complex building system are disclosed. The systems and methods utilize computer-based techniques to rapidly explore large numbers of pattern matching scenarios on a scale which heretofore has not been attempted. In an embodiment, the computer-based technique performs large-scale pattern matching operations to find the best fit between functional patterns and spatial patterns. For example, with reference to a particular building system, the technique involves operational modeling to identify the types and volumes of services to provide (functional patterns) and to characterize the physical relationships between the services (e.g., adjacency preferences), along with establishing libraries of three dimensional spaces (spatial patterns), in the form of room and department libraries and building massing configuration libraries. Large numbers of functional patterns and spatial patterns are then matched to each other using cost-based algorithms to find the best match or matches between the form and function. The best matches between the form and the function correspond to a building design in which many of the functional and spatial aspects of the building system are defined. In a further embodiment, once defined, the spatial arrangement of a particular building can be used to perform additional operational modeling to see how the proposed spatial arrangement supports the desired types and volumes of services to be delivered in the building system. For example, the actual dimensions determined by the spatial arrangement are used to operationally model the types and volumes of service that were identified in the business model domain. In an embodiment, actual dimensions include dimensions between department blocks as defined by the spatial arrangement. Using actual spatial dimensions in the operational modeling enables the building designer to evaluate how a physically realized building will perform. Operationally modeling with actual spatial dimensions also allows for further design iterations that can adjust the functional patterns and/or the spatial patterns early on in the building design process.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

FIG. 5 depicts an embodiment of a user interface from the business model domain of the building realization platform.

FIG. 7 depicts an embodiment of a user interface from the form and shell tab in the spatial arrangement domain of the building realization platform.

FIGS. 26-28 depict graphical user interfaces related to a technique for characterizing the energy use of multiple different building massing configurations using the massing configuration evaluator of FIG. 25.

FIG. 31 depicts a graphical user interface of entries in a building alphabet database that is generated using the shape grammar as described with reference to FIG. 29.

FIG. 32 depicts a graphical user interface of a search window that allows certain parameters of a search to be specified.

FIG. 35 depicts a graphical user interface of different building massing configurations that are formed by a combination of the building letters.

FIG. 40 is a key for FIGS. 40A-40I.

Figure 40D:
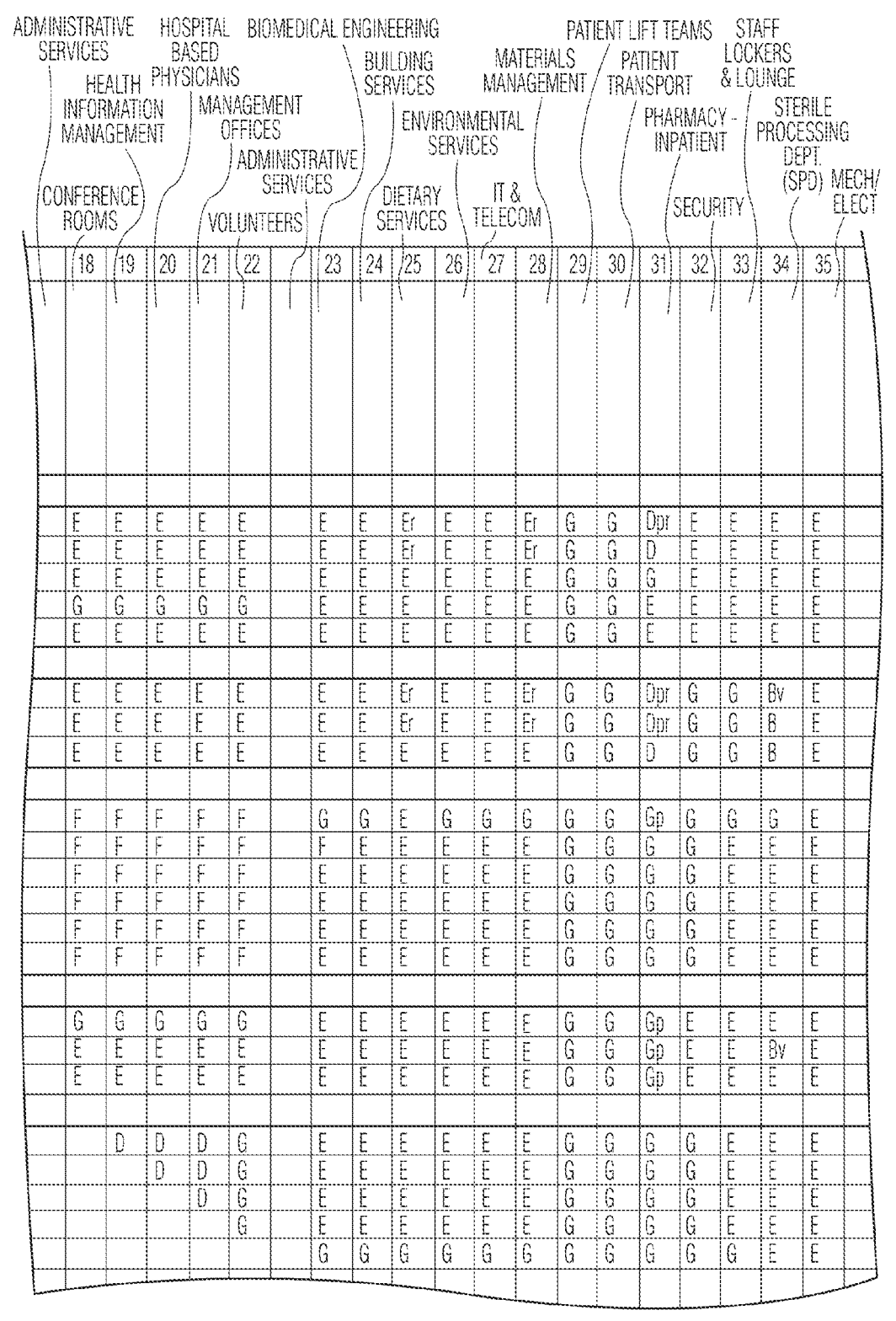

FIGS. 40A-40I depict an adjacency matrix that identifies the adjacency type between pairs of department blocks.

FIG. 41 is a key for FIGS. 41A-41B.

FIGS. 41A-41B are an expanded view of a portion of the adjacency matrix of FIG. 40.

FIG. 42 depicts an expanded view of the building massing configuration of FIG. 39.

FIG. 47 depicts a report that identifies certain characteristics of the block and stack arrangement of FIG. 44 within the building massing configuration of FIG. 42.

Throughout the description, similar reference numbers may be used to identify similar elements. Additionally, in some cases, reference numbers are not repeated in each figure in order to preserve the clarity and avoid cluttering of the figures.

DETAILED DESCRIPTION

Figure 1:
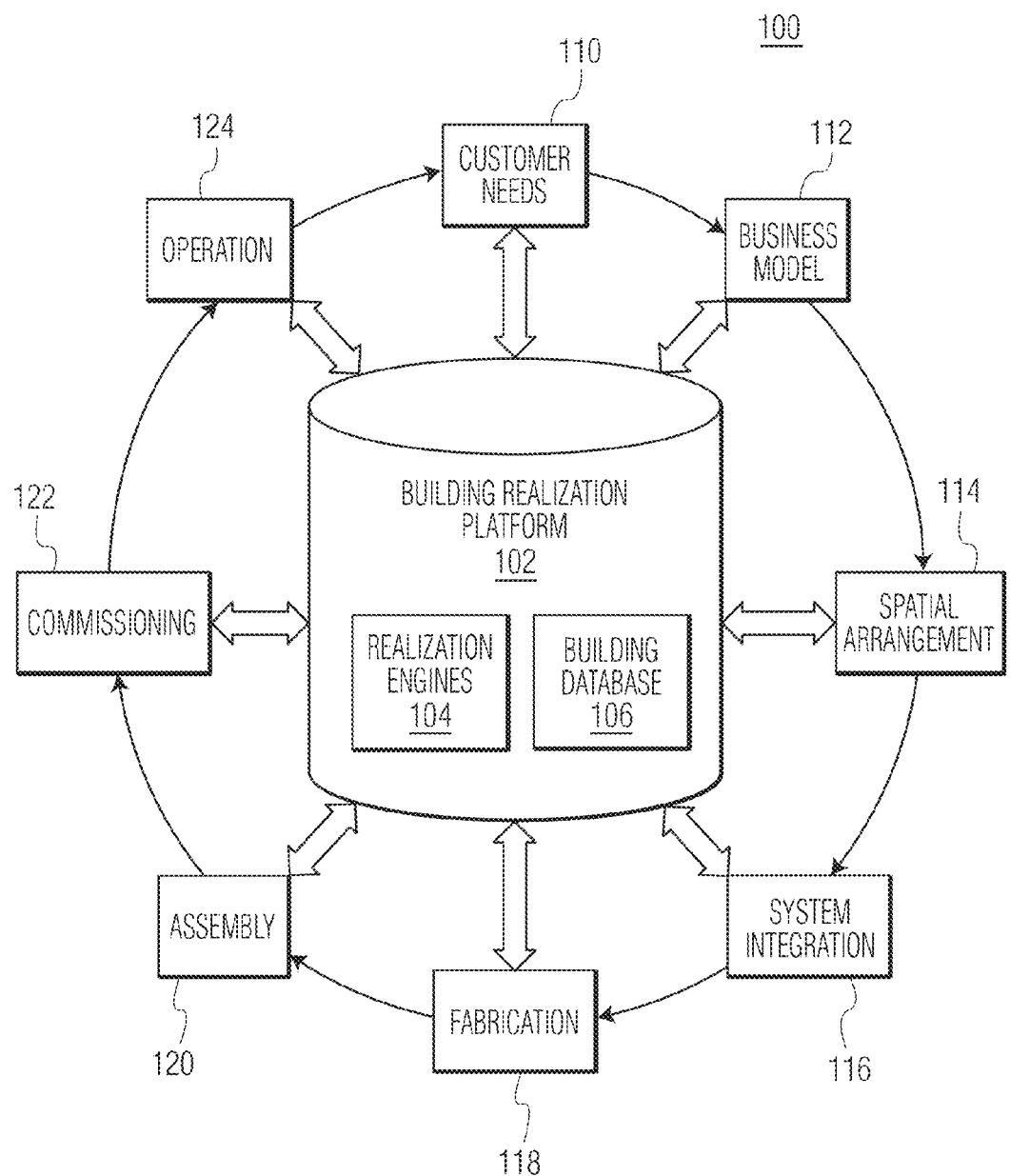
FIG. 1 illustrates a holistic building management system that utilizes high performance and high productivity computing resources to implement a building realization platform that takes a building project from inception to building operation.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment. Rather, language referring to the features and advantages is understood to mean that a specific feature, advantage, or characteristic described in connection with an embodiment is included in at least one embodiment. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment. Thus, the phrases "in one embodiment," "in an embodiment," and similar language throughout this specification may, but do not necessarily, all refer to the same embodiment.

Computers have been used to mathematically describe, model, simulate, and optimize buildings. However, conventional computer-based techniques utilize PC-based computer platforms with limited computing capacity to perform very specific operations that are focused on a single issue, e.g., structural performance, temperature modeling, or workflow optimization. Because of the inherent limitations of PC-based computing resources, conventional design, modeling, simulation, and optimization operations are forced to rely on relatively crude mathematical models that can only evaluate a few design options in a reasonable amount of time. Some characteristics that add complexity to a building system are: the system components do not necessarily have mathematically similar structures and may involve different scales in time or space; the number of components may be large, sometimes enormous; components can be connected in a variety of different ways, most often nonlinearly and/or via a network; local and system wide phenomena may depend on each other in complicated ways; the behavior of the overall system can be difficult to predict from the behavior of individual components; and the overall system behavior may evolve along qualitatively different pathways that may display great sensitivity to small perturbations at any stage. Because of the complexity of such building systems, it is difficult if not impossible to comprehensively design, model, simulate, or optimize such building systems on a PC-based computer platform in a manner that will provide significant advances beyond the conventional techniques.

In accordance with an embodiment of the invention, a holistic approach to a complex building system involves using high-productivity high-performance (HP2) computing resources to manage a complex building system from building inception through to building operation. For example, HP2 computing resources are used to translate a set of customer needs to a complete virtual building design that can be used to construct a building. Further, the information generated during the design of a virtual building can be used as the basis of information that is later used to fabricate, commission, and operate a built version of the virtual building. Because HP2 computing resources are used, modeling, optimization, simulation, and verification can be performed from a single platform on a scale which heretofore has not been applied to complex building systems. Additionally, the holistic approach to complex building systems involves using a centralized database to manage all of the information related to a building system. The centralized database concept is in contrast to the conventional approach where each different discipline (e.g., architects, structural engineers, electrical engineers, etc.) maintains its own proprietary database of discipline-specific information.

FIG. 1 illustrates a holistic building management system 100 that utilizes HP2 computing resources to implement a Building Realization Platform (BRP) 102 that takes a building project from inception (e.g., customer needs) to building operation. The BRP is a central hub of building information that can be maintained from the initial specification of customer needs through building operation. In an embodiment, the BRP includes realization engines 104 and a building database 106. In an embodiment, the realization engines include the logic to drive the design, modeling, simulation, optimization, and verification operations related to a building system and the building database includes stored data related to the building system (virtual and/or real) that is designed, modeled, simulated, optimized, and verified by the realization engine.

From a high-level perspective, the BRP 102 supports a series of hierarchical domains that run in a process flow from more abstract to less abstract. The hierarchical domains shown in FIG. 1 are, from more abstract to less abstract, customer needs 110, business model 112, spatial arrangement 114, systems integration 116, fabrication 118, assembly 120, commissioning 122, and operation 124. In the lifecycle of a complex building system, each of the domains is dependent on the data associated with the previous domains. As such, FIG. 1 also illustrates a temporal relationship between the different domains in that certain details of a preceding domain must be specified before the process can move to the next domain. Additionally, the dependencies between domains are tracked to correspond to the requirements of the previous domain.

In an embodiment, the customer needs 110 domain relates to the desired building system from an owner perspective, that is, what is the use of the building system (e.g., healthcare, hospitality, etc.), where the building system will be located, and what are the metrics and their importance to rate the quality of the design. The business model domain 112 relates to the types and volumes of services that will be provided to satisfy the customer needs. The business model may also support behavioral modeling of the building system, and functional and space programs of the building system. The spatial arrangement domain 114 relates to the building system as a set of building structures implementing a desired architectural parti, with relative placed rooms. The systems integration domain 116 relates to a fully detailed facility including defined 3D spaces and building infrastructure from which detailed construction documents can be derived. The fabrication domain 118 relates to how and how many basic elements (i.e., building blocks) need to be fabricated to construct the building system (e.g., a list of building components). The assembly domain 120 relates to how and in which order the basic elements need to be assembled to construct the building system. The commissioning domain 122 relates to the physical building system and its behavior. The commissioning domain may contain information that is similar to the information held in the systems integration domain but also accounts for deviations that might have occurred during the fabrication and assembly of the building system. The operation domain 124 relates to the building system while in operation. In the operation domain, a virtual model of the building system can be used in real time to optimize processes such as room, staff, and patient scheduling, and to evaluate and adapt to unscheduled events.

In an embodiment, each complex building system is designed, modeled, simulated, optimized, and verified from building inception using a pre-defined set of physical building components. The pre-defined set of physical building components may include, for example, structural components, deck components, and wall components. Each of the pre-defined physical building components has a set of known characteristics (e.g., dimensions, materials of construction, structural performance, thermal performance) that can be utilized in the various domains of the BRP to produce more rapid and accurate results. In particular, the use of pre-defined physical building components allows for the development and reuse of mathematical models that enable design, modeling, simulation, optimization, and validation of complex building systems. The pre-defined set of physical building components can be taken into consideration early on in the building design process, for example, within the business model domain, the spatial arrangement domain, and the systems integration domain.

Figure 2:
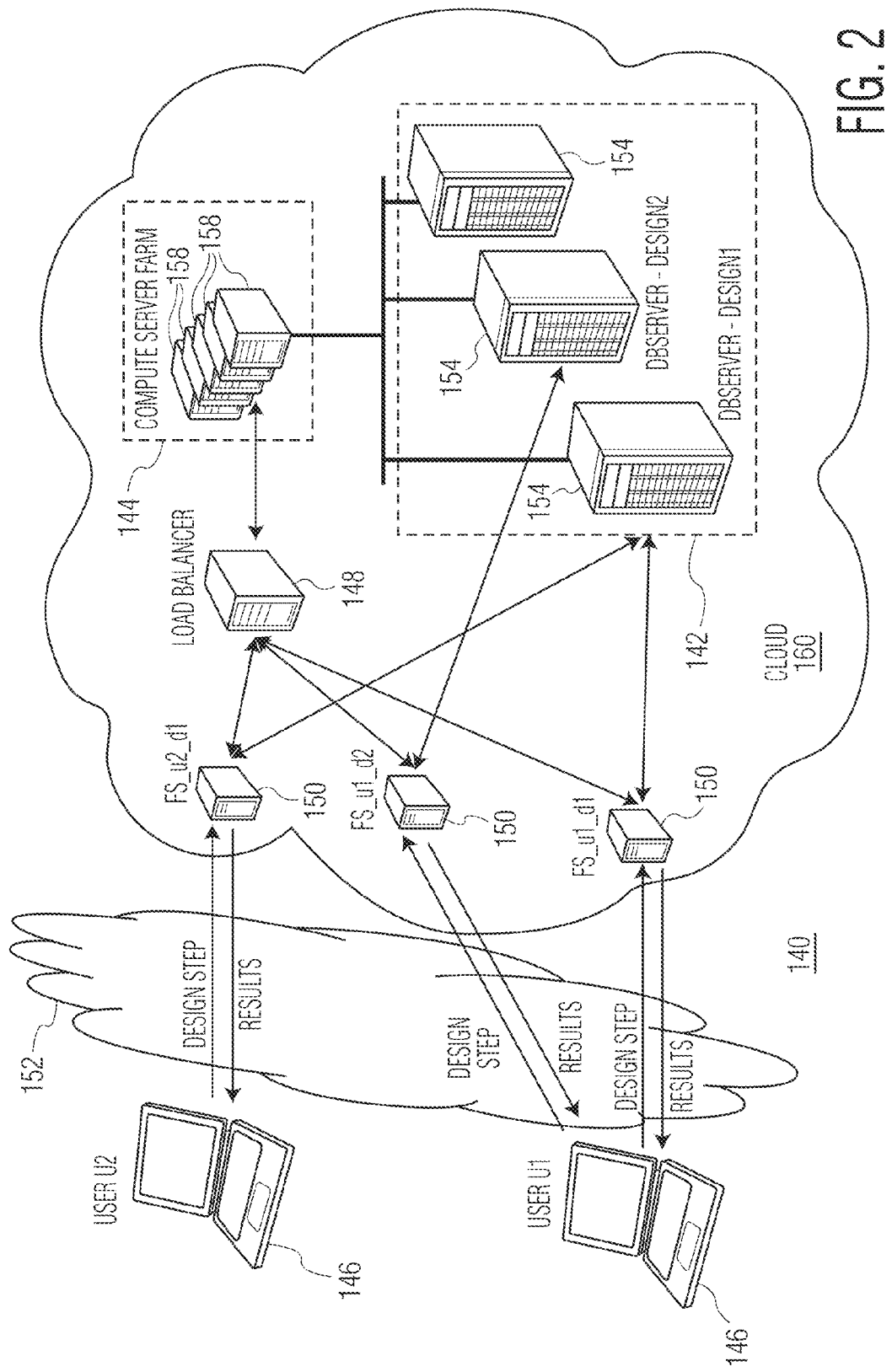
FIG. 2 depicts an embodiment of a high-productivity high-performance computer architecture in which a building realization platform can be implemented.

Performing the processes described with reference to the BRP 102 requires computing resources well beyond what can be provided by typical PC-based computer systems. In an embodiment, the BRP utilizes HP2 computing resources throughout the life cycle of a complex building system. FIG. 2 depicts an embodiment of an HP2 computer architecture 140 in which the BRP can be implemented. In particular, the HP2 computer architecture includes a high capacity networked storage system 142, a large scale processing system 144, and user interface devices 146, e.g., client machines. Additionally, load balancers 148 and flow servers 150 may be provisioned from the large-scale processing system.

The user interface devices 146 may be client machines, typically desktop computers, laptop computers, or tablet computers, on which a session can be opened to control the design flow and to view the performance results of a particular building system design. The user interface devices allow a user to provide design intent and invoke design and analysis steps. Results come in to the user interface devices as they become available. In an embodiment, the user interface devices are used to access a browser-based user interface of the BRP 102 via an access network 152.

The high capacity networked storage system 142 includes memory for storing the software code that is used to implement the realization engine and for storing data related to multiple different complex building systems that are managed using the BRP. In the embodiment of FIG. 2, the high-capacity network storage system includes a networked combination of storage servers 154 that provide storage capacity on the order of Terabits of data.

In contrast to conventional techniques in which each different discipline, e.g., architects, structural engineers, electrical engineers, HVAC engineers, etc., has its own internal proprietary computer networks and a database of building information, the computer architecture depicted in FIG. 2 includes a central repository for data that spans multiple different disciplines related to a complex building system. For example, the data for a specific building may include data related to the customer needs, the business model, spatial arrangement, systems integration, fabrication, assembly, commissioning, and operation. This may include information that crosses many of the disciplines that are conventionally involved in the life cycle of a building. In the embodiment of FIG. 2, the large-capacity storage system 142 includes one or more storage servers that store the building database 106 information and one or more servers that store the computer instructions to implement the realization engines 104.

In an embodiment, the database servers 154 store design information organized as follows: a construction data base, an analysis database, a library of process knowledge, and a library of design rules. The construction database may contain various system descriptions that are independent from how the systems were constructed. The analysis database may contain performance and quality results, obtained through various analyses and simulations of the systems contained in the construction database. The library of process knowledge may contain information related to processes, people patterns, department patterns, building patterns, and mechanical, electrical, and plumbing (MEP)

routing patterns. The library of design rules may contain building codes, such as egress, fire and accessibility requirements, and industry best practices (note that there can be different sets of design rules stored to comply with local variations of building rules). Although an example, of a particular database organization is described, other ways of organizing the data is possible.

The large-scale processing system 144 performs the computer processing that is necessary to implement the BRP. For example, the large-scale processing system performs high-volume mathematical computations to implement the design, modeling, simulation, optimization, and verification of the BRP. In an embodiment, the large scale processing system includes multiple servers 158 (i.e., a server farm or compute farm) that each have many high-speed processors (e.g., on the order of thousands and up), where the individual servers are connected to each other by high-speed network links such as Gigabit Ethernet. Such large scale processing systems can perform on the order of Tera- ($10^{12}$) to Peta- ($10^{15}$) floating point operations per second (Flops), referred to as TFlops and PFlops, respectively. Examples of large scale processing systems include the CRAY XT3, having 3,328 processing cores and the CRAY XT5, having 14,752 processing cores. In an embodiment, the large scale processing system utilizes a grid computing architecture and/or multi-core processors to implement distributed computing according to a "MapReduce" framework. Although examples of the large-scale processing system are described, other large-scale processing systems are possible.

The flow servers 150, which can be virtual, one per user interface device 146 and design, may be compute engines borrowed from the large scale processing system 144 (e.g., server farm), which execute the instructions that implement the BRP design flow. In an embodiment, the flow servers hold the design state of each unique design. That is, the flow servers know the phase of the design cycle for a particular design. Typically, the flow servers hold just enough of the design in memory to allow efficient transfer of design intent, results, and job submission. For computationally intensive tasks, the flow servers submit processing jobs (i.e., computational tasks) to the load balancer 148 and the load balancer distributes the computational tasks based on project, user, and task priorities.

Compute servers 158 of the large-scale processing system 144 are used by the flow servers 150 to perform computational intensive tasks using, for example, map reduced or "MapReduce" techniques for parallel processing. In an embodiment, the compute servers are pooled among flow servers by the load balancer 148. The compute servers can pull large amounts of design information directly from the database servers 154 of the high capacity network storage system 142 and save raw results back to the storage system.

In an embodiment, some or all of the computing resources (excluding the user interface devices) are provided as a "cloud service." For example, the HP2 computing resources of FIG. 2 are provided as a cloud service within a network cloud 160. That is, the computing resources are not owned by the owner or user of the BRP, but are instead utilized and paid for by the owner or user of the BRP on an as needed basis. For example, cloud services such as those provided by Amazon Web Services (AWS) may be utilized to implement the BRP 102.

The HP2 computing architecture 140 depicted in FIG. 2 differs from conventional industry practices in many ways. In particular, the functions of control and presentation are isolated in thin client user interface devices 146, while all compute tasks are performed in a well controlled and high performance cloud service containing both the compute and database servers. The compute machines are not allocated per type of task or discipline (architects, construction engineer, mechanical engineer, operations analyst), but are pooled to serve as flow servers and compute engines. This centralized approach optimizes efficiency in that the flow servers are drawn out of the compute pool as a design session starts and the flow servers coordinate all tasks for that design session. Additionally, the database servers are not organized per discipline, that is, they are not organized separately for each discipline, e.g., one database server each for the architect, the construction engineer, the mechanical engineer, and the operations analyst. In the architecture of FIG. 2, high bandwidth/high volume data transactions occur only between the database servers 154 and the compute servers 158.

Figure 3:
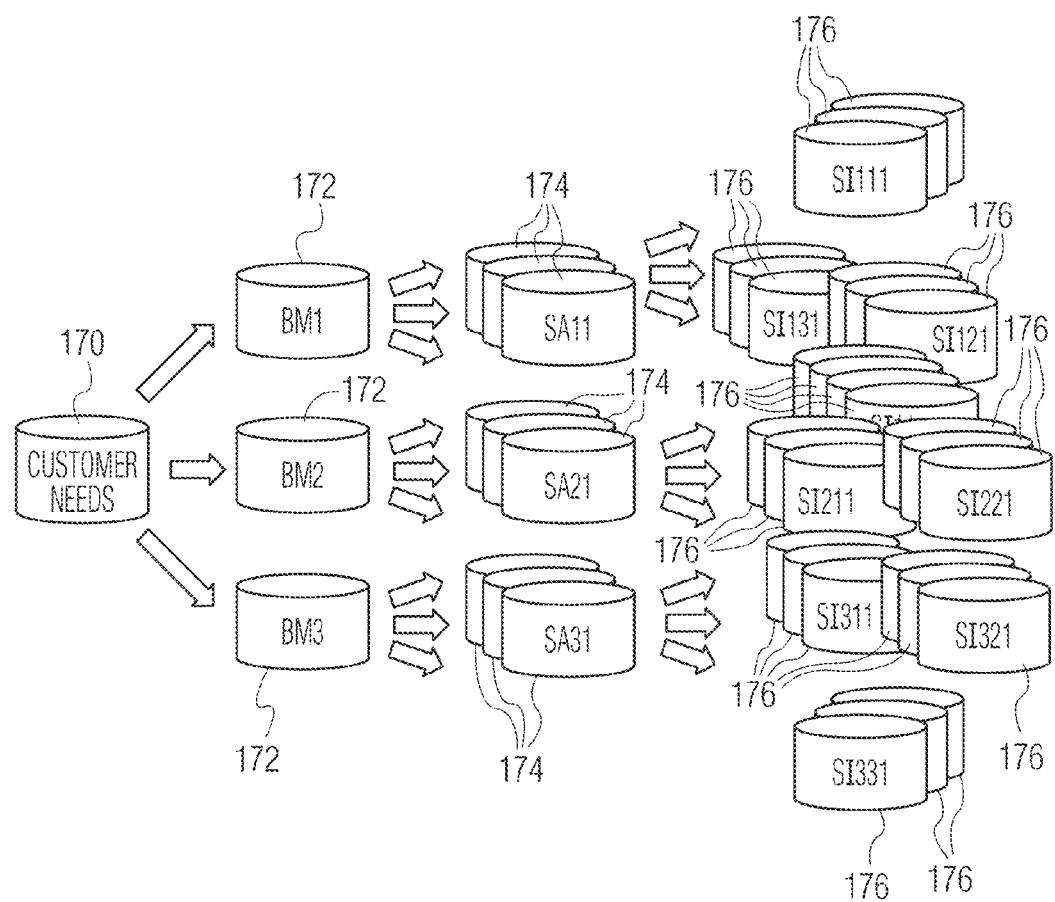
FIG. 3 illustrates an embodiment of a parallel hierarchical design technique that is implemented using the building realization platform.

The BRP 102 and the HP2 computing architecture 140 as described with reference to FIGS. 1 and 2 are utilized in combination to implement a hierarchical parallel design technique, from building inception to a fully defined systems integration, which heretofore has not been envisioned in the field of building design. FIG. 3 illustrates an embodiment of a parallel hierarchical design technique that starts at the customer needs, e.g., building inception, and runs through to a multitude of fully defined systems integrations. Using HP2 computing resources, many different options can be realized and vetted in parallel within each domain from business modeling, to spatial arrangement, to systems integration. At each step in the process, instance-specific data can be stored and maintained for use in subsequent design analysis and/or modification. Additionally, the parallel hierarchical approach allows for the development and tracking of many different design schemes that all relate back to the same set of customer needs. In the embodiment of FIG. 3, a database of customer needs 170 is used to generate a set of different business models, business models databases 172. The database of each different business model is used to generate a set of spatial arrangements, which are stored as spatial arrangement databases 174. The database of each different spatial arrangement is used to generate a set of systems integration designs, which are stored as systems integration design databases 176.

Figure 4:
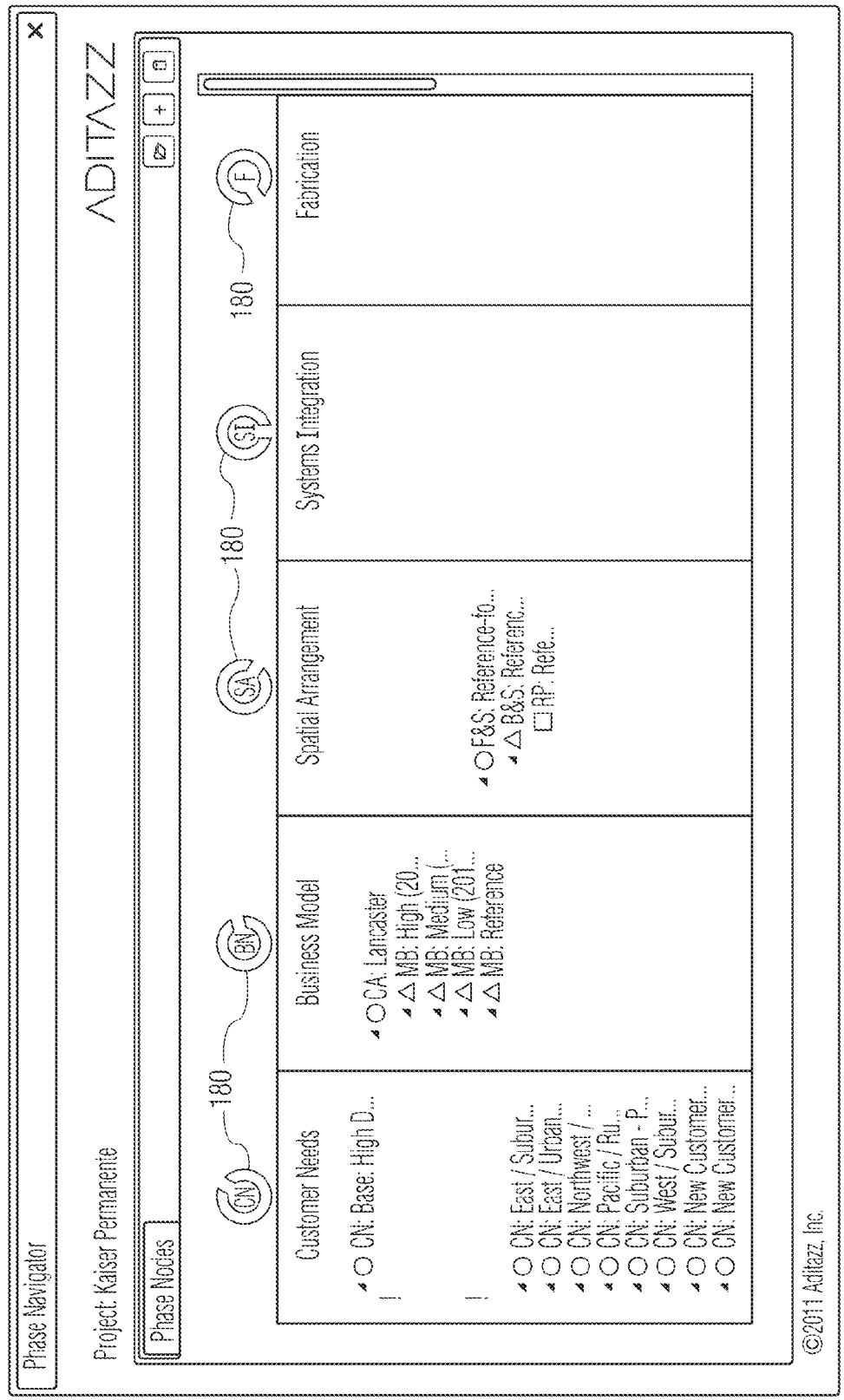
FIG. 4 depicts an embodiment of a user interface of the building realization platform that includes selectable tabs for activating realization engines of the building realization platform.

The parallel hierarchical process illustrated in FIG. 3 is now described in more detail with reference to FIGS. 3-10. FIG. 4 depicts an embodiment of a user interface of the BRP 102 that includes selectable tabs or icons 180 for activating operations in the customer needs domain 110, the business model domain 112, the spatial arrangement domain 114, the systems integration domain 116, and the fabrication domain 118 of the BRP. Within the customer needs domain, customer needs are specified. In an embodiment, customer needs are presented in a web-based user interface at a client device as a formal description of customer needs. For example, the formal description of customer needs is a formal description of information, as known in computer science, which correctly, precisely, and unambiguously represents certain concepts so that the customer needs can be acted upon.

In an embodiment, customer needs are input to the BRP 102 via a client device by an entity that is looking to build a building for a particular use, such as a healthcare facility. For example, the entity or "customer" may specify that it wants to provide enough acute healthcare services to residents within a specific ZIP code to meet anticipated demand. In another embodiment, customer needs may reflect a project location, service objectives, business objectives, and/or a prioritization of customer needs. For example, the customer needs may specify the types of services that will be provided in the building, the volume of services that will be provided in the building, capital investment limitations, return on investment (ROI) requirements, and/or metrics to rate the quality of various design alternatives. Upon being specified, the customer needs are associated with a particular project and stored in the database of the BRP.

In an embodiment, customer needs related to a healthcare building system include a desired location for the building system, a model of care for the building system, and values of the customer. With respect to values, the user interface may allow the user to rate, on a sliding scale, how the user values concepts such as innovation, sustainability, life cycle cost, healthcare improvement, efficiency, and flexibility. In an embodiment, the customer needs domain can provide the user with outputs such as a map of the desired building system location, census data for the desired location, and public health information, such as Centers for Disease Control (CDC) information. In an embodiment, the map may include pointers or "pins" that identify related facilities, e.g., other healthcare facilities, doctors, labs, etc., which are located in the vicinity of the desired location.

The information related to the customer needs can then be stored in the customer needs database 170 of the BRP 102. For example, the project is given a name and the project information including the location, model of care, value ratings, map information, census information, and CDC information is all stored in the BRP's database under the project name. Different projects can be established with different project names and any of the user specific criteria in the customer needs domain can be changed.

With customer needs specified, the process can move to the business model domain 112, were customer needs are used as input and multiple different business models are provided as an output. In the embodiment of FIG. 3, three different business models are provided as an output (BM1, BM2, and BM3), although it should be understood that many more different business models could be generated from the same set of customer needs. In an embodiment, a business model defines the "program" of the building needed to meet the specified customer needs. For example, the business model specifies what types of services will be provided in the building and at what volume the services will be provided. The business model may also specify an initial shell of the building. Therefore, the business model may include both space dimensions and time dimensions.

As illustrated in FIG. 3, multiple different business models can be generated in parallel from the same set of customer needs. In an embodiment, the generation of business models includes a computationally intensive process of design, simulation, optimization, and validation that is able to generate and evaluate a large number of different designs in parallel. For example, it is possible to design, simulate, optimize, and validate on the order of hundreds to thousands of different iterations related to the business models in tens of minutes (e.g., less than one hour) from a single set of customer needs.

In an embodiment, one computationally intensive operation performed in the business model domain 112 involves behavioral simulation to determine the types and volumes of services that should be provided by a particular building. Behavioral simulations are well suited for the study of the processes that underlie formulation and implementation of a business model. For example, behavioral simulations may involve measuring variables at multiple levels, controlling or measuring the context, dealing with historical facts, capturing process differences across issues, and linking processes to outcomes. The behavioral simulations performed in the business model domain are logically linked to the resulting design, construction, and operation of the building.

Throughout the business model domain 112, the BRP 102 tracks dependencies back to the customer needs so that there is a direct relationship between the customer needs and the business models that are generated to meet the customer needs. A change in the customer needs can be propagated to the business model domain and changes can be made to the business model as needed to meet customer needs. Additionally, already generated business models can be evaluated in light of changes to the customer needs. Further, each instance of each different business model is uniquely stored in the database so that each instance can be independently accessed and modified. Unique storage of each instance of a business model allows individual business models to be accessed, evaluated, and/or modified without affecting other business models that correspond to the same set of customer needs.

In an embodiment, the business model identifies the service lines (e.g., emergency care, well care, imaging, laboratory) and/or departments that are to be provided by the building system, the patient load on the building system, and the room and staff needs (e.g., the number and types of rooms and the number and types of staff). The outputs of the business model can be provided to a user via a user interface of the BRP 102.

Figure 5:
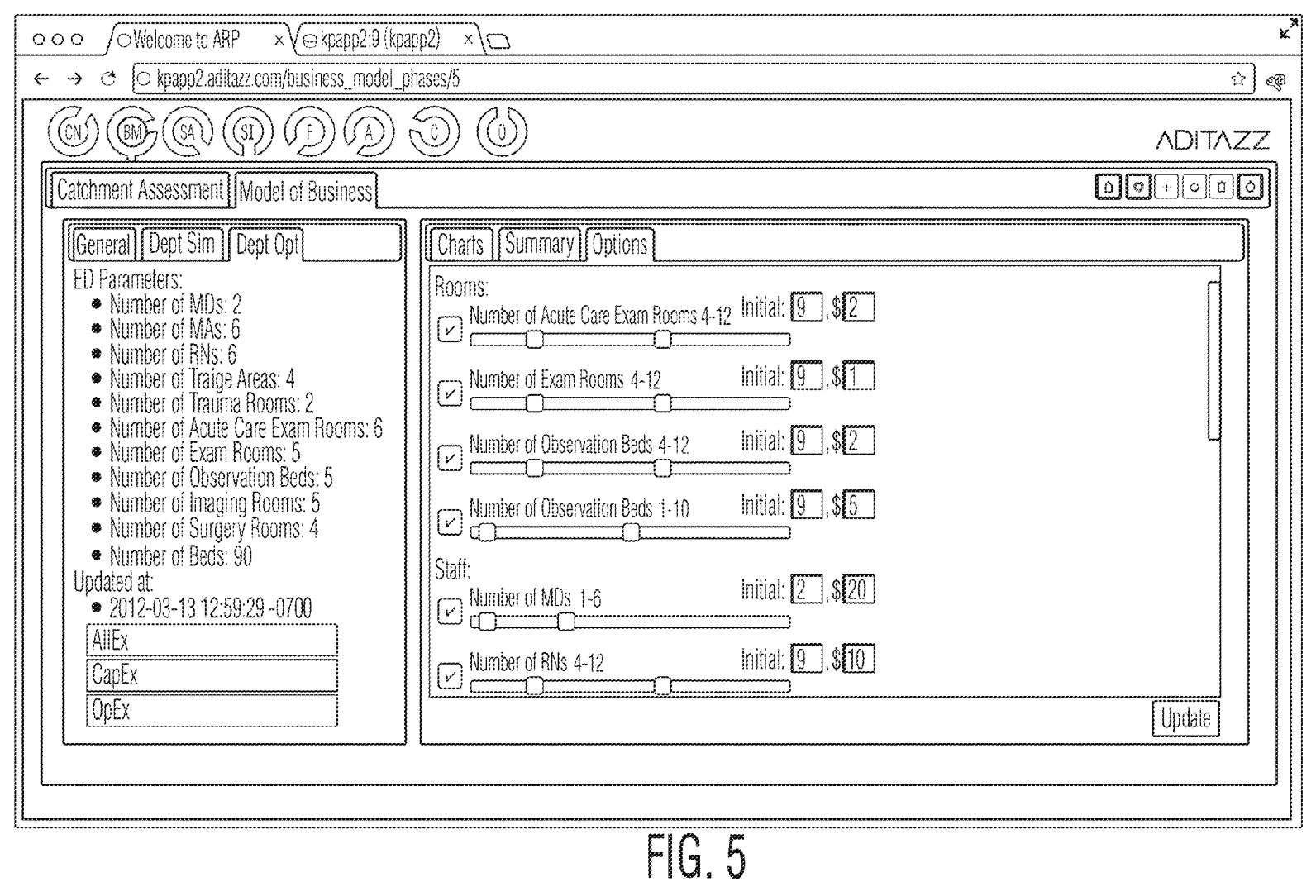

FIG. 5 depicts an embodiment of a user interface from the business model domain 112 of the BRP 102. The user interface displays information about the business model such as number of medical doctors (MDs), number of medical assistants (MAs), number of registered nurses (RNs), number of triage areas, number of trauma rooms, number of acute-care exam rooms, number of exam rooms, number of observation beds, number of imaging rooms, number of surgery rooms, and number of beds. Within the business model domain, the behavior of the building system can be simulated based on the criteria of the building model and various workflow logic that is incorporated into the BRP. The user interface of the BRP also enables certain parameters of the business model to be modified for use in simulation. For example, the user interface enables the user to adjust parameters related to any of the business models, such as the number of acute-care exam rooms, the number of exam rooms, the number of observation rooms, the number of trauma rooms, the number of medical doctors, and the number of registered nurses.

Figure 6:
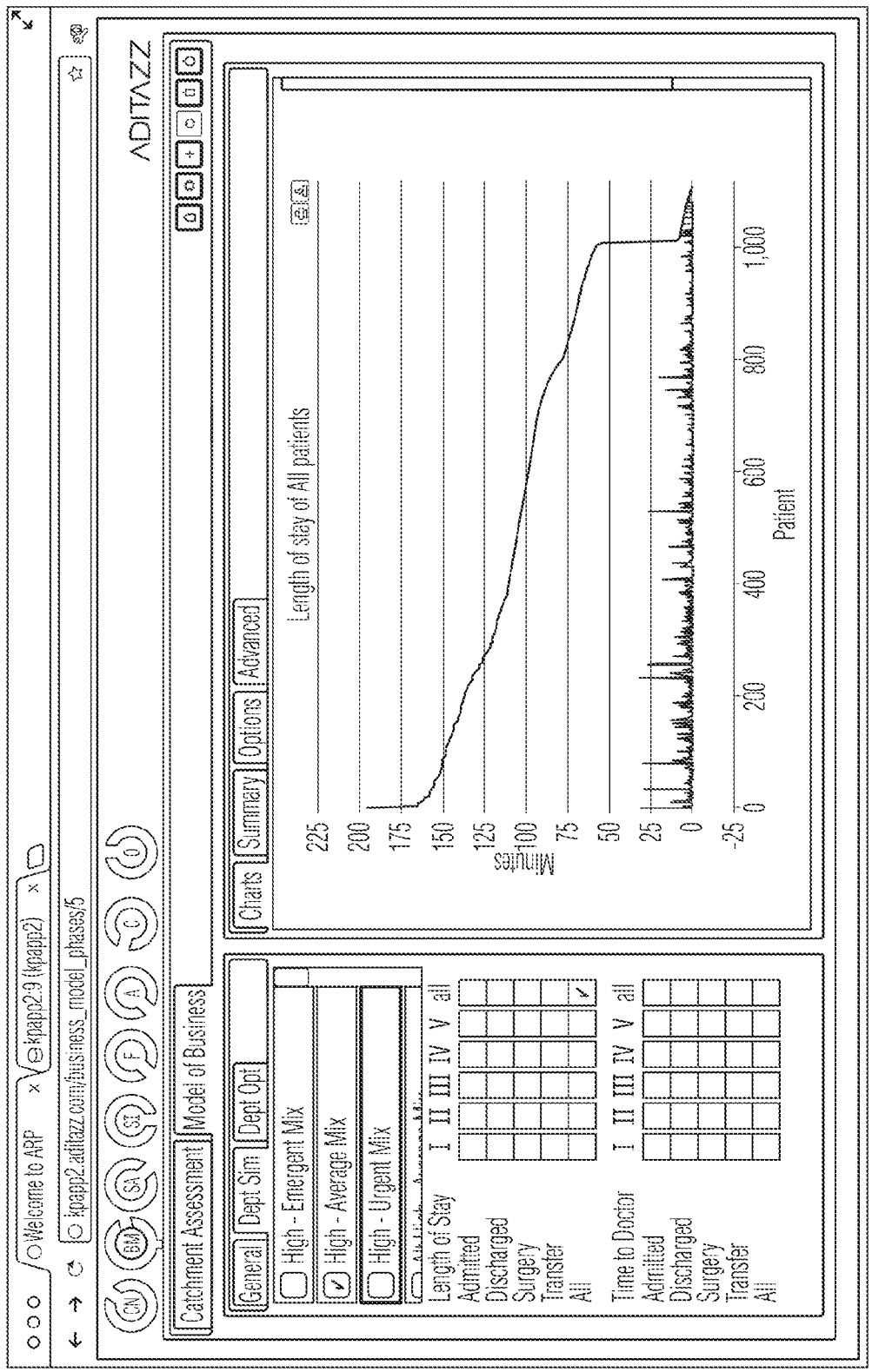
FIG. 6 depicts another embodiment of a user interface from the business model domain of the building realization platform.

FIG. 6 depicts an embodiment of a user interface from the business model domain 112 that shows simulation results generated within the business model domain. For example, the results relate to the length of stay of patients given a certain set of input parameters. In an embodiment, event driven simulations are implemented and the different simulations are set up to use specific HP2 computing resources. For example, each computational operation is mapped to a specific set of processing hardware in the large-scale processing system using MapReduce techniques.

Referring back to FIG. 3, with various different business models specified, the parallel hierarchical process can move to the spatial arrangement domain, where business models are used as input and multiple different spatial arrangements are provided as an output. In the embodiment of FIG. 3, at least three different spatial arrangements are generated for each business model. As shown, spatial arrangements SA11, SA12, and SA13 are generated from BM1, spatial arrangements SA21, SA22, and SA23 are generated from BM2, and spatial arrangements SA31, SA32, and SA33 are generated from BM3. Although three different spatial arrangements are generated from each business module, it should be understood that many more different spatial arrangements could be generated from the same set of business models. In an embodiment, a spatial arrangement defines a building system as a 3D space that includes the basic structure of the building and the placement of rooms. For example, the spatial arrangement defines the approximate square footage of the building, the number of floors in the building, and the number, types, locations, square footage, and functionality of the rooms within the building.

In an embodiment, the spatial arrangements are generated in parallel using the computational resources of the large scale processing system. For example, the computing resources of the large scale processing system are used to design, model, simulate, optimize, and verify the different spatial arrangements.

In an embodiment, processing in the spatial arrangement domain 114 involves the computer assisted placement of departments and/or rooms based on adjacency criteria and behavioral simulation performance. Using computer-assisted placement and HP2 computing resources, many different spatial arrangements can be modeled, simulated, optimized, and verified in a relatively short period of time. For example, an energy efficiency simulation of the building system may involve one thousand separate computational tasks or jobs that each require one hour to complete. Using HP2 computing resources, the one thousand separate computational tasks can be processed in parallel by separate processors (e.g., separate physical hardware devices), reducing the time required to complete the entire task by roughly one thousand fold.

Within the spatial arrangement domain 114, the BRP 102 tracks dependencies back to the corresponding business models so that there is a direct relationship between the spatial arrangements, the building models, and ultimately the customer needs. A change in the customer needs or business model domains can be propagated to the spatial arrangement domain and changes can be made to the spatial arrangements as necessary. Further, each instance of each different spatial arrangement can be uniquely stored in the database so that each instance can be independently accessed and manipulated. Because the business models and spatial arrangements are maintained in hierarchical order, only changes that affect a particular hierarchical chain need to be propagated to the spatial arrangements. For example, if a change is made to an aspect of BM1 only, the change can be propagated to the spatial arrangements, SA11, SA12, and SA13 only, while the spatial arrangements that are linked to BM2 and BM3 (e.g., SA21, SA22, SA23, and SA31, SA32, SA33, respectively) are not affected.

Figure 7:
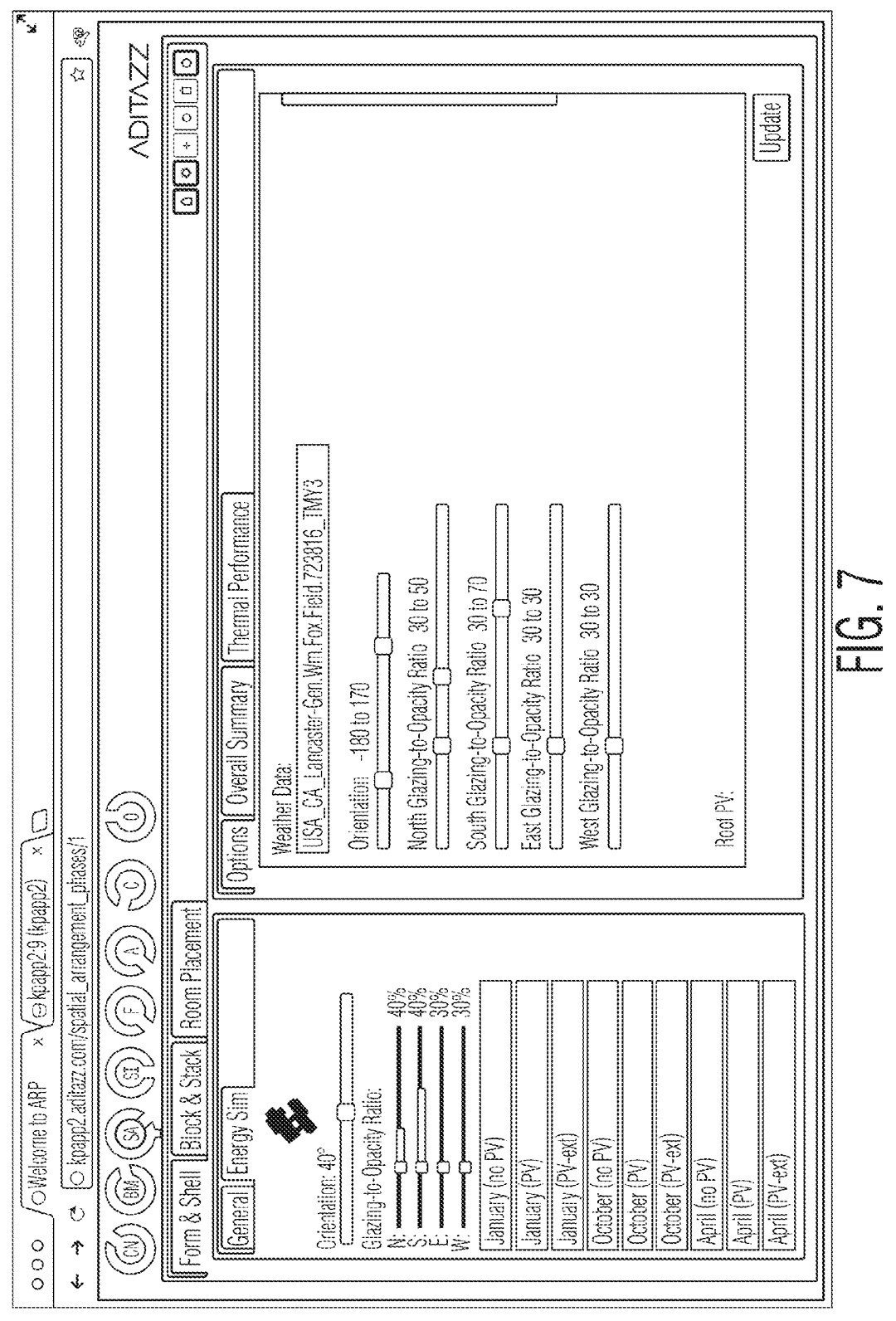

In an embodiment, a spatial arrangement specifies aspects of the building system related to "form and shell," "block and stack," and "room placement." In an embodiment, the form and shell within the spatial arrangement domain 114 specifies parameters such as the shape (e.g., architectural pattern or architectural parti) and dimensions of the building system. The form and shell may also specify the orientation and location of the building on the site specified in the customer needs. From the specified form and shell, various models, simulations, and/or optimizations can be performed using the HP2 computing resources. For example, using the HP2 computing resources, energy efficiency simulations and optimization operations can be performed on a scale that heretofore has not been possible. FIG. 7 depicts an embodiment of a user interface from the form and shell tab in the spatial arrangement domain that shows adjustable parameters of an energy efficiency simulation that is implemented at the form and shell level. Adjustable parameters for the simulation include the time of year (e.g., month), the orientation of the building, and glazing-to-opacity ratios in different directions, e.g., east, west, north, south.

Figure 8:
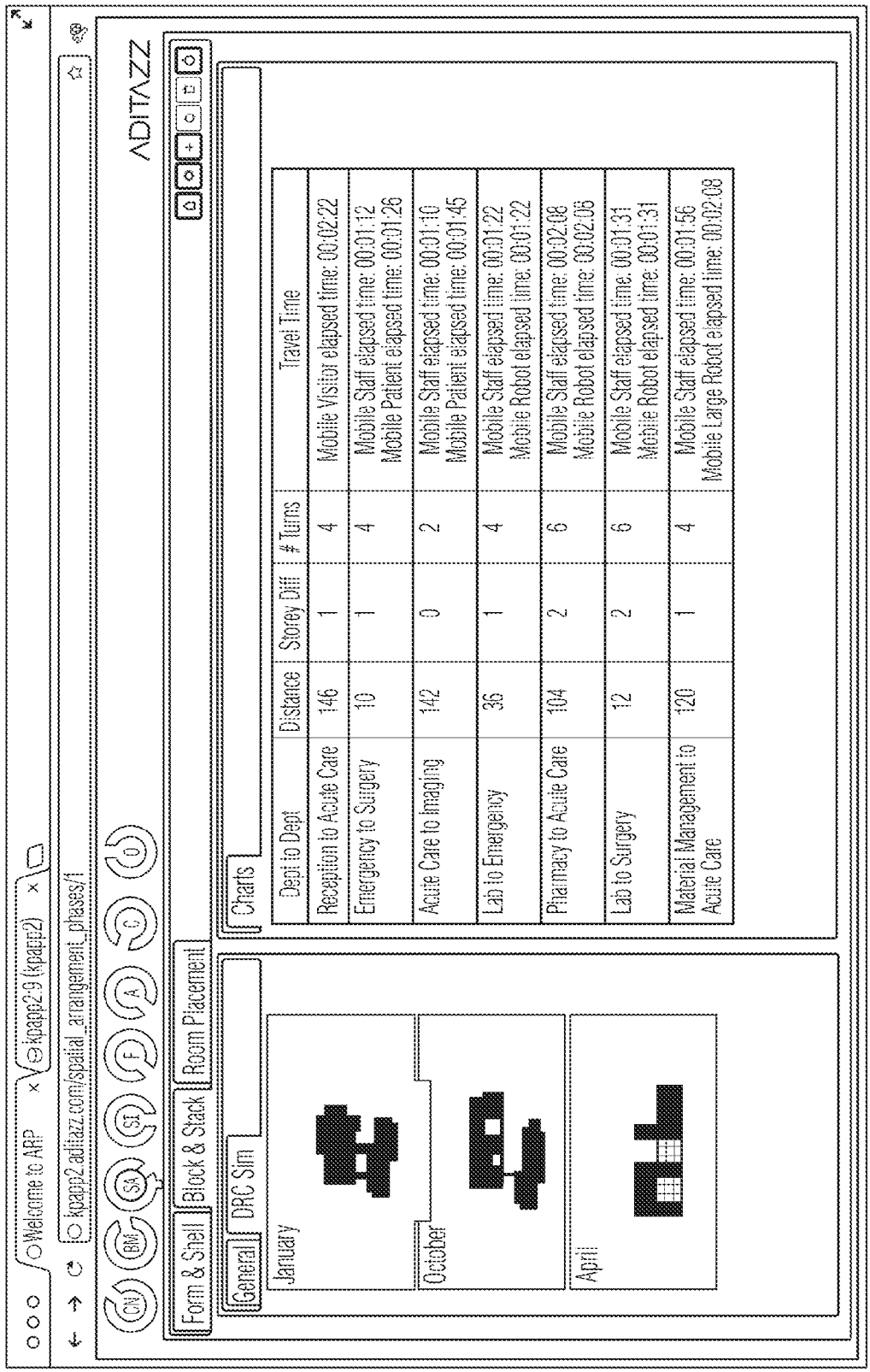
FIG. 8 depicts an embodiment of a user interface from the block and stack tab of the spatial arrangement domain of the building realization platform.

In an embodiment, block and stack within the spatial arrangement domain 114 specifies how departmental blocks and circulation elements are placed within the specified form and shell of the building system. For example, the block and stack defines how departmental blocks are configured relative to each other in the horizontal direction and how departmental blocks are configured, or "stacked," relative to each other in the vertical direction (e.g., between different floors of a multistory building). From the specified block and stack, various models, simulations, and/or optimizations can be performed using the HP2 computing resources. For example, operations may include interactive departmental distance exploration, behavioral simulation with department distances, and generation of individual departmental blocks. FIG. 8 depicts an embodiment of a user interface from the block and stack tab of the spatial arrangement domain that shows the output of a simulation to determine travel distances and times between certain departments given a particular block and stack.

Figure 9:
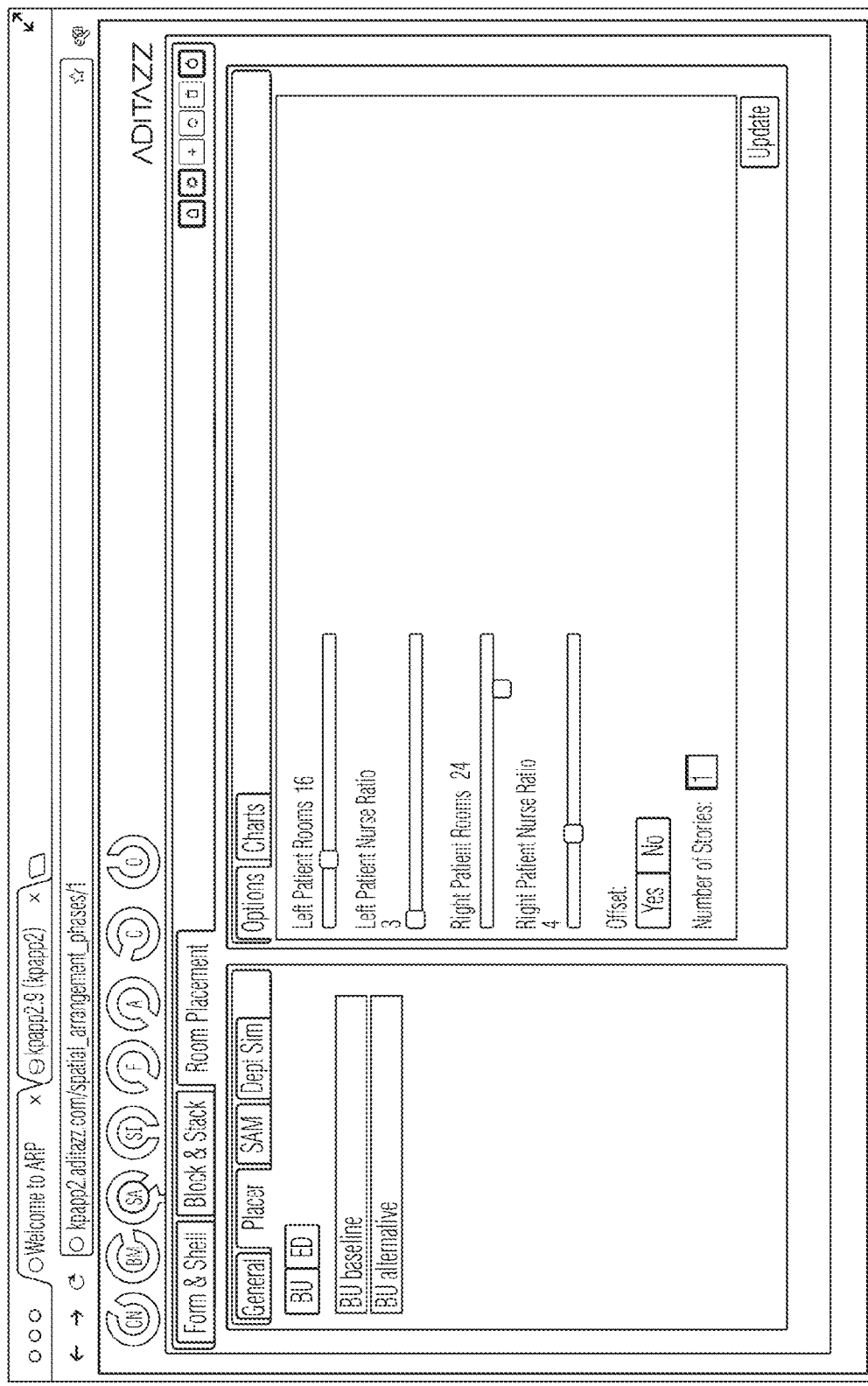
FIGS. 9 and 10 depict user interfaces from the room placement tab of the spatial arrangement domain of the building realization platform.
Figure 10:
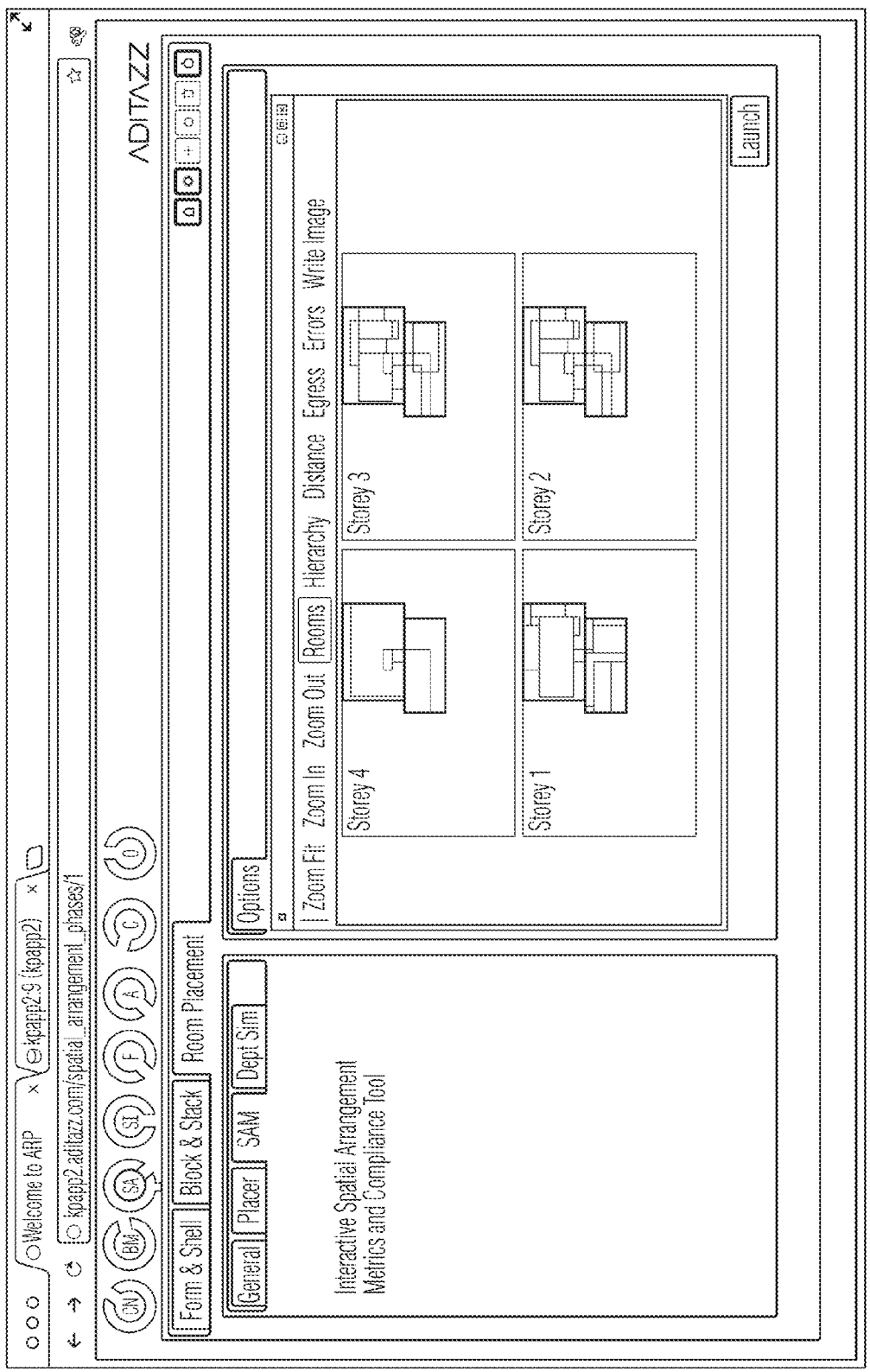

In an embodiment, room placement within the spatial arrangement domain 114 specifies the locations of specific rooms within a building system having a specific block and stack arrangement. From the specified room placement, various models, simulations, and/or optimizations can be performed using the HP2 computing resources. For example, operations may include interactive room distance exploration, behavioral simulation with room distances, and egress design rule checking FIGS. 9 and 10 depict user interfaces from the room placement tab of the spatial arrangement domain. In particular, FIG. 9 depicts certain adjustable criteria for room placement and FIG. 10 depicts different room placement designs that are generated based on a given set of criteria.

Referring back to FIG. 3, with various different spatial arrangements generated and stored, the process can move to the systems integration domain, where spatial arrangements are used as input and multiple different systems integration designs are provided as an output. In an embodiment, a systems integration design defines the 3D spaces of a building and the infrastructure of the building. For example, the systems integration design for a building defines the locations in three dimensions (i.e., "3D spaces) of the infrastructure elements of the building system. The building infrastructure specified in the systems integration design may include, for example, the location and specifications of mechanical, electrical, and plumbing (MEP) systems, information technology (IT), safety and security elements, and lighting. In the systems integration designs, the locations of the building infrastructure elements are fully defined and integrated into the 3D spaces of the building system. In an embodiment, the systems integration designs are generated in parallel using the computational resources of the large scale processing system to design, model, simulate, optimize, and verify the different systems integration designs.

In the embodiment of FIG. 3, at least three different systems integrations are generated for each spatial arrangement. As shown, systems integration designs SI111, SI112, SI113 are generated for spatial arrangement SA11, systems integration designs SI121, SI122, and SI123 are generated for spatial arrangement SA12, systems integration designs SI131, SI132, and SI133 are generated for spatial arrangement SA13, and so on for a total of twenty-seven different systems integration designs. Although three different systems integration designs are generated for each spatial arrangement, it should be understood that many more different systems integration designs could be generated from the same set of spatial arrangements. As illustrated in FIG. 3, a large number of design options can be generated from the same set of customer needs. Further, the computational task of designing, modeling, simulating, optimizing, and verifying all of the different design options can grow to be quite large quite fast. Hence, the use of HP2 computing resources along with a centralized BRP 102 is key to enabling the parallel hierarchical design technique.

Figure 11:
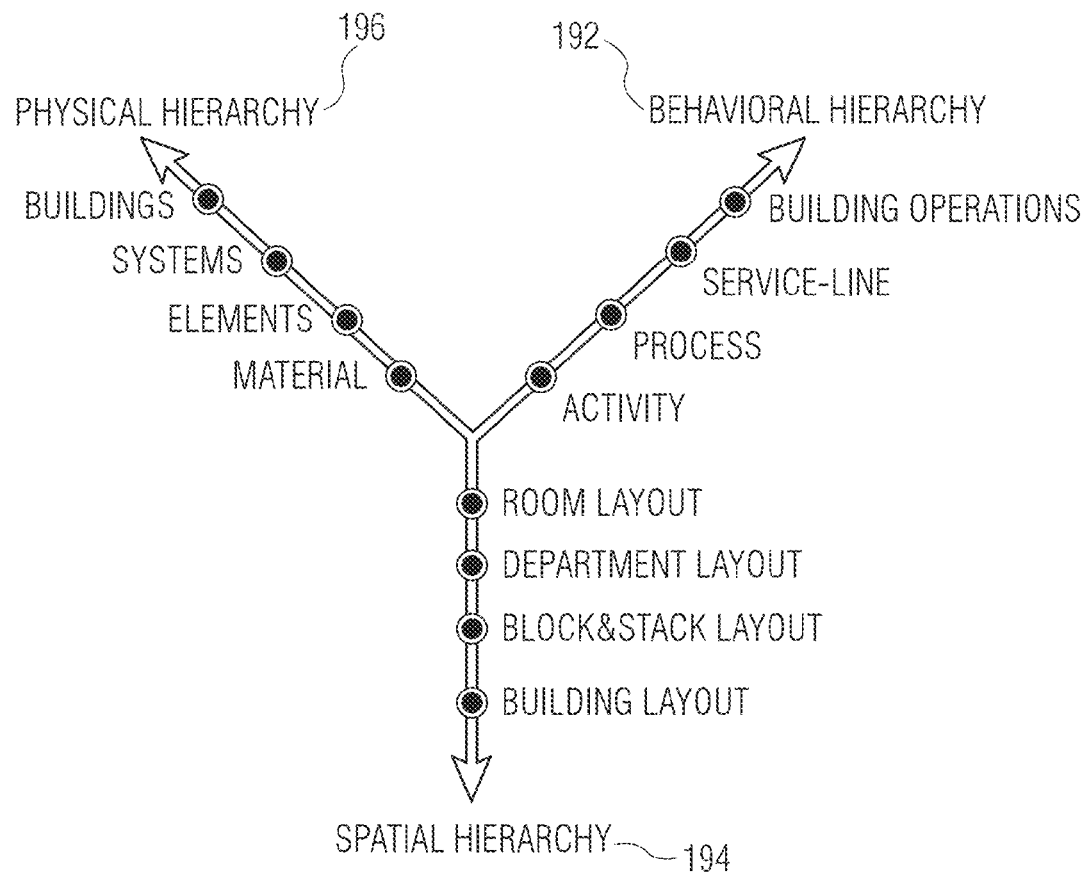
FIG. 11 illustrates an example of a unified data model that is used by the building realization platform.

In an embodiment, the process of going from a set of customer needs to a systems integration design is supported by a unified data model that is maintained by the BRP 102. FIG. 11 illustrates an example of a unified data model 190 that is used by the BRP in the design, modeling, simulation, optimization, and verification of a computer building system. As illustrated in FIG. 11, the unified data model includes a behavioral hierarchy 192, a spatial hierarchy 194, and a physical hierarchy 196.

In an embodiment, the behavioral hierarchy 192 defines the operational and business processes from single activities by individuals in dedicated rooms using specific equipment, to processes in departments, processes in service lines or business units to a building-wide operational model. The behavioral description can have various degrees of abstraction. For example, a department can be described as a single activity incurring costs and producing revenue, towards an activity handling patients, taking time, incurring costs and producing revenue, or an activity of staff handling patients, requiring specific equipment. Besides the human behavioral description, there can also be behavioral descriptions for non-human elements such as, for example, energy, light, and water. In FIG. 11, the behavioral hierarchy ranges from activity, to process, to service, to building operations, with each level in the behavioral hierarchy being more abstract than its predecessor.

In an embodiment, the spatial hierarchy 194 describes how the volume of a building is organized. For example, a building has stories, each story has departmental blocks and corridors, departmental blocks have rooms, hallways and circulation spaces, rooms contain furniture/fixtures/equipment (FFE) elements. Spatial descriptions can have various degrees of abstraction. For example, a building can be described from a vague buildable volume, a volume dictated by the site, physical constraints, legal constraints, and owner desires, towards the concept of an architectural parti describing a building configuration, e.g., an atrium versus a spine, towards a description of the major horizontal and vertical circulation areas, towards a global allocation of departments into various sections of the building, towards the exact location of every room and corridor in the building. In FIG. 11, the spatial hierarchy ranges from room layout, to department layout, to block and stack layout, to building layout, with each level in the spatial hierarchy being more abstract than its predecessor.

The physical hierarchy 196 describes how the physical building will be composed from a list of predefined building components. In FIG. 11, the physical hierarchy ranges from material, to elements, to systems, to buildings, with each level in the physical hierarchy being more abstract than its predecessor. For example, the building elements may include a set of predefined physical components such as interior walls, exterior walls, floor panels, roof panels, bathroom pods, aggregate equipment wall floor modules, equipment components and pods, utility frames, rebar cages for concrete structures, metal and concrete floor assemblies, structural steel, and utility systems. In an embodiment, certain aspects of the building components, such as dimensions, performance characteristics, aesthetic ratings, environmental concerns, cost, product life, etc., are known in advance and used as desired in the different domains of the BRP 102. As stated above, the use of predefined building components, each with known characteristics, allows for the development and reuse of mathematical models to design, model, simulate, optimize, and verify complex building systems.

For each of the data hierarchies and at each hierarchical level, there is both an abstract description and one or more structural descriptions. That is, within the unified data model, an object is described as consisting of a set of connected instances of objects of a lower level. For example, a process of a patient coming in for a regular exam could be described as a connected graph of individual activities involving different people and occurring at different locations. The unified data model may be used by the BRP in the design, simulation, optimization, and/or verification operations.

Figure 12:
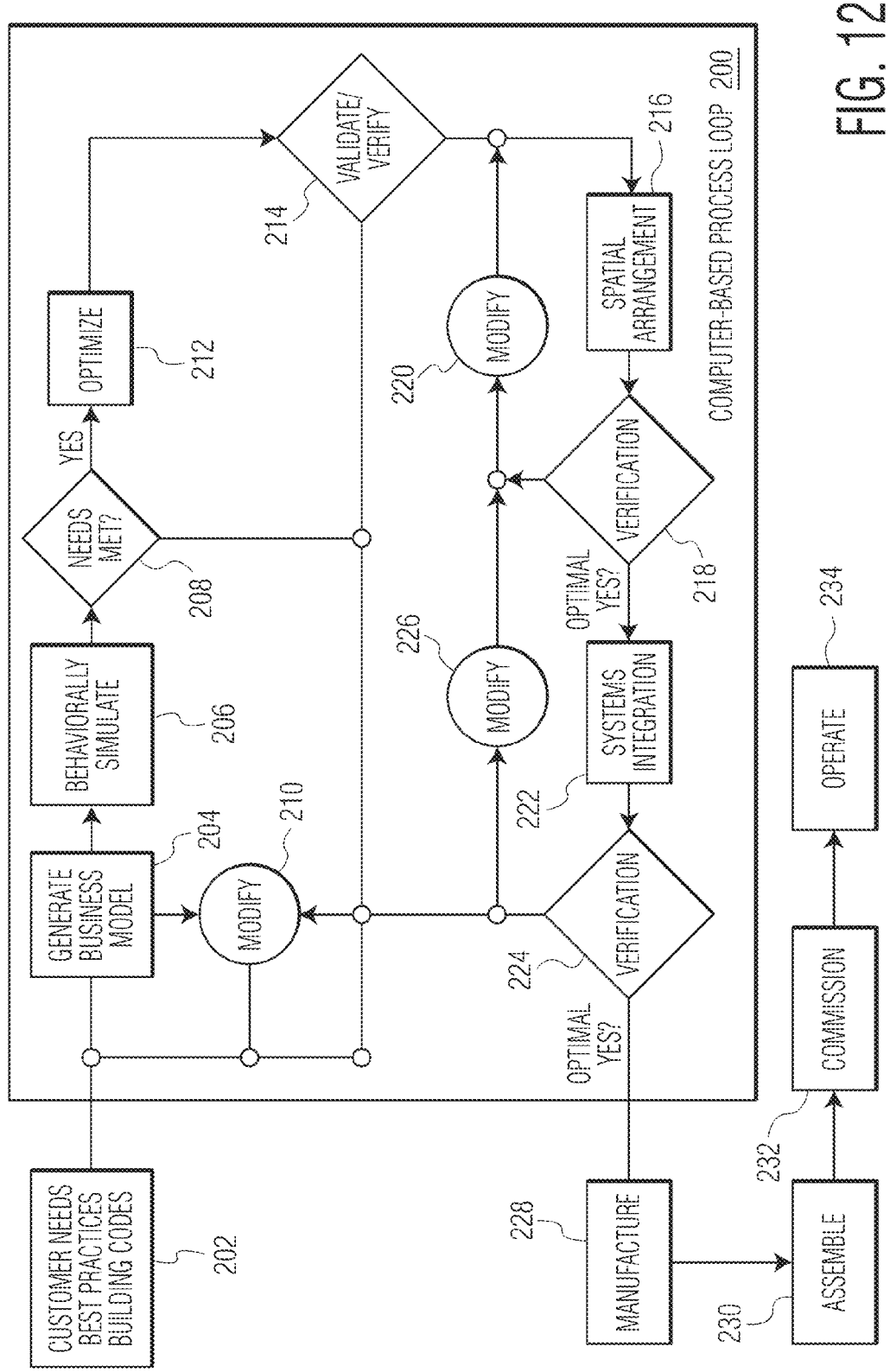
FIG. 12 is a process flow diagram of a computer-based technique for generating a systems integration design from a set of customer needs.

A parallel hierarchical design technique has been described with reference to FIGS. 1-11. As explained above, the parallel hierarchical design technique uses a centralized BRP 102 and an HP2 computing architecture 140 to process many different business models, spatial arrangements, and systems integration designs in parallel and in a hierarchical fashion that maintains design dependencies. An embodiment of a technique for generating a systems integration design from a set of customer needs is now described in more detail with reference to FIG. 12. In particular, FIG. 12 is a process flow diagram of a computer-based technique for generating a systems integration design from a set of customer needs. The technique utilizes a highly iterative computer-based process loop 200 that relies on computationally intensive simulation, optimization, and verification operations performed by HP2 computing resources to implement a design process that heretofore has not been envisioned and could not have been accomplished using a conventional PC-based computer system and conventional building design processes, including discipline-specific proprietary databases.

At block 202, customer needs are specified. For example, the customer needs are specified through a user interface that queries a user to input customer needs according to a specific functional description. Examples of information processed at the customer needs domain have been described above.

At block 202, additional information such as information related to best practices, including building and/or operational flow, and building codes may be entered as part of the customer needs. For example, there may be location-specific and/or customer-specific best practices and building codes that should be incorporated into the design from the building inception. The customer needs (including best practices and building codes) are stored in the database as described above.

At block 204, at least one business model is generated in response to the customer needs. In an embodiment, the business model specifies what services the building is to offer and at what volume the services are to be offered. In the case of a customer looking to provide acute healthcare services to the residents of a particular ZIP code, the business model may define the type and volume of acute healthcare services that should be provided to meet anticipated demand. At block 206, the behavior of one or more of the business models is simulated. In an embodiment, a behavioral simulation uses workflow modeling to simulate how the specified services could be provided. For example, a simulation could compare people and process workflow patterns with space patterns to determine how a proposed business model would perform. The results of the behavioral simulations can be output in the form of performance metrics, for example, as graphs or ratings of such parameters as patient wait times, machine utilization, number of staff required, staff utilization, space utilization, energy efficiency, etc. Various different parameters can be used to evaluate the desirability of business models based on the behavioral simulation.

At block 208, the results of the behavioral simulations can be evaluated to see if the customer needs have been met. This can be a manual process, which includes direct human interaction, an automatic process (no human interaction), which is based on preprogrammed criteria, or a combination thereof. At block 210, it is also possible to modify the customer needs and/or the business model. A modification of the customer needs and or business model can be propagated downstream in the flow, including for example, the behavioral simulation.

At block 212, once the behavioral simulation has shown that a particular business model meets the customer needs, the business model can be put through a computer-based optimization process. For example, the computer-based optimization process can run through a large number of design alternatives to optimize certain aspects of the building design. In an embodiment, an optimization process attempts to optimize areas of importance that are specified in the customer needs. For example, if the customer needs place a high value on worker convenience, then designs that minimize worker walking distances may be favored. Likewise, if the customer needs place a high value on energy efficiency, then designs that minimize the need for artificial light and HVAC may be favored. Other criteria for optimization may include Return on Investment (ROI), capital expense operating expense, patient wait time, or any combination thereof.

In a complex building system such a hospital, the customer needs will specify a wide range of design priorities that can only be optimized through a multidimensional analysis of a large number of design variables. The multidimensional analysis of a large number of design variables is computationally processed by the HP2 computing resources as described with reference to FIG. 2.

Once a business model has been optimized, at block 214, the optimized business model is put through a validation process. The validation process checks to see if a particular business model meets particular design rules (e.g., design rule checking) and/or to see if the business module meets the specified customer needs. The process of generating a new business model (or modifying an already existing business model), behaviorally simulating the new business model, optimizing the new business model, and validating the new business model, can be run through multiple iterations before the design moves to the spatial arrangement domain.

At block 216, each validated business model can be used as input to generate one or more spatial arrangements. As described above, a spatial arrangement may specify the form and shell of a building system, the block and stack arrangement of the building system, and the room placement. The spatial arrangement may be simulated and/or optimized as described using the HP2 computing resources. At blocks 218 and 220, the spatial arrangement can be processed through an iterative process of verification and modification. For example, the verification operation may involve design rule checking and the modification may involve adjusting one or more parameters of the spatial arrangement.

At block 222, each verified spatial arrangement can be used as input to generate one or more systems integration designs. As described above, the systems integration design may specify the 3D spaces and infrastructure of the building system. In the systems integration domain, the systems integration design may be simulated and optimized as desired using the HP2 computing resources. At blocks 224 and 226, the spatial integration design can be processed through an iterative process of verification and modification. For example, the verification operation may involve design rule checking and the modification may involve adjusting one or more parameters of the systems integration design. The output of the systems integration design can be used to implement operations in the manufacturing, assembly, commissioning, and operation domains as represented by blocks 228, 230, 232, and 234, respectively.

Figure 13:
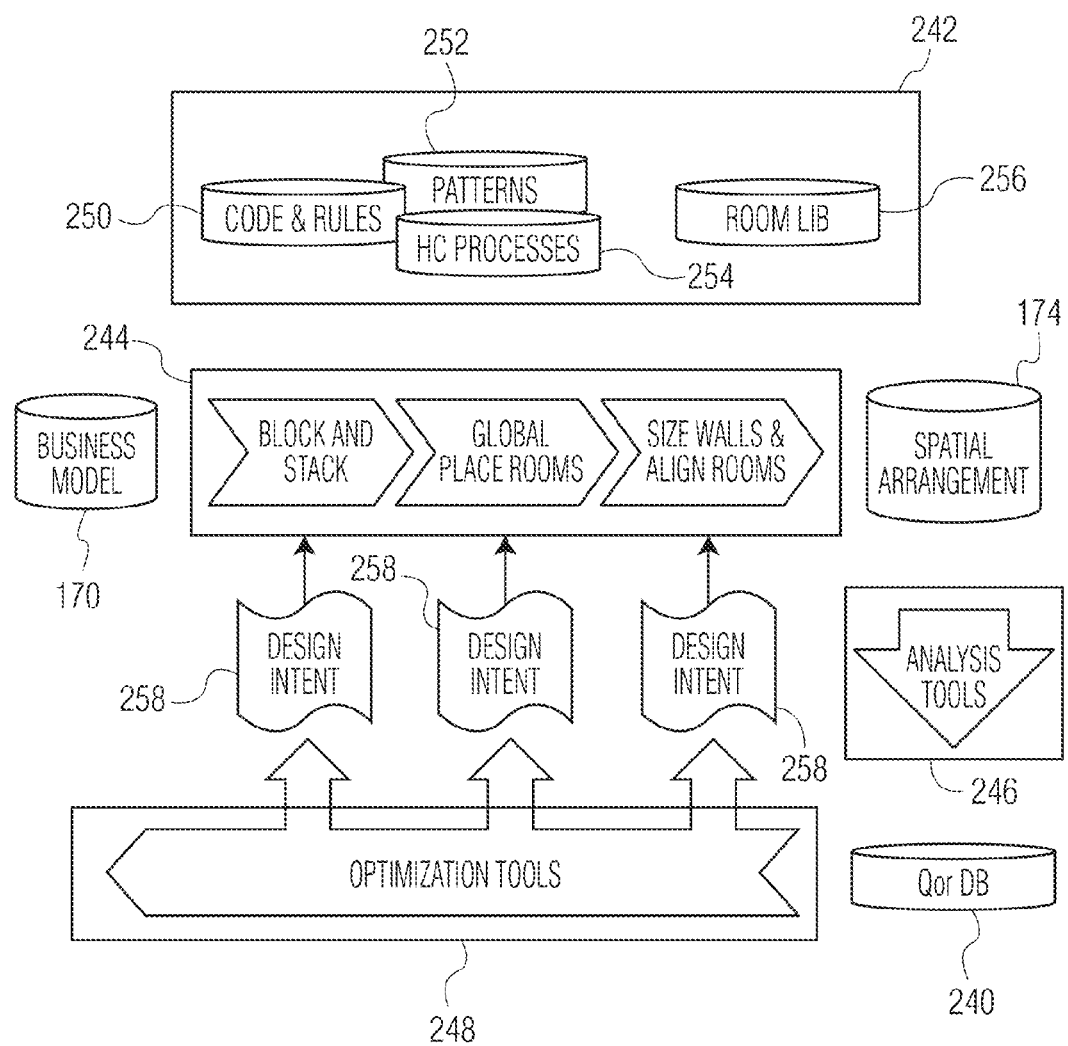
FIG. 13 illustrates system elements and a corresponding process flow for generating a spatial arrangement from a business model using the building realization platform.

FIG. 13 illustrates system elements and a corresponding process flow for generating a spatial arrangement from a business model using the BRP 102. The system elements include at least one of the business model databases 170, at least one of the spatial arrangement databases 174, an analysis database 240, a building design knowledge base 242, synthesis tools 244, analysis tools 246 (e.g., simulation and/or validation), and optimization tools 248. In the building design knowledge base, a codes and rules element 250 includes building codes and building design rules, a patterns element 252 includes a pre-established set of design patterns (e.g., architectural patterns or architectural partis), a healthcare (HC) processes element 254 includes healthcare process workflow rules, and a rooms library 256 includes a pre-established set of rooms that have certain physical and/or operational characteristics. In operation, the information from the business model is processed by the synthesis tools to generate one or more spatial arrangements. The synthesis tools use information from the building design knowledge base and design intent 258 (e.g., design criteria) to generate a spatial arrangement. The spatial arrangement can then be analyzed (e.g., simulated and/or validated) as desired and the results of the analysis are stored in the analysis database. The optimization tool can be used to change parameters of the design intent (e.g., the orientation of the building (see FIG. 7) or the number of rooms per wing or the nurse ratio (see FIG. 9)), which are then propagated through the synthesis tools to generate optimized spatial arrangements.

Although the BRP 102 has been described above in the context of a healthcare building such as a hospital, the above described BRP and associated techniques are applicable to other buildings and building systems. For example, the BRP and associated techniques may be applicable to hospitality buildings (e.g., hotels), apartment/condominium buildings, and transportation facilities (e.g., airports). Additionally, a building system may include one or more buildings that can be detached from each other, partially attached to each other, or fully attached to each other. For example, a building system may be a building or a set of buildings that are located at the same physical site/location and that are intended to fulfill a set of customer needs.

Figure 14:
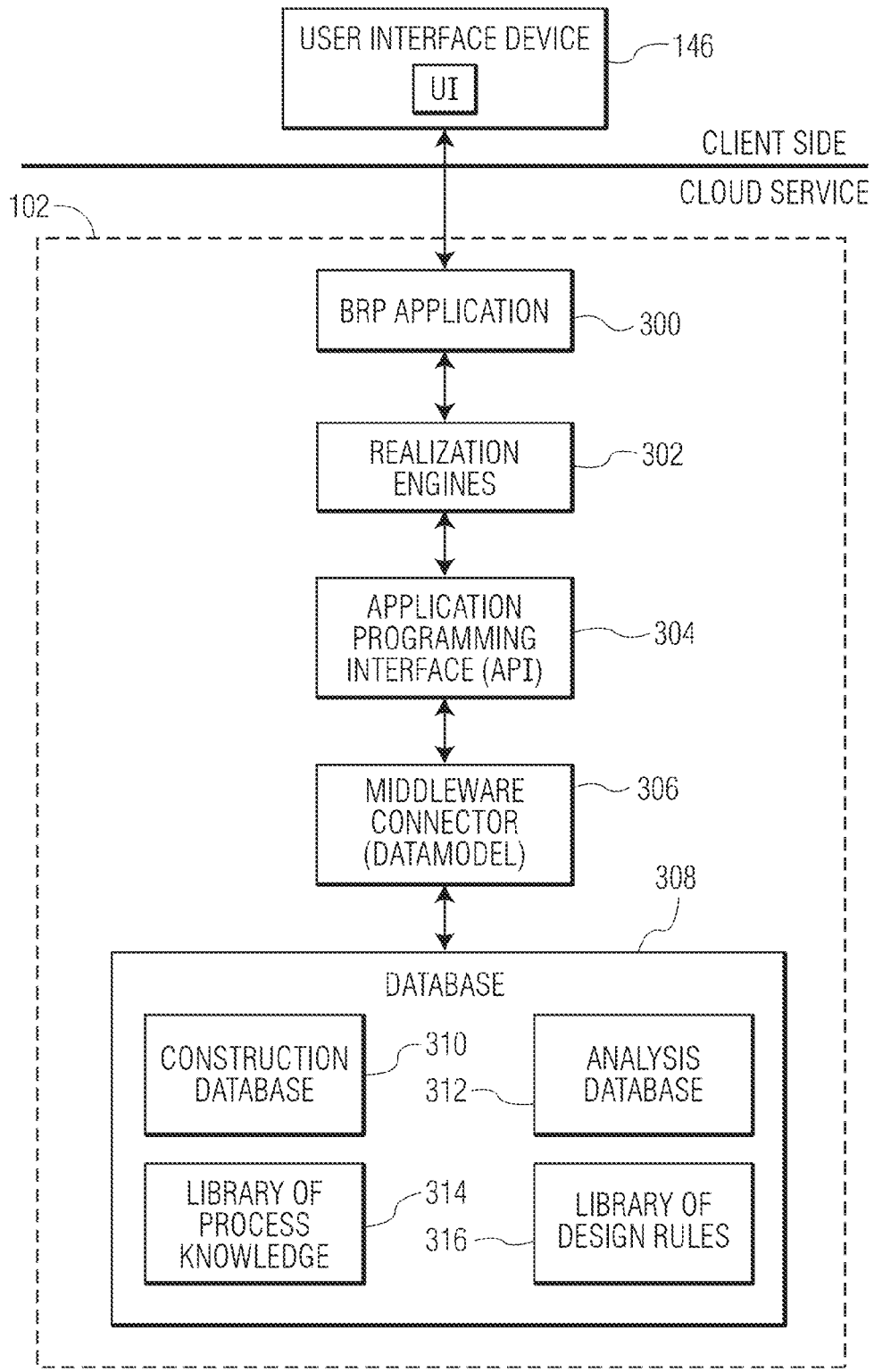
FIG. 14 illustrates an embodiment of the architecture of an embodiment of the building realization platform.

FIG. 14 illustrates an embodiment of the architecture of an embodiment of the BRP relative to a user interface device 146 on a client side of a network and a cloud service from which the BRP 102 is implemented. As depicted in FIG. 14, the BRP includes a BRP application 300, realization engines 302, an application programming interface (API) 304, a middleware connector 306, and a database 308. In an embodiment, the realization engines provide the design, modeling, simulation, optimization, and verification services of the BRP and the BRP application provides the logic that allows the user of the client device to communicate with and control, via a user interface, the services that are provided by the realization engines. The API provides the logic to enable the realization engines to obtain data from and provide data to the database. The middleware connector provides an abstraction layer between the realization engines and the database. The database stores data related to the design, modeling, simulation, optimization, and verification of building systems. In the embodiment of FIG. 14, the database includes a construction database 310, an analysis database 312, a library of process knowledge 314, and a library of design rules 316 although the data in the database can be organized in other ways. In an embodiment, the computer readable instructions necessary to implement the BRP application, the realization engines, the API, and the middleware connector and the data in the database are stored in servers of the cloud service. When called upon for execution, the instructions and corresponding data are processed by processors of the cloud service as described above.

Figure 15:
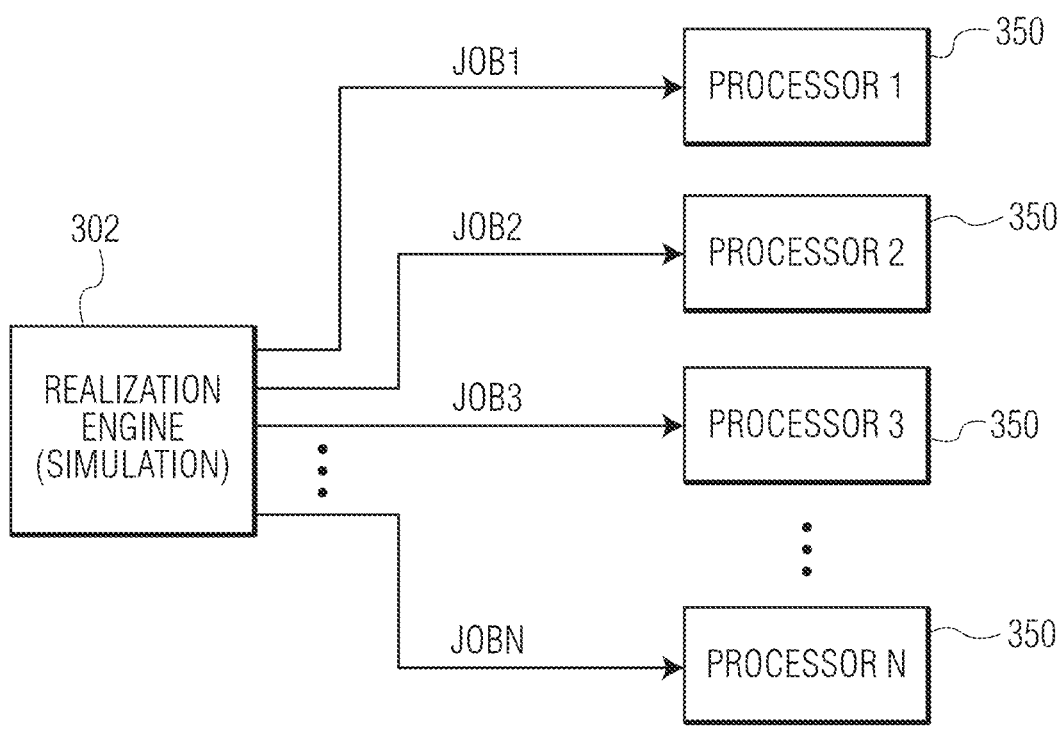
FIG. 15 illustrates the execution of a service that is provided by one of the realization engines.

FIG. 15 illustrates the execution of a service that is provided by one of the realization engines 302. For example, the service is a simulation that involves distributing a set of computational tasks amongst a large number of physically distinct processors or separate processing cores. As shown in FIG. 15, N different computational tasks related to the same simulation operation are distributed amongst N different processors 350, where N is, for example, in the range of 100-1,000. As described above, the processors may be provided through a cloud service and used only on an as needed basis.

In an embodiment, the BRP 102 allows the generation and optimization of a virtual building based on user needs and a comprehensive set of rules including building codes and best practices in the corresponding industries. Users create virtual buildings using a design flow that morphs the design gradually from a very abstract description (for example, serve an area defined by a set of ZIP codes with enough acute care capacity to satisfy demand) to a fully detailed description containing architectural intent, engineering details, and construction details that leave no ambiguity as to how the building should be built and how the building system will perform. Once a virtual building is complete within the BRP, detailed operation and construction documents can be generated by the BRP in various industry standard formats. In an embodiment, a virtual building system maintained by the BRP contains detailed information about the building and all its subsystems, and about its use and its performance along many dimensions such as operating costs, construction costs, thermal comfort level, daylight usage, sustainability, operational efficiency, patient experience. The virtual building system maintained by the BRP is detailed and accurate enough that it can be used to unambiguously generate detailed construction documents for the construction of a real building system having a performance that matches the performance of the virtual building system.

In an embodiment, the virtual building system that is maintained by the BRP can be used to predict the implications of changes during the lifetime of the building. In an embodiment, the virtual building system includes descriptions of: the building structure; the processes and service lines, the mechanical, electrical, plumbing (MEP) subsystems; the information technology (IT) subsystem; the thermal/energy behavior; the seismic behavior; the light behavior; and the sound behavior. In an embodiment, the virtual building system maintained in the BRP differs from current practices in the following ways: Besides the description of the physical building, the virtual building system also includes the description of the purpose and operation of the building as both the building and the processes need to be designed and measured together. The information about the building is partitioned differently. Traditionally, information is grouped per domain (building structure, mechanical system, electrical system) with a loose coupling between various domains. This is done because the toolsets for the different domains differ and because the domain-specific information resides with different companies. Here, information of all domains is grouped by sequence in which design decisions are made and information becomes available. Unlike current building information modeling (BIM) practices, where the overall architecture is a federated network of isolated systems, each holding a part of the golden design information and exchanging a minimum information with each other using standard protocols on a need basis, the approach described herein is a star configuration where different systems communicate exclusively through the BRP. The golden design information resides in a central database and the satellite systems are used as agents that change the central golden information and report back.

Figure 16:
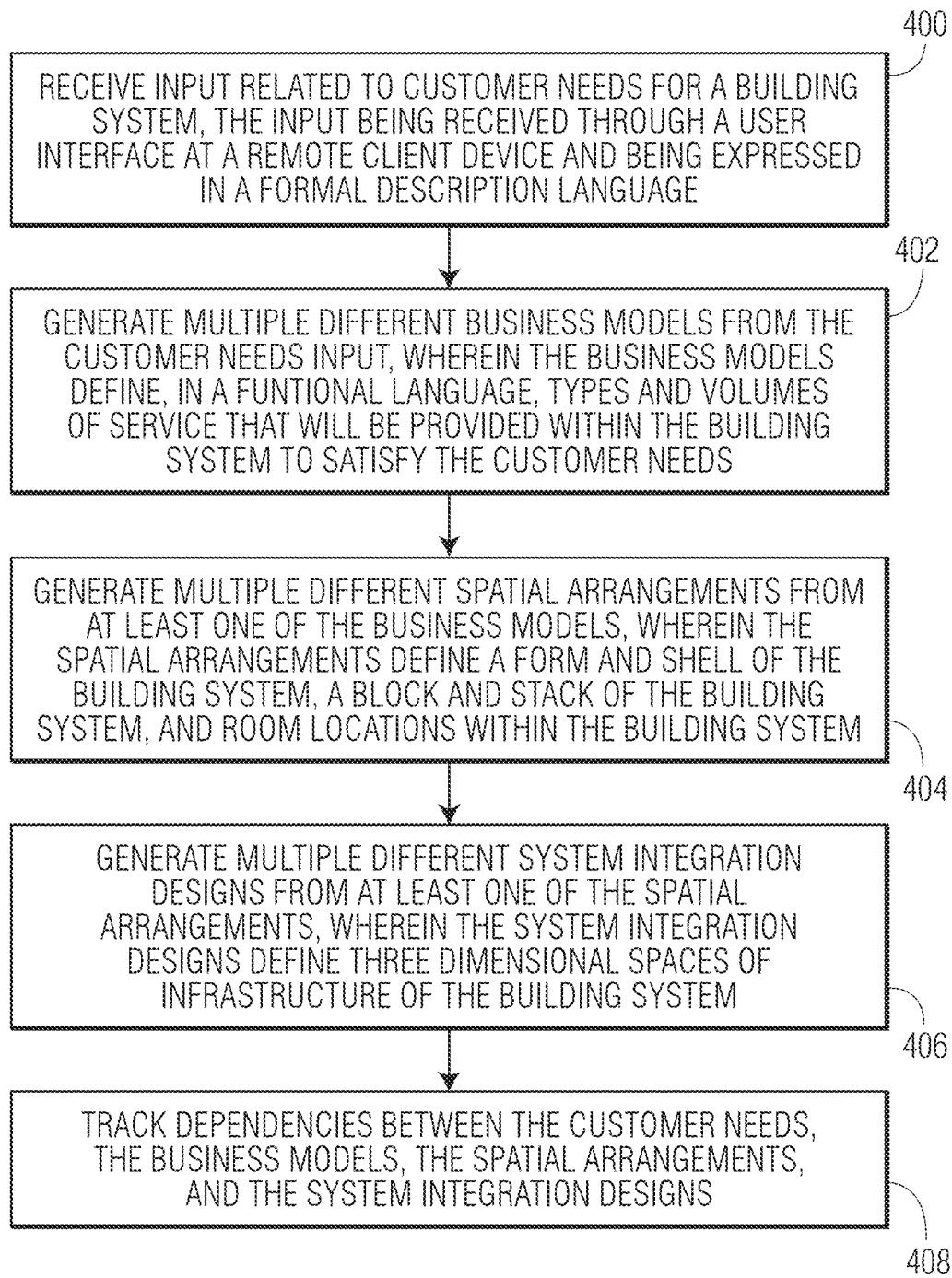
FIG. 16 is a process flow diagram of a method for realizing a complex building system.

FIG. 16 is a process flow diagram of a method for realizing a complex building system. At block 400, input related to customer needs for a building system is received, the input being received through a user interface at a remote client device and being expressed in a formal description language. At block 402, multiple different business models are generated from the customer needs input, wherein the business models define, in a functional language, types and volumes of services that will be provided within the building system to satisfy the customer needs. At block 404, multiple different spatial arrangements are generated from at least one of the business models, wherein the spatial arrangements define a form and shell of the building system, a block and stack of the building system, and room locations within the building system. At block 406, multiple different systems integration designs are generated from at least one of the spatial arrangements, wherein the systems integration designs define three dimensional spaces of infrastructure of the building system. At block 408, dependencies are tracked between the customer needs, the business models, the spatial arrangements, and the systems integration designs.

Figure 17:
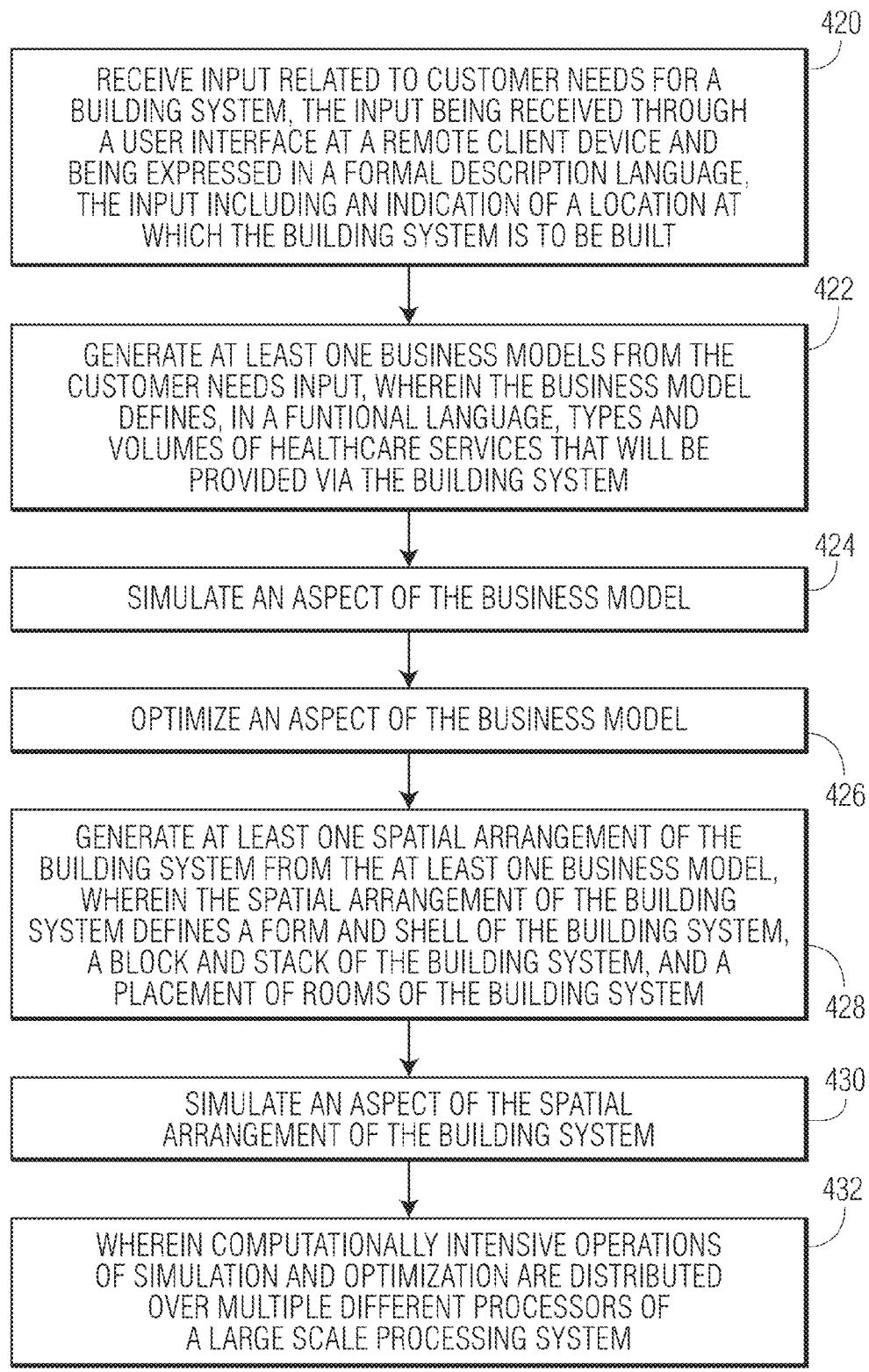
FIG. 17 is a process flow diagram of a method for realizing a building system within which healthcare services will be provided to patients.

FIG. 17 is a process flow diagram of a method for realizing a building system within which healthcare services will be provided to patients. At block 420, input related to customer needs for a building system is received, the input being received through a user interface at a remote client device and being expressed in a formal description language, the input including an indication of a location at which the building system is to be built. At block 422, at least one business model is generated from the customer needs input, wherein the business model defines, in a functional language, types and volumes of healthcare services that will be provided via the building system. At block 424, an aspect of the business model is simulated. At block 426, an aspect of the business model is optimized. At block 428, at least one spatial arrangement of the building system is generated from the at least one business model, wherein the spatial arrangement of the building system defines a form and shell of the building system, a block and stack of the building system, and a placement of rooms of the building system. At block 430, an aspect of the spatial arrangement of the building system is simulated. At block 432, the computationally intensive operations of simulation and optimization are distributed over multiple different processors of a large scale processing system.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods may be implemented using software instructions stored on a non-transitory computer useable storage medium for execution by a computer. As an example, an embodiment of a computer program product includes a computer useable storage medium to store a computer readable program that, when executed on a computer, causes the computer to perform operations, as described herein.

Furthermore, embodiments of at least portions of the invention can take the form of a computer program product accessible from a computer-usable or non-transitory computer-readable medium providing computer executable instructions, or program code, for use by or in connection with a computer or any instruction execution system. For the purposes of this description, a non-transitory computer-usable or computer readable medium can be any apparatus that can contain or store the program for use by or in connection with the instruction execution system, apparatus, or device.

The computer-useable or computer-readable medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Figure 18:
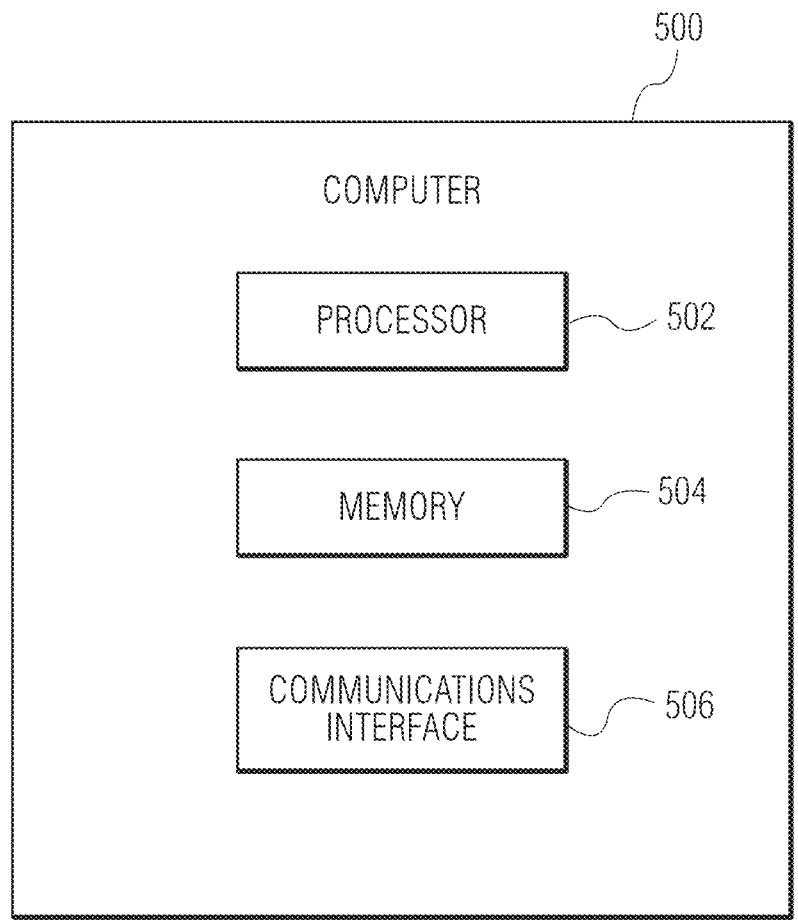
FIG. 18 depicts a computer that includes a processor, memory, and a communications interface.

In an embodiment, the above-described functionality is performed by a computer or computers, which executes computer readable instructions. FIG. 18 depicts a computer 500 that includes a processor 502, memory 504, and a communications interface 506. The processor may include a multifunction processor and/or an application-specific processor. Examples of processors include the PowerPC™ family of processors by IBM and the x86 family of processors by Intel such as the Xeon™ family of processors and the Intel X5650 processor. The memory within the computer may include, for example, storage medium such as read only memory (ROM), flash memory, RAM, and a large capacity permanent storage device such as a hard disk drive. The communications interface enables communications with other computers via, for example, the Internet Protocol (IP). The computer executes computer readable instructions stored in the storage medium to implement various tasks as described above.

As described above, the business model (BM) domain produces certain outputs, such as the building square footage needed to provide the desired services, which are used within the spatial arrangement (SA) domain to define certain aspects of the building system. For example, within the spatial arrangement domain certain physical aspects of the building system are defined, including the building "form and shell," the building "block and stack," and the room placement.

The building system "form and shell" can also be referred to as the "building massing configuration." As used herein, the building massing configuration is at least partially defined by the footprint shape of the building system, the footprint dimensions, and the number of floors of the building.

In reality, there is almost an infinite number of different building massing configurations that can be employed to meet the needs of a particular business model. That is, multiple different building massing configurations can support the desired use of the building, e.g., types and volume of services to be provided within a healthcare building system. Although multiple different building massing configurations may meet the needs of a particular business model, the massing configuration of a building has an effect on energy use. For example, a long and narrow building massing configuration will have more exposed surface area than a square building of the same square footage. Among many factors, the differences in exposed surface area can have a large effect on the cost to heat and/or cool the building. Therefore, it is desirable to be able to evaluate many different building massing configurations in terms of energy efficiency, e.g., the energy use of the building, in order to intelligently select a building massing configuration.

The energy use of a building can be characterized by running an energy use simulation. Various computer-based energy use simulation programs are available, including for example, Building Loads Analysis and System Thermodynamics (BLAST), DOE-2, eQUEST, ESP-r, and EnergyPlus. A widely accepted energy use simulation program is the U.S. Department of Energy's EnergyPlus simulation program. EnergyPlus takes into consideration a large list of parameters to simulate the energy use of a building. Parameters considered in an EnergyPlus simulation may include, for example, information about the building site, climate information, building construction specifics, building operating schedules, operating loads, and building massing configuration. Some specific examples of simulation parameters include location coordinates, climate information, operating schedules, surface construction elements, thermal zone description/geometry, advanced surface concepts, detailed ground heat transfer, room air modules, internal gains (people, lights, other internal zone equipment), daylighting, exterior energy use equipment, and airflow. A detailed description of EnergyPlus input and output data can be found in the document "Input Output Reference: The Encyclopedic Reference to EnergyPlus Input and Output," Oct. 6, 2012, which is incorporated by reference herein.

As the complexity of a building increases, the computational requirements of an energy simulation also increase. For example, an EnergyPlus simulation of a four-story 250,000 square foot building of average complexity can take a single processor computer on the order of 2-8 hours to complete, e.g., model, setup, and run time. The computing power and time required to run EnergyPlus simulations can make it impractical to evaluate a large number, e.g., 10,000-30,000, of different building massing configurations early on in the building design process. Without a way to efficiently evaluate the energy use of a large number of building massing configurations, some desirable massing configurations may never come to the fore in the design process. Therefore, there is a need to be able to quickly evaluate the energy use of a large number, e.g., 10,000-30,000, of different building massing configurations early on in the design process so that energy use, and hence energy efficiency, can be integrated into the building design process.

In accordance with an embodiment of the invention, formulas are derived in advance for calculating the energy use of different building massing configurations so that a large number of different building massing configurations can be quickly evaluated for energy efficiency early on in the building design process. In an embodiment, the formulas are a function of a limited set of parameters that are directly related to the building massing configuration. For example, the formulas are a function of the shape of the building footprint, the dimensions of the building, and the number of stories of the building. Because the formulas are a function of a limited set of parameters, the energy use of a large number of building massing configurations can be quickly calculated for energy use evaluation early on in the design process. Additionally, the formulas are normalized to a reference building such that the energy use of each different building massing configuration is compared to the same standard, e.g., the reference building.

Given a set of building design parameters, the predefined and normalized formulas are used in, for example, the Building Realization Platform (BRP) to calculate the energy use of multiple different building massing configurations so that the multiple different building massing configurations can be compared to each other in terms of energy use. As an example, using the techniques that are described in more detail below, energy use indexes of over 20,000 different building massing configurations can be calculated in less than one minute. The energy use information can then be intelligently searched and sorted to identify desirable building massing configurations. An embodiment of a technique for characterizing the energy use of multiple different building massing configurations is described below with reference to FIGS. 19a-28.

In an embodiment, a technique for characterizing the energy use of multiple different building massing configurations is based on building dimensions that are a function of a fixed size bay, where a bay defines at least a floor portion of the building. Accordingly, the footprint of each building is established by a set of adjoining fixed size bays. In an embodiment, each fixed size bay is a 30'×30' square. Although a 30'×30' square bay is described, other shapes and dimensions of a fixed size bay are possible. Given 30'×30' fixed size bays, the footprint shape of each story of a building is a function of the 30'×30' bays and can only be changed by 30' increments.

Figure 19A:
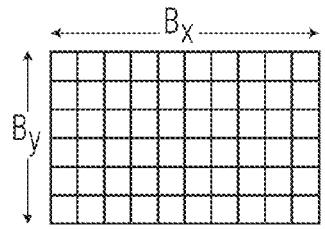
FIGS. 19a-19i depict nine different predefined building footprint shapes.
Figure 19B:
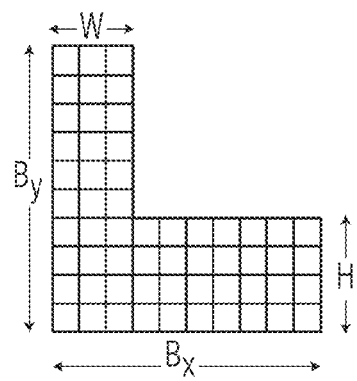
Figure 19C:
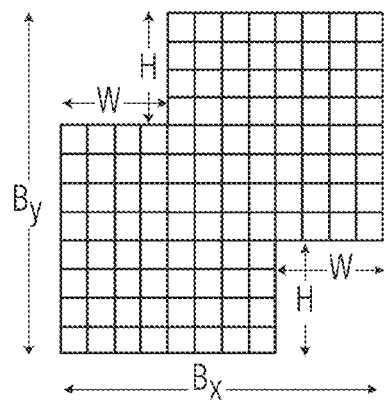
Figure 19D:
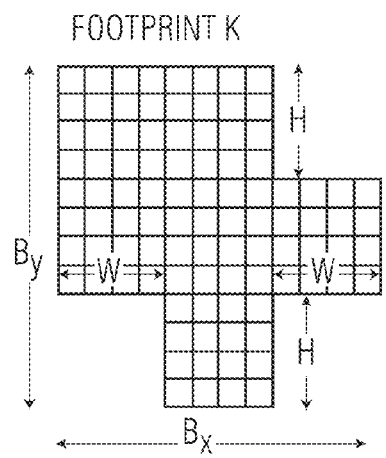
Figure 19E:
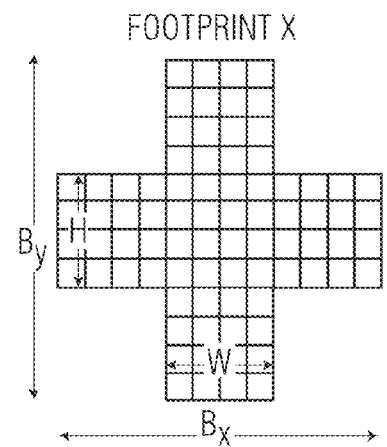
Figure 19F:
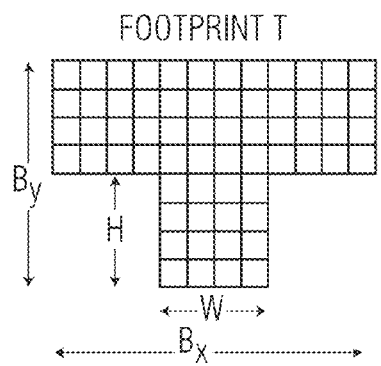
Figure 19G:
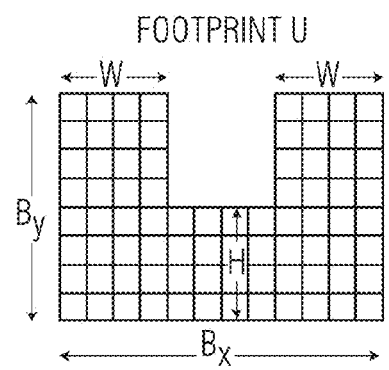
Figure 19H:
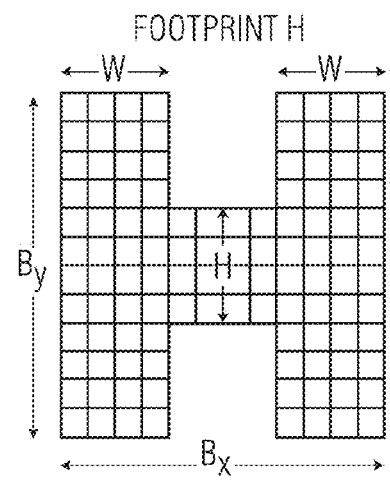
Figure 19I:
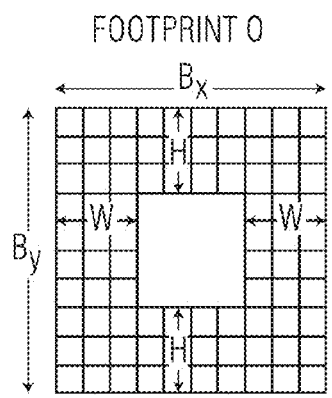

Using fixed size bays, multiple different footprint shapes can be produced. In accordance with an embodiment of the invention, a limited number of footprint shapes have been predefined for use in characterizing energy use. Each footprint shape is formed from the fixed size bays and the footprint shapes can be selected in view of, for example, known footprint shapes and/or commonly used architectural parti. For example, the footprint shapes are footprint shapes that have practical application to healthcare buildings. FIGS. 19a-19h depict nine different predefined footprint shapes, including footprint shape R (FIG. 19a), footprint shape L (FIG. 19b), footprint shape Z (FIG. 19c), footprint shape K (FIG. 19d), footprint shape X (FIG. 19e), footprint shape T (FIG. 19f), footprint shape U (FIG. 19g), footprint shape H (FIG. 19h), and footprint shape O (FIG. 19i). Although some footprint shapes are shown, other footprint shapes are possible. As shown in FIGS. 19a-19i, each footprint shape has been given a "shape name" for identification purposes. The set of shape names defines a shape alphabet, which is represented as: R, L, Z, K, X, T, U, H, O. With reference to FIGS. 19a-19i, dimensions of the footprint shapes are identified as Bx, By, W, and H, where:

Bx—bounding box dimension on the x-axis in number of bays;

By—bounding box dimension on the y-axis in number of bays;

W—void area width dimension in number of bays; and

H—void area height dimension in number of bays.

As used herein and shown in FIGS. 19a-19i, the bounding box dimensions represent the dimensions of a box defined by the maximum x-axis and y-axis dimensions, and the void area dimensions W and H are specific to each footprint shape.

Figure 20:
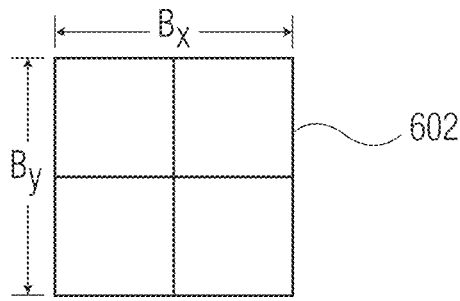
FIG. 20 depicts the footprint shape of a reference building.

A technique for characterizing the energy use of multiple different building massing configurations is now described in terms of the fixed size bay and the predefined set of footprint shapes. A first step involves modeling the energy use of a reference building. In an embodiment, the building massing configuration of the reference building is defined as a square building that has a 2-bay×2-bay footprint and three stories. FIG. 20 depicts the footprint shape 602 of the reference building and the building massing configuration of the reference building is defined as:

Bx=2;

By=2;

W=0;

H=0; and

Ns=3, where Ns is the number of stories.

Given a 30'×30' fixed size bay, the reference building is a 60'×60' square that is three stories high.

With the building massing configuration of the reference building defined, the energy use of the reference building is calculated. In accordance with an embodiment of the invention, the energy use of the reference building is calculated on an energy use per annum, per square foot basis, which is referred to herein as the energy use index (EUI). A process for calculating the energy use index, EUI, of the reference building is described with reference to FIG. 21. The process uses the EnergyPlus simulation program to calculate the total energy use of the reference building per annum and then divides the total energy use by the total square footage of the reference building to come up with an energy use index for the reference building, EUI-RB.

Figure 21:
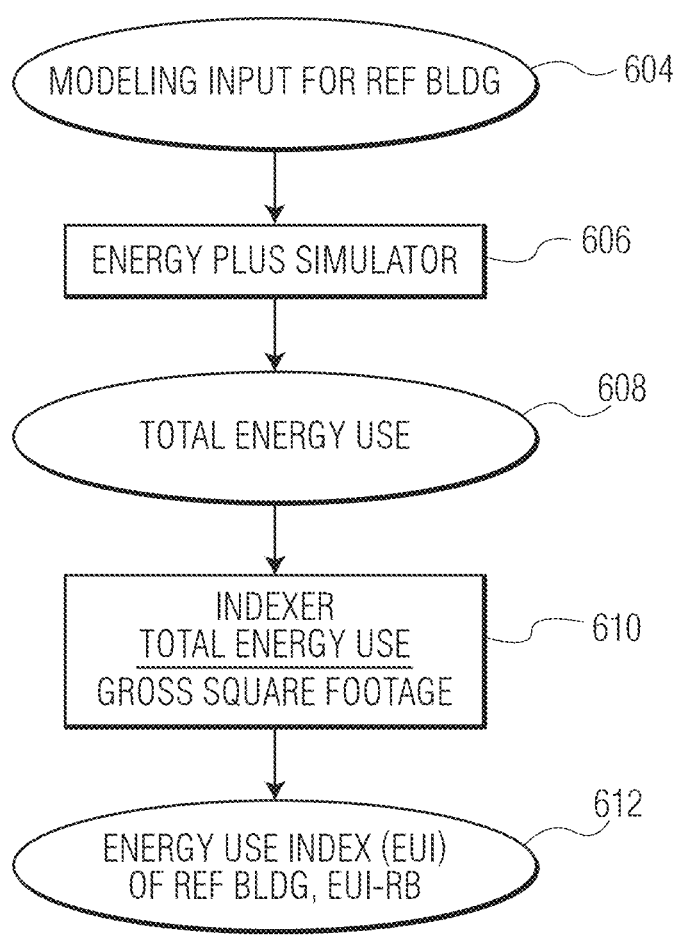
FIG. 21 illustrates an embodiment of a process for calculating the energy use index, EUI, of the reference building.

With reference to FIG. 21, a modeling input 604 is generated for the reference building. The modeling input includes building massing configuration information and other information as required by the EnergyPlus program. For example, the modeling input may be presented in an EnergyPlus input file (IDF) that also defines the simulation parameters. A number of tools are available to create EnergyPlus input files. These include, for example, Easy EnergyPlus, ECOTECT, EnergyPlugged, EP-GEO & EP-SYS, EP-QUICK, ESP-r, jEPlus, and EP-Launch. Other techniques may also be used to create EnergyPlus input files. One technique for creating simulation input filed, e.g., EnergyPlus input files, is described below.

Once the modeling input 604 is established, it is provided to an EnergyPlus simulator 606, which runs an EnergyPlus simulation to determine the total energy use 608 of the reference building. For example, the total energy use is calculated on in a per annum basis and it may be in the range of 20-40 GWh/annum for a 250,000 square foot building that delivers healthcare services. The total energy use is then provided to an indexer 610 to calculate the energy use index of the reference building, EUI-RB, 612. The energy use index of the reference building, EUI-RB, can be expressed as:

EUI-RB=total energy use per annum/gross square footage

The energy use index of the reference building is used as described below to normalize the simulation results for multiple different building massing configurations.

As explained above with reference to FIGS. 19a-19i, energy use is characterized with respect to a predefined set of footprint shapes. A next step in the process involves modeling the energy use of buildings that utilize each of the different pre-defined footprint shapes, referred to herein as shape-specific modeling. In accordance with an embodiment of the invention, the energy use of multiple different building massing configurations is simulated for each different footprint shape and the results are used to generate a normalized energy use index, nEUI, for each different building massing configuration.

Figure 22:
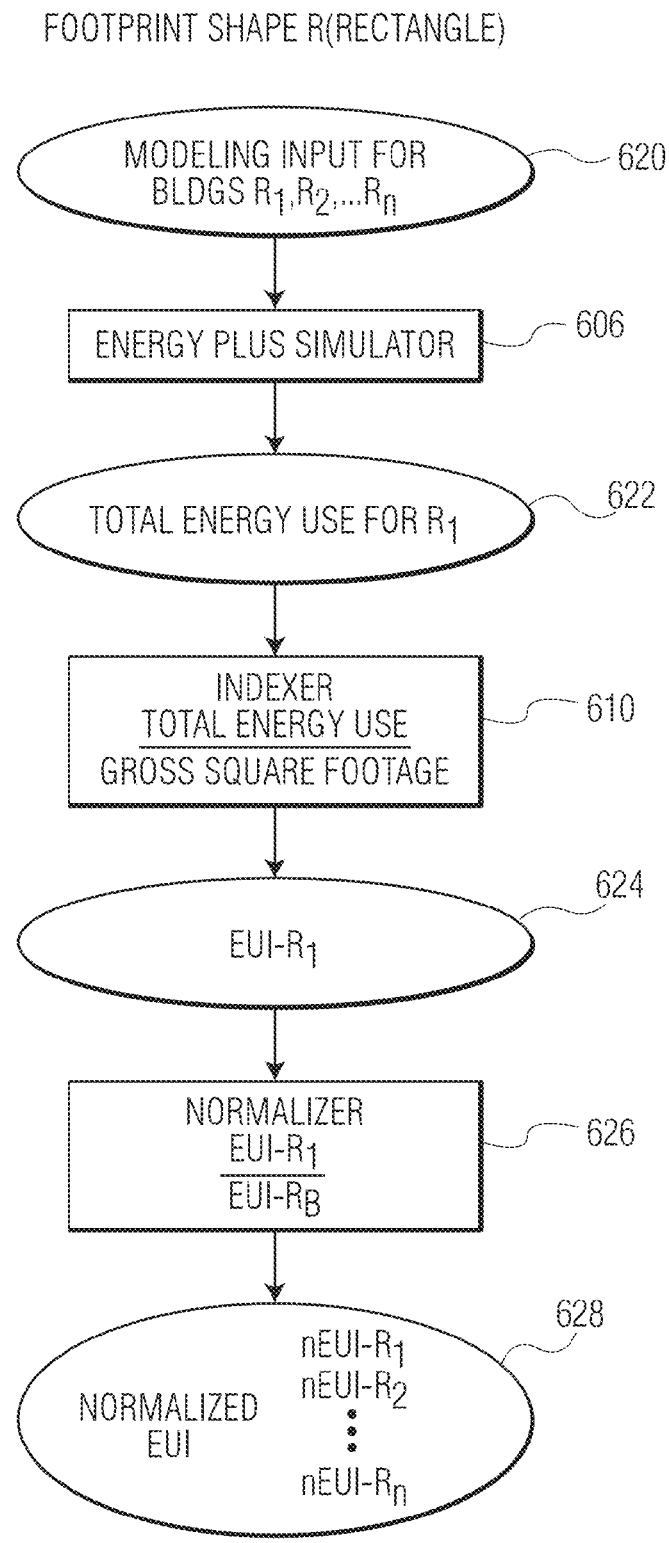
FIG. 22 illustrates an embodiment of a process for generating normalized energy use indexes, nEUIs, for buildings having the footprint shape R.

A process for generating normalized energy use indexes, nEUIs, for buildings having the footprint shape R is described with reference to FIG. 22. A first step in the process involves establishing the modeling input 620 for an EnergyPlus simulation. In an embodiment, the modeling input includes a set of building massing configurations in which each instance of a configuration has a different combination of configuration parameters, e.g., Bx, By, and Ns, but the same footprint shape. Note that for footprint shape R, the void area dimensions W and H are not relevant (e.g., essentially W=0 and H=0) and as described above, the values of Bx and By represent increments of the 30'×30' fixed size bay. As shown in FIG. 22, each different shape-specific building massing configuration has a unique identifier, e.g., $R_1, R_2, \ldots R_n$.

In an example, the number of different shape-specific building massing configurations (e.g., where a shape-specific building massing configuration is defined by a unique set of Bx, By, W, H, and Ns) that are established as inputs is on the order of thousands, e.g., 1,000-5,000 per footprint shape. For example, the number of different shape-specific building massing configurations is a function of the range of possible values for Bx, By, W, H, and Ns, where the range of possible values for Bx, By, W, H, and Ns is selected to reflect the possible range of building massing configurations that are to be evaluated. The total number of different shape-specific building massing configurations can be expressed as:

Total number=$Bx \times By \times W \times H \times Ns$

Given these five degrees of variability, the number of different shape-specific building massing configurations grows rapidly for each footprint shape. For example, with the following ranges set at; $1 \leq Bx \leq 7$, $1 \leq By \leq 6$, $0 \leq W \leq 5$, $0 \leq H \leq 6$, $1 \leq Ns \leq 4$, the total number of different shape-specific building massing configurations for a particular footprint shape is calculated as:

$7 \times 6 \times 6 \times 7 \times 4 = 7,056$

A technique for generating and managing building massing configurations is described in more detail below. In an embodiment, sets of building massing configurations are pre-generated for each footprint shape and stored in a building massing configuration library, or "massing library." For example, the massing library includes building massing configurations, also referred to as design patterns, architectural patterns, or architectural partis, as described with reference to FIG. 13 and patterns element 252.

For each different building massing configuration, the modeling input 620 includes the building massing configuration and other information that is required by the EnergyPlus simulator. For example, the modeling input may be provided in an IDF file that defines the EnergyPlus simulation parameters. With the modeling input established and provided to the EnergyPlus simulator 606, EnergyPlus simulations are run for each different building massing configuration. The EnergyPlus simulations can be run, for example, in series on a single processor machine, in parallel on a multiprocessor machine, or in parallel using HPHP computing resources as described above with reference to FIG. 2. In one implementation, it is estimated that it would take approximately 40 days to run 900 different EnergyPlus simulations serially on a single processor machine, approximately 2.5 days to run the same 900 EnergyPlus simulations in parallel on a 16 processor Linux server, and approximately 8 hours to run the same 900 EnergyPlus simulations using HPHP computing, e.g., using 50 dual-processor nodes of a cloud computing resource such as Amazon Web Services (AWS). As with the reference building, the total energy use is calculated on, for example, a per annum basis and may be in the range of 1-2 GWh/annum. Referring again to FIG. 22, upon completion of an EnergyPlus simulation, the total energy use 622 for each building massing configuration, e.g., $R_1$, is provided to the indexer 610 to calculate the corresponding energy use index, e.g., EUI-$R_1$, 624. The energy use index of the building massing configuration is then provided to a normalizer 626, which normalizes the energy use index by dividing the shape-specific energy use index by the energy use index of the reference building. The normalized energy use index for the building massing configuration $R_1$ can be expressed as:

nEUI-R1=EUI-R1/EUI-RB

The operations of energy use simulation, indexing, and normalizing are performed for each of the different shape-specific building massing configurations, e.g., $R_1, R_2, \ldots R_n$ to produce shape-specific normalized energy use indexes nEUI-$R_1$, nEUI-$R_2$, . . . nEUI-$R_n$, 628. The nEUI data is stored in a shape-specific database for further processing as described below.

Figure 23:
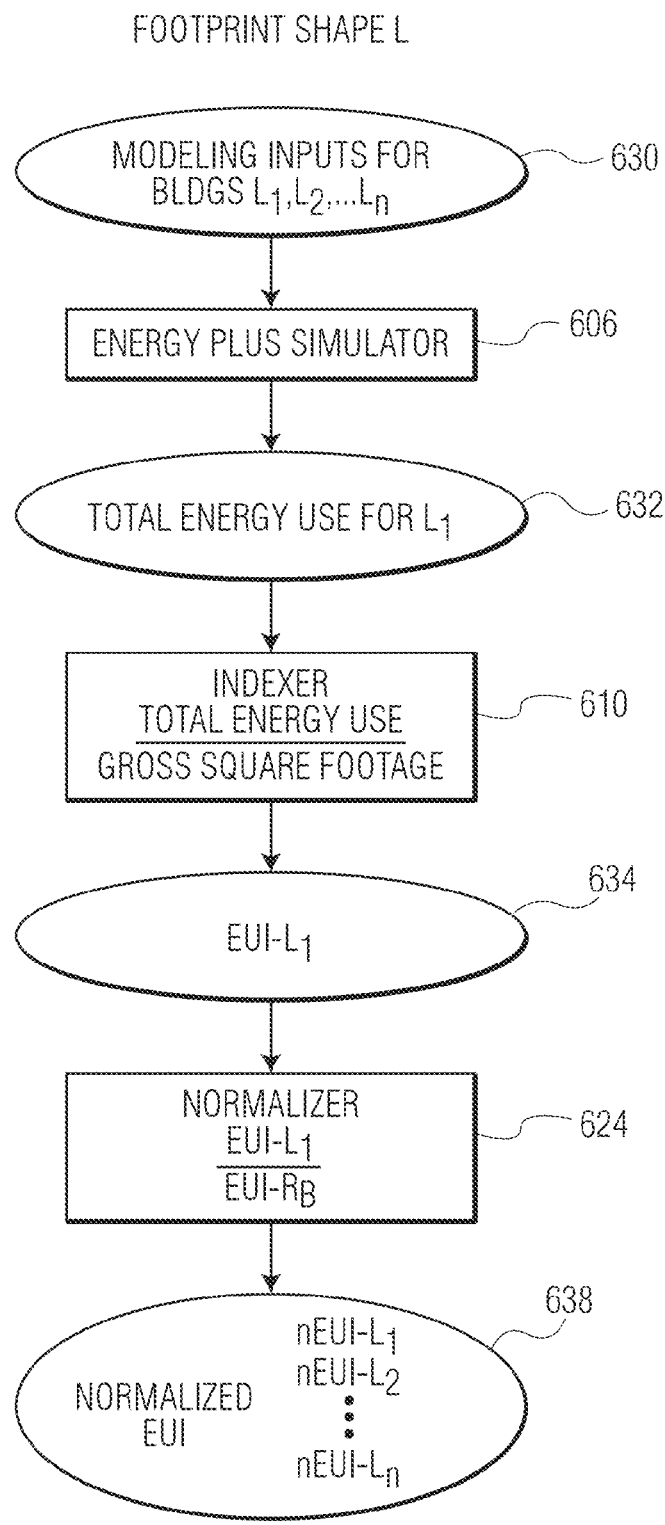
FIG. 23 illustrates an embodiment of a process for generating normalized energy use indexes for buildings having the footprint shape L.

The process described above is performed for each of the predefined shapes shown in FIGS. 19a-19i. FIG. 23 illustrates an embodiment of the process for generating normalized energy use indexes for buildings having the footprint shape L. In the example of FIG. 23, the number of different L-shaped building massing configurations is on the order of thousands, e.g., 1,000-5,000, as described above.

With reference to FIG. 23, for each different building massing configuration of the L-shaped footprint, the modeling input 630 includes the building massing configuration and other information that is required by the EnergyPlus simulator. With the modeling input established and provided to the EnergyPlus simulator 606, EnergyPlus simulations are run for each different building massing configuration to calculate the total energy use 632 on, for example, a per annum basis. Upon completion of an EnergyPlus simulation, the total energy use for each building massing configuration, e.g., $L_1$, is provided to the indexer 610 to calculate the corresponding energy use index, e.g., EUI-$L_1$, 634. The energy use index of the building massing configuration is then provided to a normalizer 624, which normalizes the energy use index by dividing the shape-specific energy use index by the energy use index of the reference building. The operations of energy use simulation, indexing, and normalizing are performed for each of the different L-shape building massing configurations, e.g., $L_1$, $L_2$, ... $L_n$ to produce shape-specific normalized energy use indexes nEUI-$L_1$, nEUI-$L_2$, ... nEUI-$L_n$, 638. The nEUI data is stored in a shape-specific database for further processing as described below.

Once the process of generating normalized energy use indexes for each footprint shape (e.g., R, L, Z, K, X, T, U, H, O) is completed, shape-specific formulas are derived from the normalized energy use index data. In an embodiment, formulas are derived that define the normalized energy use index, nEUI, as a function of a limited set of variables related to the building massing configuration. For example, the formulas define the shape-specific normalized energy use indexes, nEUI, as a function of the parameters; Bx, By, W, H, Ns, and in some cases θ, where θ is the angular orientation of the building, e.g., relative to magnetic north.

Figure 24:
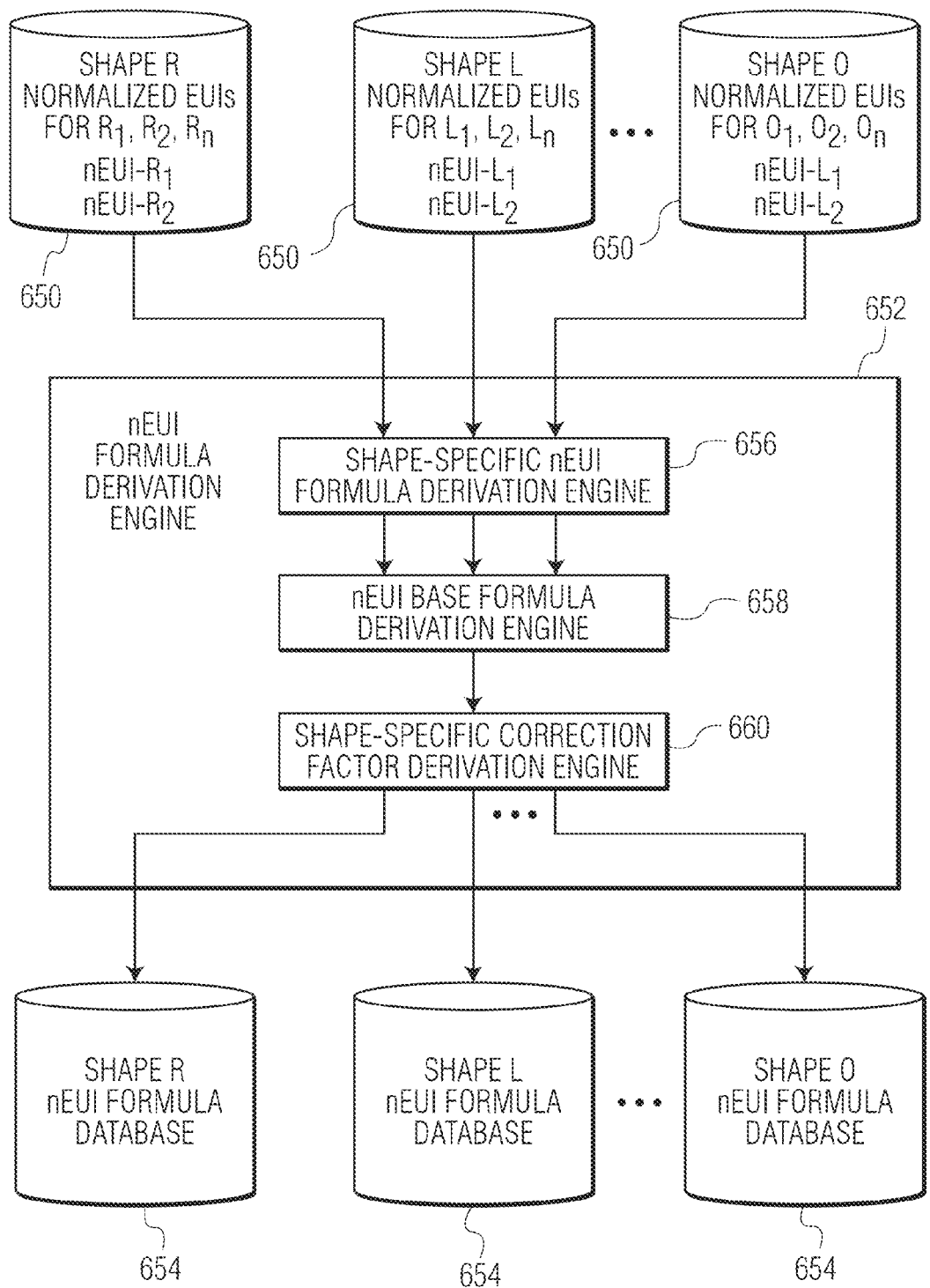
FIG. 24 illustrates an embodiment of a normalized energy use index derivation operation, which includes shape-specific nEUI databases, a normalized energy use index formula derivation engine, and shape-specific nEUI formula databases.

FIG. 24 illustrates an embodiment of the normalized energy use index derivation operation, which includes shape-specific nEUI databases 650, a normalized energy use index formula derivation engine 652, and shape-specific nEUI formula databases 654. In the embodiment of FIG. 24, the shape-specific nEUI databases 650 include a database for each different footprint shape and the shape-specific nEUI formula databases 654 include a database for each different footprint shape. The nEUI formula derivation engine 652 includes a shape-specific nEUI formula derivation engine 656, a nEUI base formula derivation engine 658, and a shape-specific correction factor derivation engine 660.

In a first operation, the shape-specific normalized energy use index data is used by the shape-specific nEUI formula derivation engine 656 to derive shape-specific formulas that best fit the corresponding data as a function of a limited set of variables, e.g., Bx, By, W, L, Ns, and θ. In an embodiment, a formula to represent nEUI for each footprint shape may be derived by: 1) plotting all of the nEUIs that were calculated during the shape-specific simulations, 2) observing trends (e.g., energy demand trends) with respect to each of the shape definition parameters (e.g., Bx, By, W, H, Ns, θ, and ratio of perimeter length to footprint area), 3) finding a parameter (e.g., Bx, By, W, H, Ns, θ, and ratio of perimeter length to footprint area) that primarily affects a general trend (e.g., an energy demand trend) of the plotted curve, 4) finding the best formula as a function of the primary parameter to describe the general trend (e.g., energy demand trends) by using polynomial curve-fitting or by applying knowledge of curve patterns that can be described with other means of mathematical functions, 5) finding secondary, tertiary, and so on parameters (e.g., Bx, By, W, H, Ns, θ, and ratio of perimeter length to footprint area) that can be used to reduce variances of simulated values from the formula, and 6) adjusting formula using terms expressed with the secondary, tertiary, and so on parameters. In an embodiment, the formula derivation involves identifying key contributing factors (e.g., Bx, By, W, H, Ns, θ, and ratio of perimeter length to footprint area) that effect the energy demand of a building massing configuration. The operation of the shape-specific nEUI formula derivation engine 656 is repeated for each shape-specific database.

In a next operation, the nEUI base formula derivation engine 658 derives a base formula, which is common to all of the footprint shapes, from the previously derived shape-specific formulas. In an embodiment, a nEUI base formula, which is common to all of the footprint shapes, may be derived by: 1) finding the most common form of formula among all the formulas derived for each footprint shape, 2) determining a new pattern of formula (base formula) that generally describes the nEUIs of all footprint shapes, and 3) re-establishing formulas for each footprint shape using the base formula to describe nEUI trends of each footprint shape.

In a next operation, the shape-specific correction factor derivation engine 660 derives a correction factor for each footprint shape to calibrate the base normalized energy use index formula. In an embodiment, the correction factor corrects for variations related to the number of stories of the buildings, the void area dimensions, and in at least one case the orientation of the building in degrees, θ, relative to, for example, true north.

The nEUI formulas for each footprint shape, which are expressed using the common base formula, may be further improved by: 1) plotting and comparing a calculated nEUI curve with a simulated result curve, 2) finding parameters (e.g., Bx, By, W, H, Ns, θ, and ratio of perimeter length to footprint area) that can make the calculated nEUI curve closer to the simulated result curve, and 3) introducing correction terms that are functions of those parameters to reduce the error percentage to within an acceptable range, e.g., within 5% of the actual values.

In an embodiment, each shape-specific formula for calculating the normalized energy use index, nEUI, includes a base formula and a correction factor and can be expressed generally as:

nEUI-shape=(base formula)+correction factor

The base formula and/or correction factor may include intermediary factors and or coefficients. Examples of intermediary factors include:

Bfp=total number of bays in the footprint;
Be=total number of bays along the exposed perimeter of the footprint; and
Rs=Be/Bfp.

Examples of shape-specific formulas that have been derived for calculating the normalized energy use indexes, nEUIs, are provided in the Appendix. The examples include formulas for single-storey, two-storey, and three-plus storey buildings having footprint shapes R, L, Z, K, X, T, U, H, and O. The Appendix also includes alternate formulas that have been derived for buildings having more than two stories.

The shape-specific formulas, including corresponding coefficients, for calculating the normalized energy use indexes, nEUIs, are stored in the shape-specific nEUI formula databases 654 for use in the Building Realization Platform (BRP) as described below. It should be noted that, in an embodiment, the operations described with reference to FIGS. 19a-24 are preliminary operations that are performed in advance of the use of the building realization program in the BRP.

Figure 25:
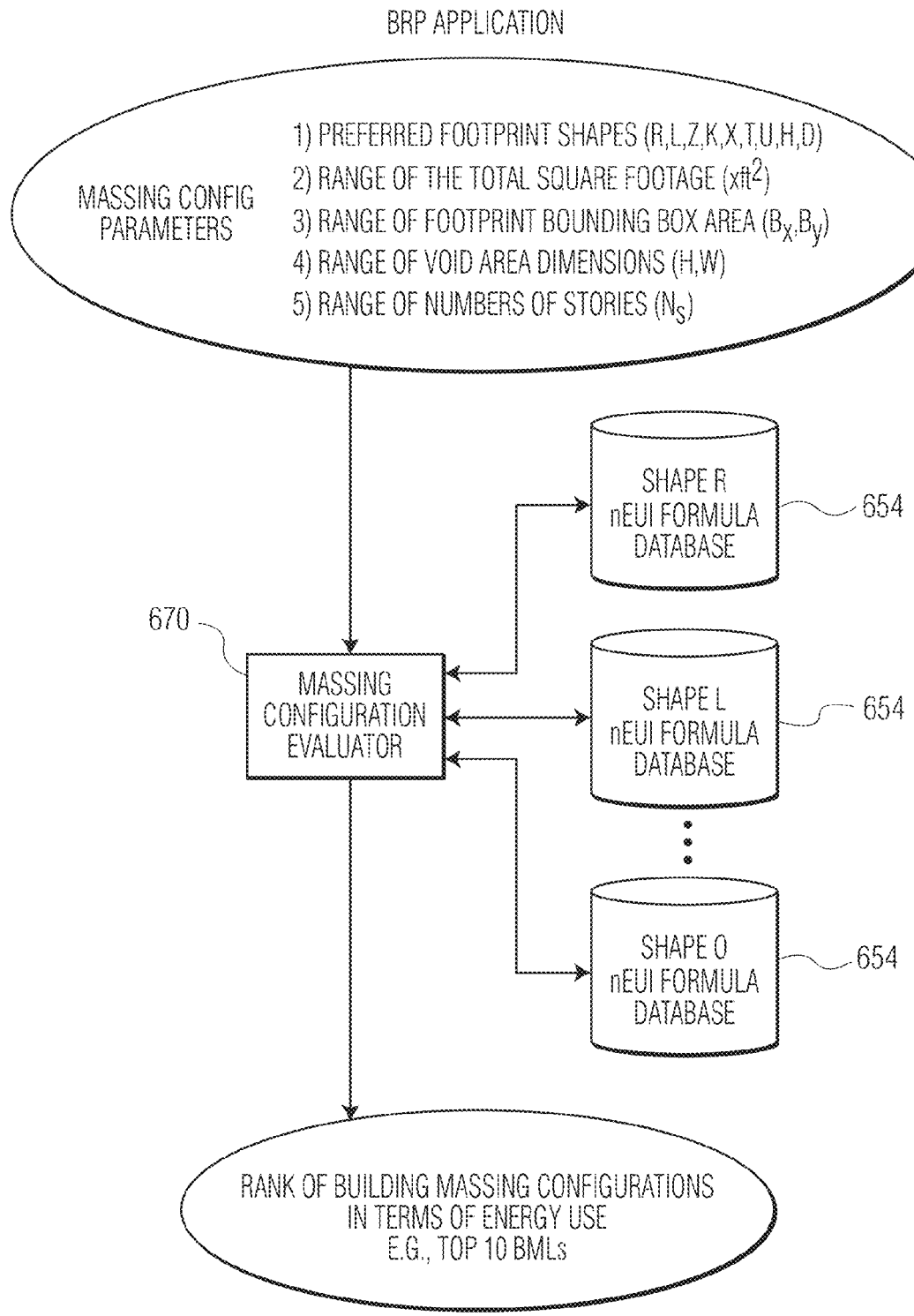
FIG. 25 illustrates an embodiment of a process for using shape-specific formulas to characterize the energy use of multiple different building massing configurations early on in the building design process.

Use of the shape-specific formulas to characterize the energy use of multiple different building massing configurations early on in the building design process is now described with reference to FIG. 25. When utilized within the Building Realization Platform (BRP) described above with reference to FIGS. 1-18, different building massing configurations are provided to a massing configuration evaluator 670. In an embodiment, the different building massing configurations are provided to the massing configuration evaluator as a set of parameters that can be defined as specific finite values or value ranges. For example the set of parameters may include:

1) a listing of the preferable footprint shapes;
2) a range of the total square footage of the building;
3) a range of the footprint bounding box area, Bx, By;

4) a range of the void area dimensions, H and W; and 5) a range of the number of stories, Ns.

The energy massing configuration evaluator uses the predefined shape-specific formulas to calculate normalized energy use indexes, nEUIs, for each building massing configuration and to output the normalized energy use indexes as desired by the user.

As described herein, the magnitude of the calculated normalized energy use indexes, nEUIs, is an indication of the energy efficiency of a particular building massing configuration relative to the reference building. Therefore, a relatively large nEUI indicates that the particular building massing configuration is less energy efficient, e.g., a building with the massing configuration would require more energy to operate, and a relatively small nEUI indicates that the particular building massing configuration is more energy efficient, e.g., a building with the massing configuration would require less energy to operate. Because the energy use indexes, nEUIs, are all normalized to the same reference building, the normalized energy use indexes, nEUIs, can be compared to each other as a metric of the relative energy efficiency between different building massing configurations.

An example operation of the above-described technique for characterizing the energy use of multiple different building massing configurations is now described with reference to FIGS. 26-28. In the example application, the set of massing configuration parameters is as follows:

1) preferable footprint shapes: all (R, L, Z, K, X, T, U, H, O);
2) range of the building total square footage: ≤150,000;
3) range of footprint bounding box area: 1≤Bx≤7 and 1≤By≤6;
4) range of void area dimensions: W≤5 and H≤6; and
5) range of number of stories: 1≤Ns≤4.

Given the above set of building massing configuration parameters, the massing configuration evaluator 670 calculates normalized energy use indexes, nEUIs, for 24,693 different building massing configurations. In an embodiment, all of the normalized energy use indexes, nEUIs, were calculated in less than one minute using the predefined formulas. The time frame of minutes is orders of magnitude less than the days, weeks, or months that would be required to run a different EnergyPlus simulation for each one of the different building massing configurations.

Figure 26:
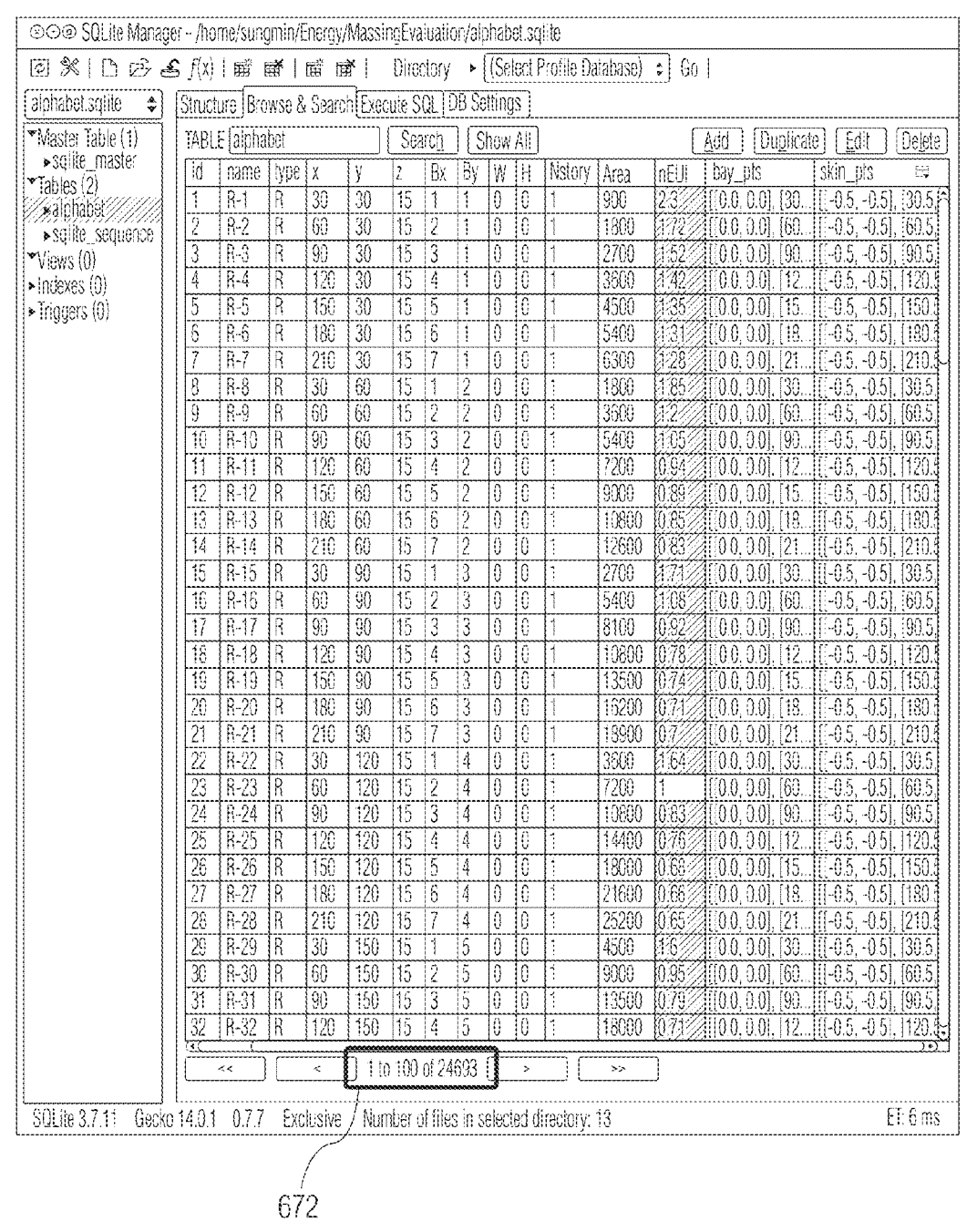

FIG. 26 depicts an embodiment of a user interface that displays the normalized energy use indexes, nEUIs, of 32 of the 24,693 different building massing configurations. In particular, FIG. 26 depicts a scrollable window of building massing configurations 1-100 of 24,693 (highlighted box 672), in which the building massing configurations all have the footprint shape, R. Fields shown in FIG. 26 include:

id—a unique identification number of the building massing configuration;
name—the shape name and a shape-specific reference number;
type—identification letter of the footprint shape;
x—bounding box dimension on the x-axis in feet;
y—bounding box dimension on the y-axis in feet;
z—height of the building in feet;
Bx—bounding box dimension on the x-axis in number of bays;
By—bounding box dimension on the y-axis in number of bays;
W—void area width dimension in number of bays;
H—void area height dimension in number of bays;
Nstory—number of stories;
Area—total area of the building massing configuration in square feet; and
EUIn—normalized energy use index.

The massing configuration evaluator is configured to allow the set of normalized energy use indexes, e.g., all 24,693 nEUIs, to be searched, sorted, and/or manipulated in various ways to allow the data to be presented in a manner that is useful to the user. For example, the user may request a ranking of the 10 building massing configurations with the lowest normalized energy use index.

Figure 27:
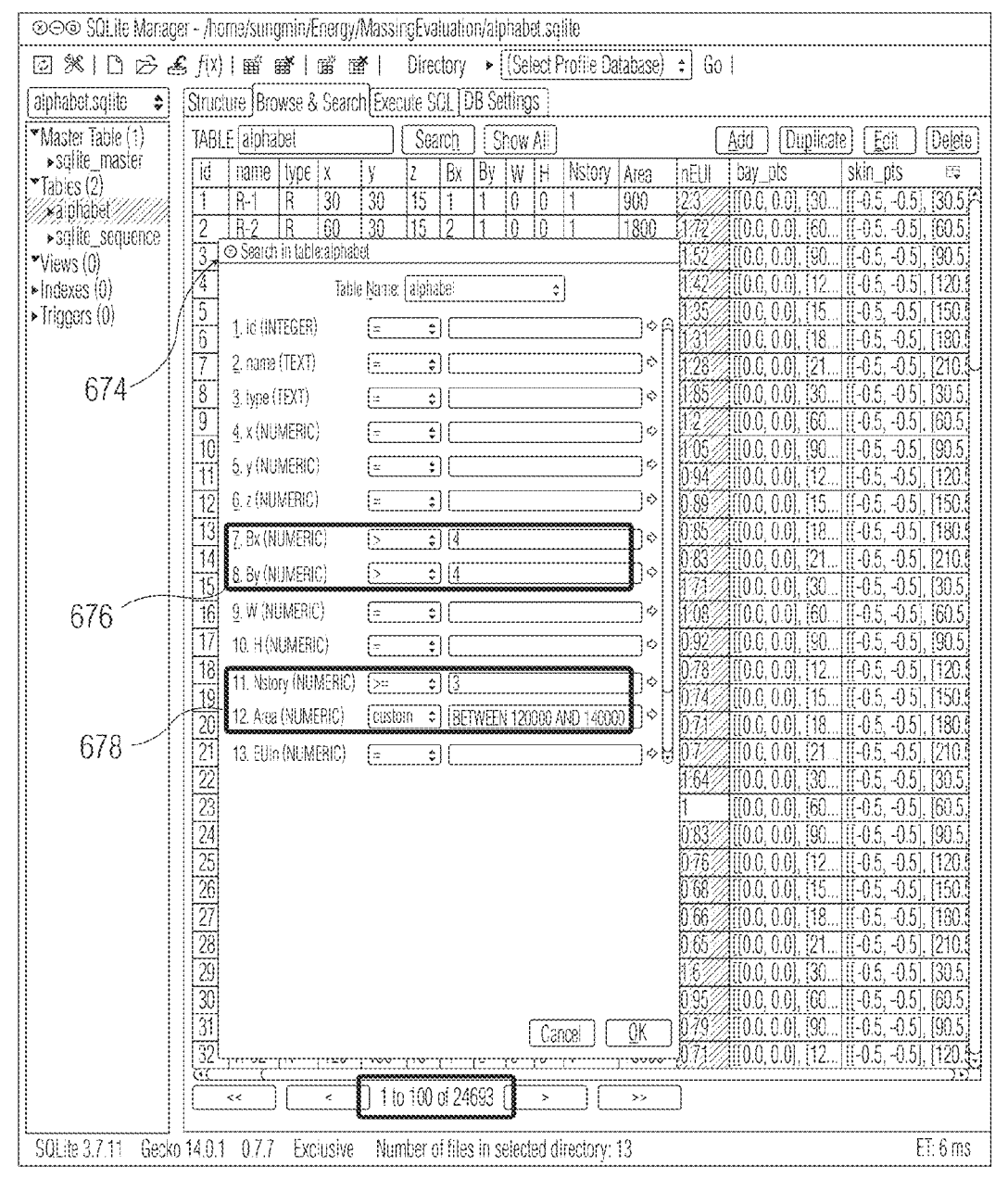

FIG. 27 depicts an embodiment of the user interface of FIG. 26 in which a search menu 674 is overlaid on the data from FIG. 26. In the example of FIG. 27, the search menu includes fields that match the columns of the data in FIG. 26, and the search menu is populated with four search parameters. In particular, the four search parameters are indicated in highlighted boxes 676 and 678:

Bx: >4;
By: >4;
Ns: ≥3; and
Area: 12,000≤area≤14,000.

Figure 28:

FIG. 28 depicts an embodiment of the user interface of FIG. 26 in which the displayed data is limited to building massing configurations that meet the criteria described with reference to FIG. 27. As illustrated in FIG. 28 (highlighted box 680), 403 of the original 24,693 different building massing configurations meet the search criteria and the building massing configurations are ordered by nEUI.

Figure 29:
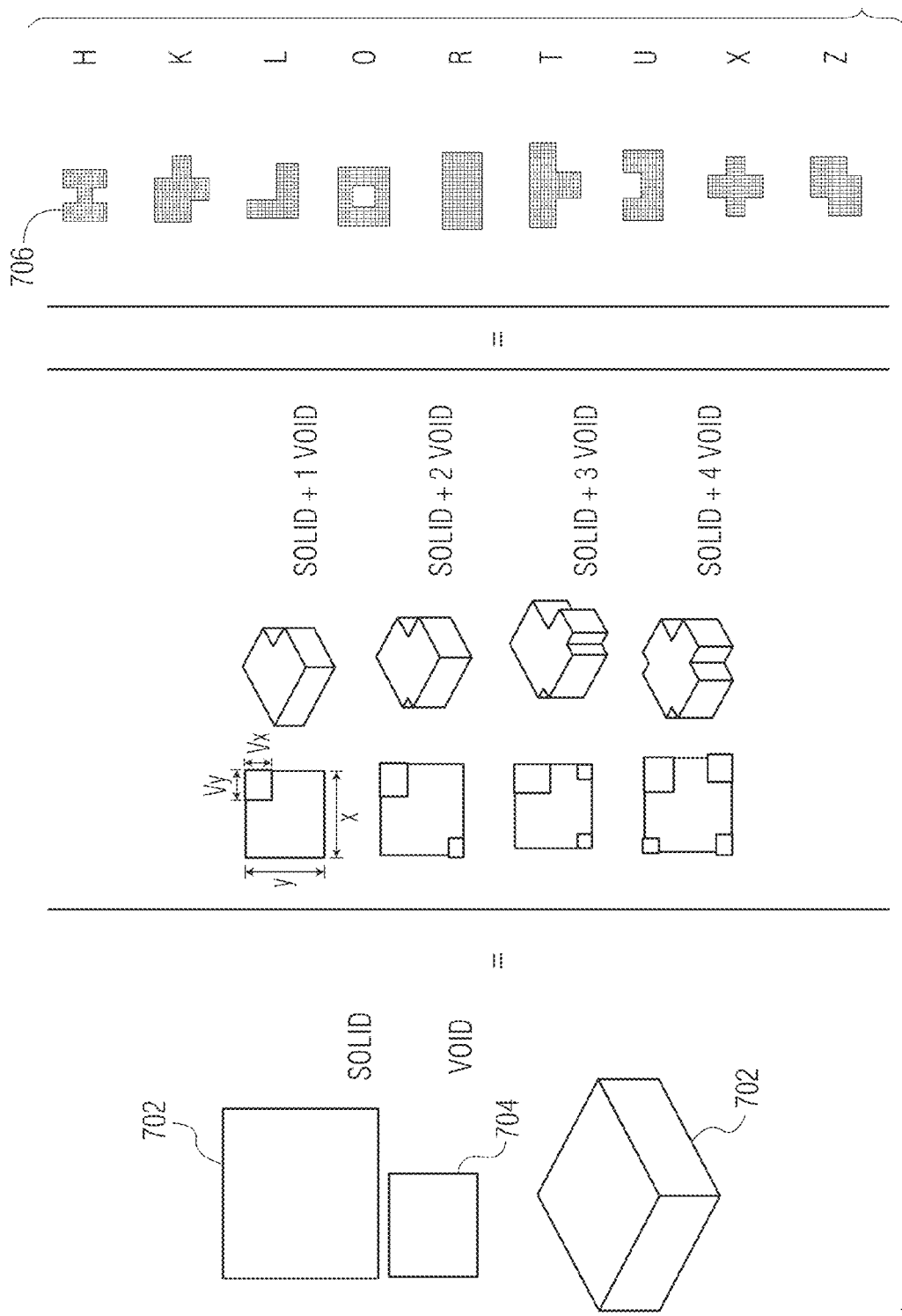
FIG. 29 illustrates a process for generating building massing configuration primitives from a base solid mass and the application of at least one void object according to a shape grammar.

Techniques for generating and managing building massing configurations are now described with reference to FIGS. 29-37. In an embodiment, sets of building massing configurations are generated using a shape grammar approach. With reference to FIG. 29, an initial set of building massing configuration primitives is generated from a base solid mass 702 and the application of at least one void object 704. The base solid is a three-dimensional rectangular mass having non-zero x, y, and z axis dimensions. A set of rectangular masses can be generated by varying the x, y, and z axis dimensions (e.g., parametrically in one bay increments where a bay is a fixed size, e.g., 30'×30', and in one floor increments where a floor is a fixed size, e.g., 15'). Other building massing configuration primitives can be generated by applying a set of rules, referred to as a shape grammar, to the rectangular mass. In the embodiment of FIG. 29, the set of rules involves applying at least one three-dimensional void object to the rectangular mass, in this case, a rectangular void object although void object with other shapes are possible. As shown in FIG. 29, multiple different void objects can be applied to a rectangular mass. Using a parametric shape grammar, e.g., varying the x and y dimensions by one bay and the z dimension by one floor height, void objects are applied to a rectangular mass to form a set of building massing primitives. For example, one, two, three, or four voids can be applied to a mass to form different building massing configurations. In the embodiment of FIG. 29, the shape grammar is applied in a manner that generates building massing configurations 706 having the footprint shapes as described above with reference to FIGS. 19a-19i. In particular, the building massing configuration shape primitives, which are referred to herein as "building letters" of a "building alphabet" include the shapes R (not shown), H, K, L, O, R, T, U, X, and Z. In an embodiment, applying values to the x, y, and z dimensions of the rectangular mass and to the void object(s) that correspond to realistic building sizes can result in thousands of different building massing configurations, e.g., 20,000 to 30,000 different building massing configurations.

Although a building alphabet with a particular set of footprint shapes (e.g., the "letters" of the alphabet) is described, other shapes may be included in the building alphabet and the shape geometry can be modified by changing the shape grammar.

Figure 30:
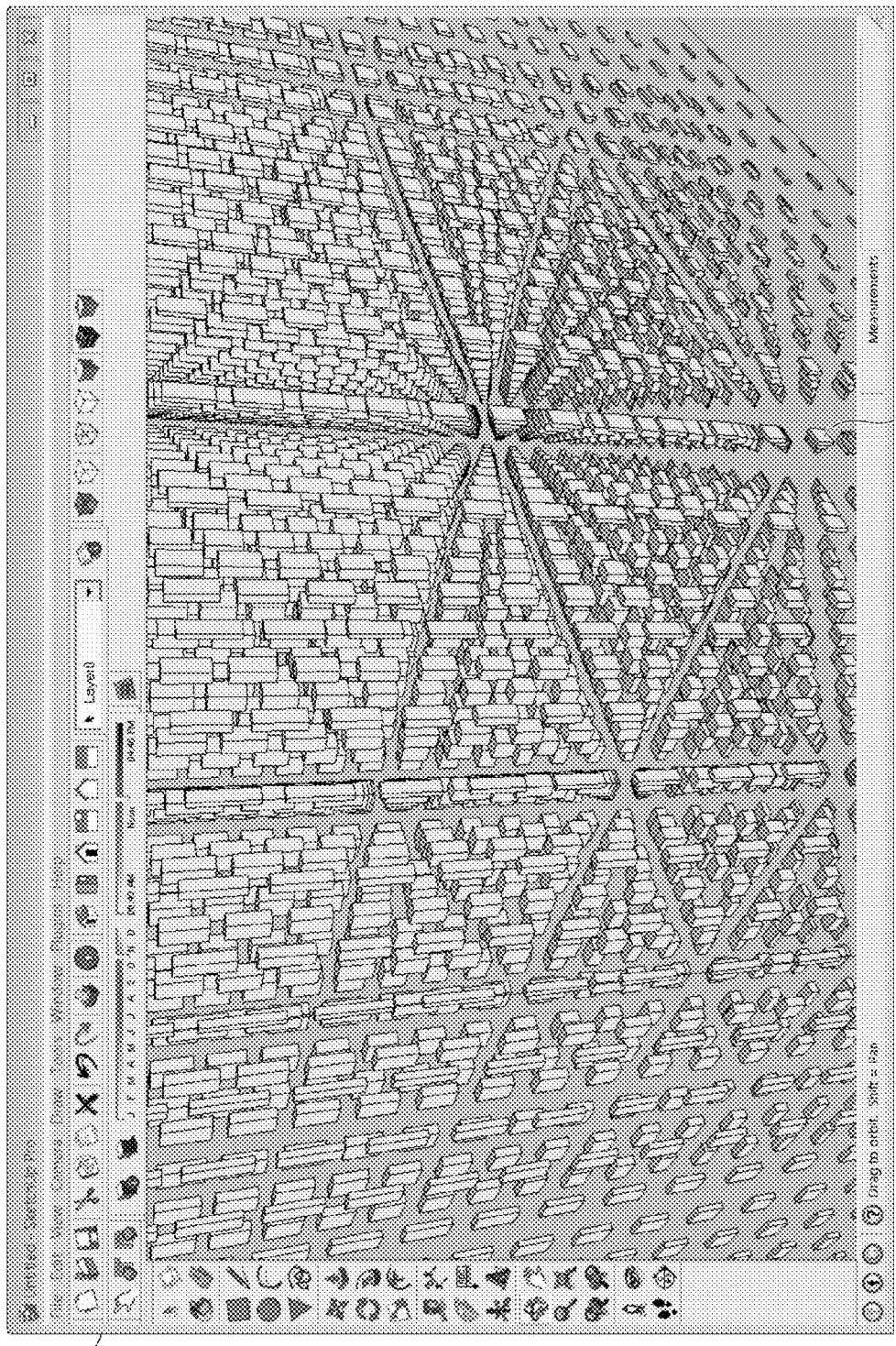
FIG. 30 depicts a graphical user interface that graphically displays building massing configurations for a rectangle footprint shape.
Figure 31:
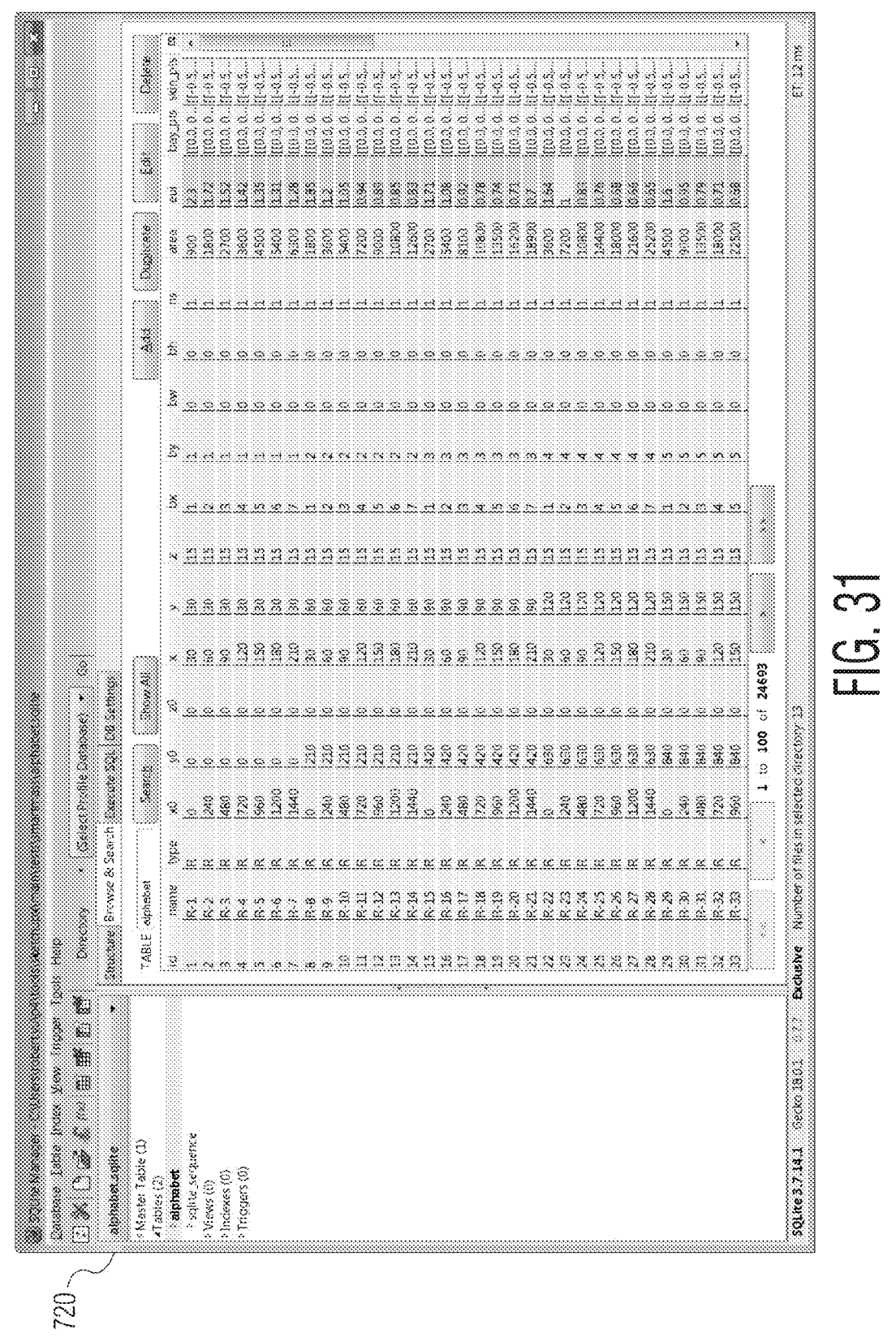

Application of a set of rules in the shape grammar to a particular building massing configuration can result in thousands of different building massing configurations for each building letter, e.g., each footprint shape. FIG. 30 depicts a graphical user interface (GUI) 710 that graphically displays building massing configurations 712 for a rectangle footprint shape. The graphical user interface of FIG. 30 helps to illustrate the scale of the number of different building massing configurations that can be generated for a single footprint shape. The generated set of building massing configurations can be stored in a database for fast and flexible access by the BRP. FIG. 31 depicts a graphical user interface 720 of entries in a building alphabet database that is generated using the shape grammar as described with reference to FIG. 29. As shown in FIG. 31, the building alphabet database includes 24,693 different building massing configurations, with configurations 1-33 being currently displayed. The information in the graphical user interface is similar to that described above with reference to FIG. 26.

Figure 32:
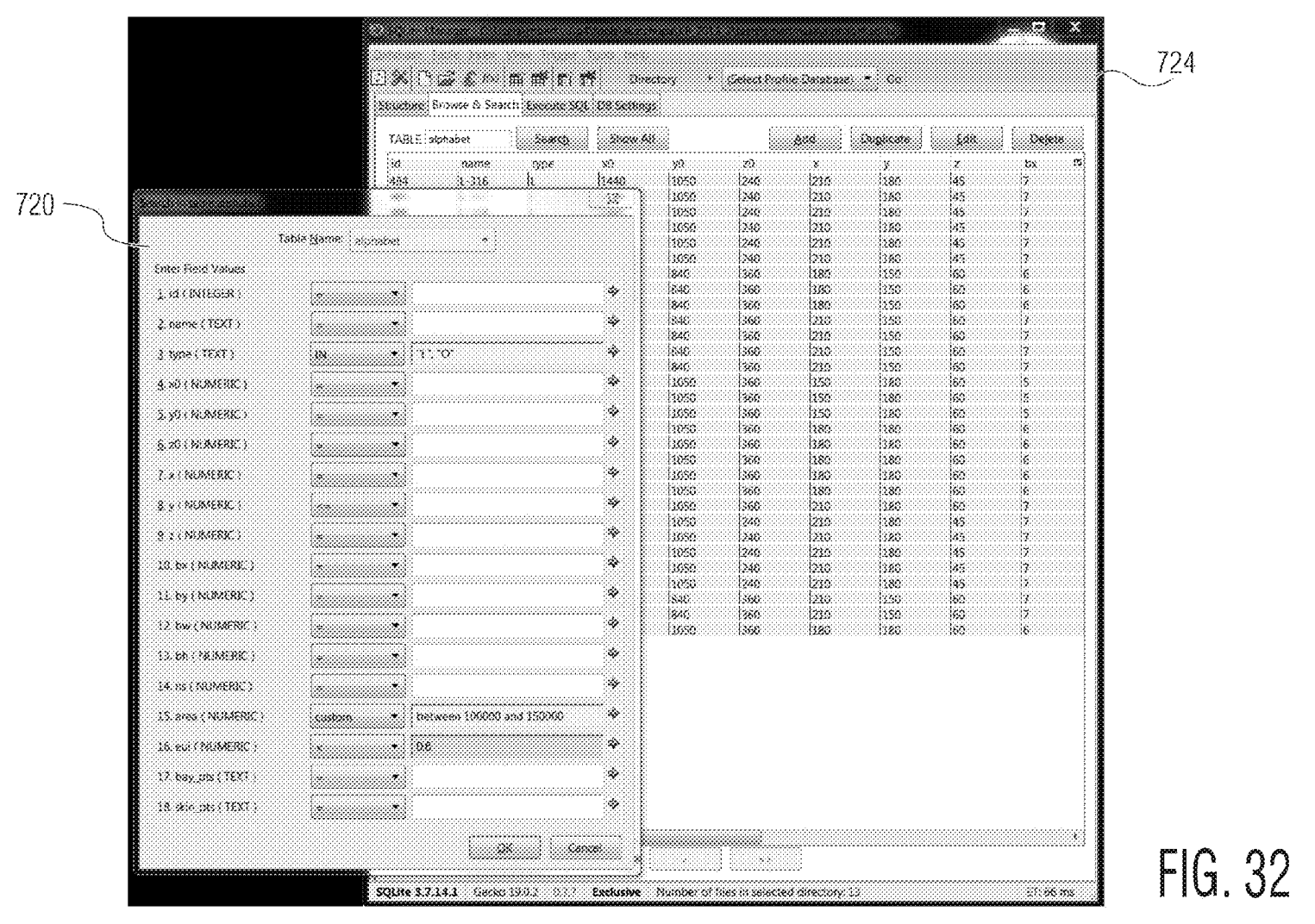

Given the extremely large number of different building massing configurations that can be generated, it is desirable to be able to manipulate the database to reduce the set of building massing configurations to better suit a particular building project. In an embodiment, the building alphabet database is searchable by any of the column fields. For example, a search can be run to find only those shapes that will fit on a particular building site having specific x and y dimensions. Such a search, or "pre-filtering," can be performed by specifying the limits of the bounding box dimensions, Bx and By. Other criteria (e.g., area, volume, aspect ratio, nEUI) can be used to pre-filter the building massing configurations. FIG. 32 depicts a graphical user interface 724 that includes a search window 726 that allows certain parameters of a search to be specified. For example, the search window allows any of the column parameters of a building massing database to be specified and searched according to the specification. In the example of FIG. 32, the search criteria specifies alphabet letters "L" and "O", area between 100,000 and 150,000 sq. ft., and having an nEUI of less than 0.6. In an embodiment, a pre-filtered set of building massing configurations is used to populate a building massing library for a specific building project. In other embodiments, the building massing library can be unfiltered such that the entire set of generated building massing configurations is available for evaluation in the context of the building design.

Figure 33:
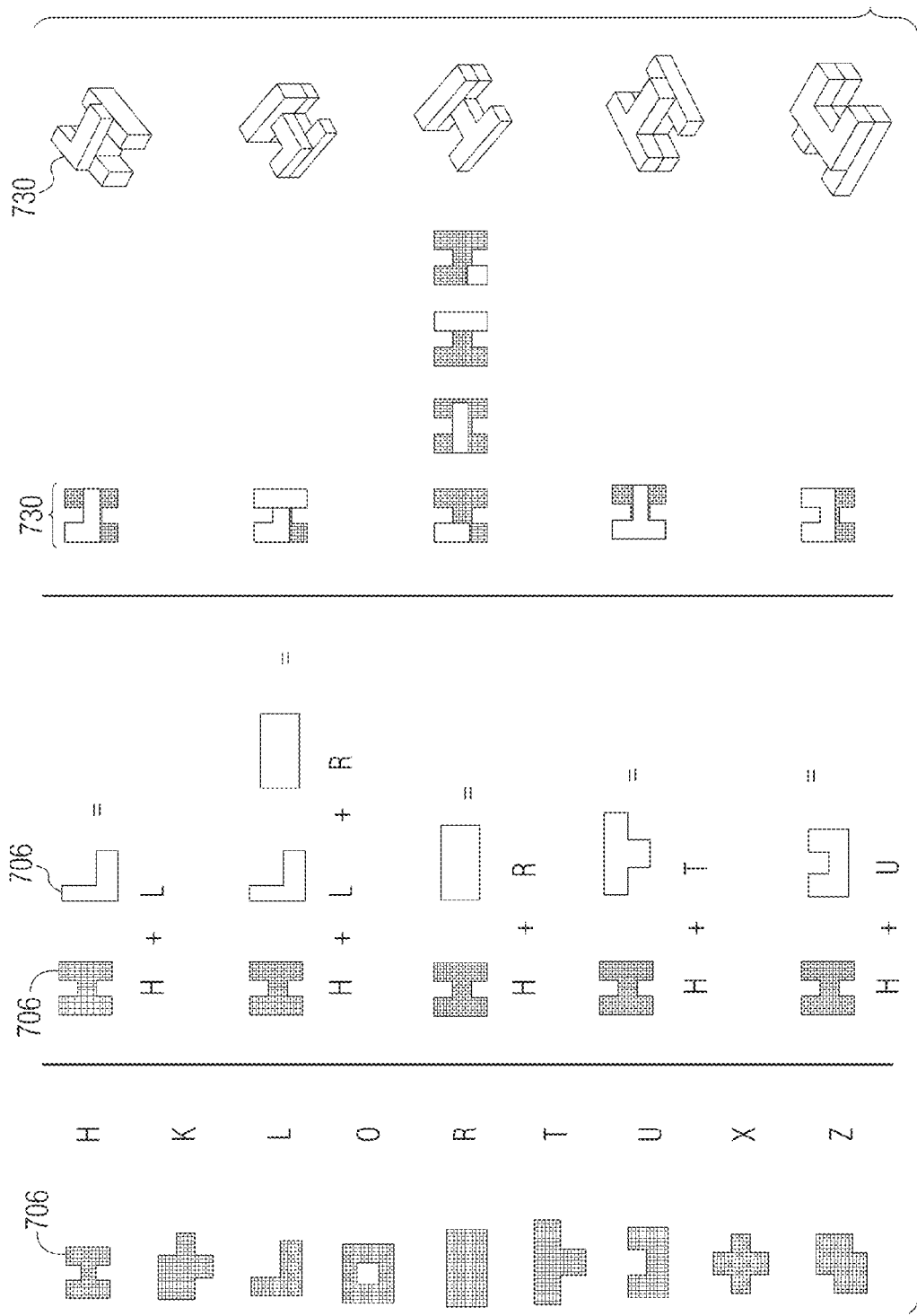
FIG. 33 illustrates the application of shape grammar to the building alphabet to form more complex building massing configurations.

While the building alphabet provides a certain set of building massing configurations, a more complex set of building massing configurations can be generated by combining different primitives, e.g., building letters from the building alphabet. FIG. 33 illustrates the application of shape grammar to the building alphabet to form more complex building massing configurations 730, referred to herein as "building words." As illustrated across the top row of FIG. 33, applying a rule of "H+L" results in the building word depicted in the upper right corner of FIG. 32. Rows 2-5 of FIG. 33 illustrate other rules in the shape grammar, e.g., "H+L+R," "H+R," "H+T," and "H+U." In an embodiment, the shape grammar is parametrically applied to form multiple building massing configurations of the same building word. In an embodiment, the shape grammar is applied to a pre-filtered set of building alphabet elements. For example, a pre-filtered set of "H" building elements may include 10 different building massing configurations and a pre-filtered set of "L" building elements may include 20 different building massing configurations. The total number of possible building words is the product of the "H" and "L" building elements, e.g., 10×20=200. That is, 200 different configurations of the "HL" (H+L) building word are generated from the building letters.

In an embodiment, the shape grammar is configured to require certain dimensions of two different building shapes to match, or to be within a certain range of each other. For example, with reference to the "HL" building word, the shape grammar may require that a particular dimension or dimensions of the "H" and "L" elements match so that the different stories of the building massing configuration have at least a portion of their respective footprints that are in common. The shape grammar may be modified, updated, etc., as desired to trigger the generation of different building massing configurations.

Figure 34:
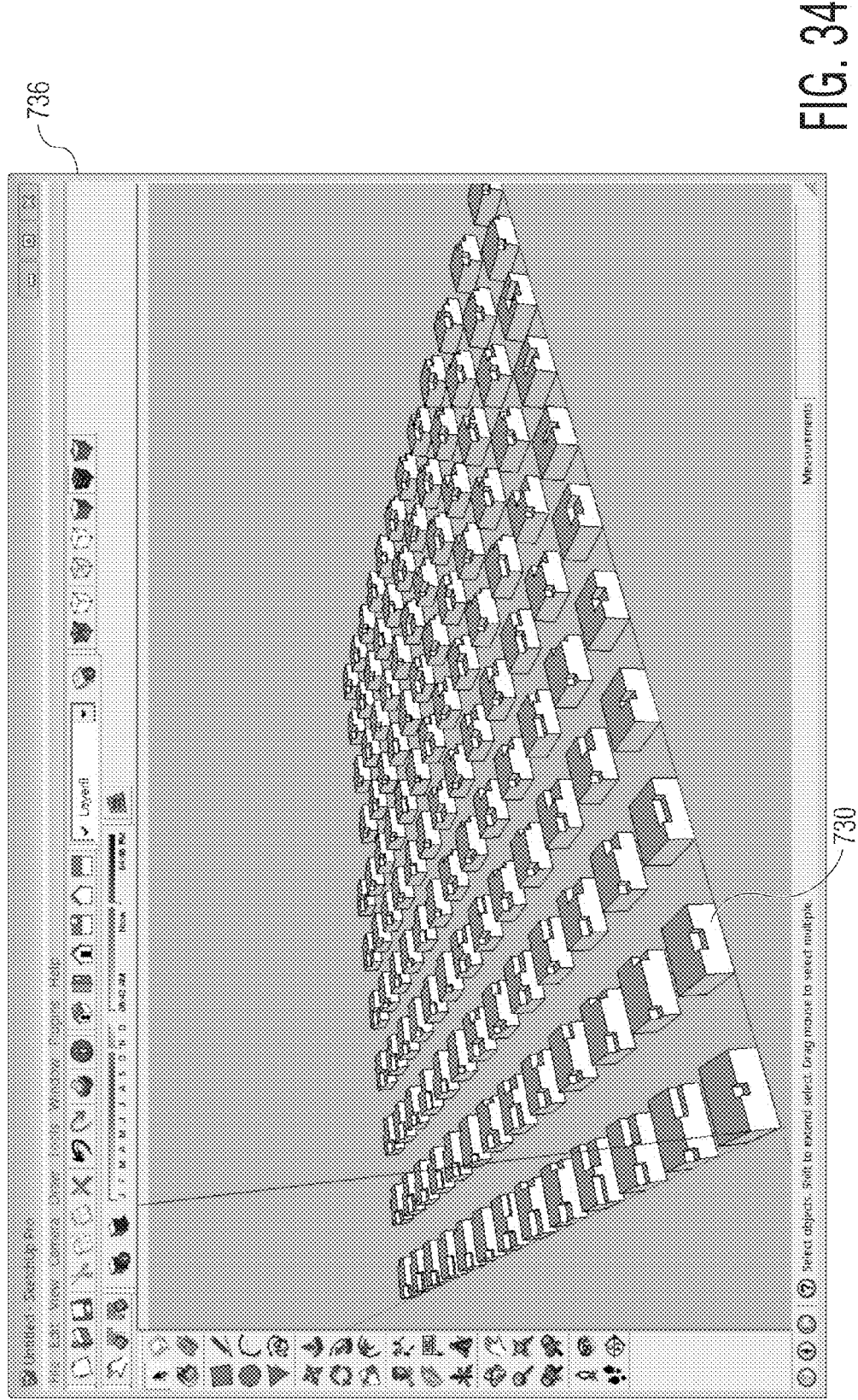
FIG. 34 depicts a graphical user interface that graphically displays building words that are formed by combining different primitives of the building alphabet.

FIG. 34 depicts a graphical user interface 736 that graphically displays building words 730 that are formed by combining different primitives (i.e., letters) of the building alphabet. For example, FIG. 34 depicts building words that include a "U" primitive stacked on top of an "R" primitive, a "T" primitive stacked on top of an "R" primitive, and a "Z" primitive stacked on top of an "R" primitive. In the example of FIG. 34, the x and y dimensions of the R primitives are fixed and the U, T, and Z primitives are applied to the R primitive in different dimensions, e.g., parametrically varied dimensions.

Figure 35:
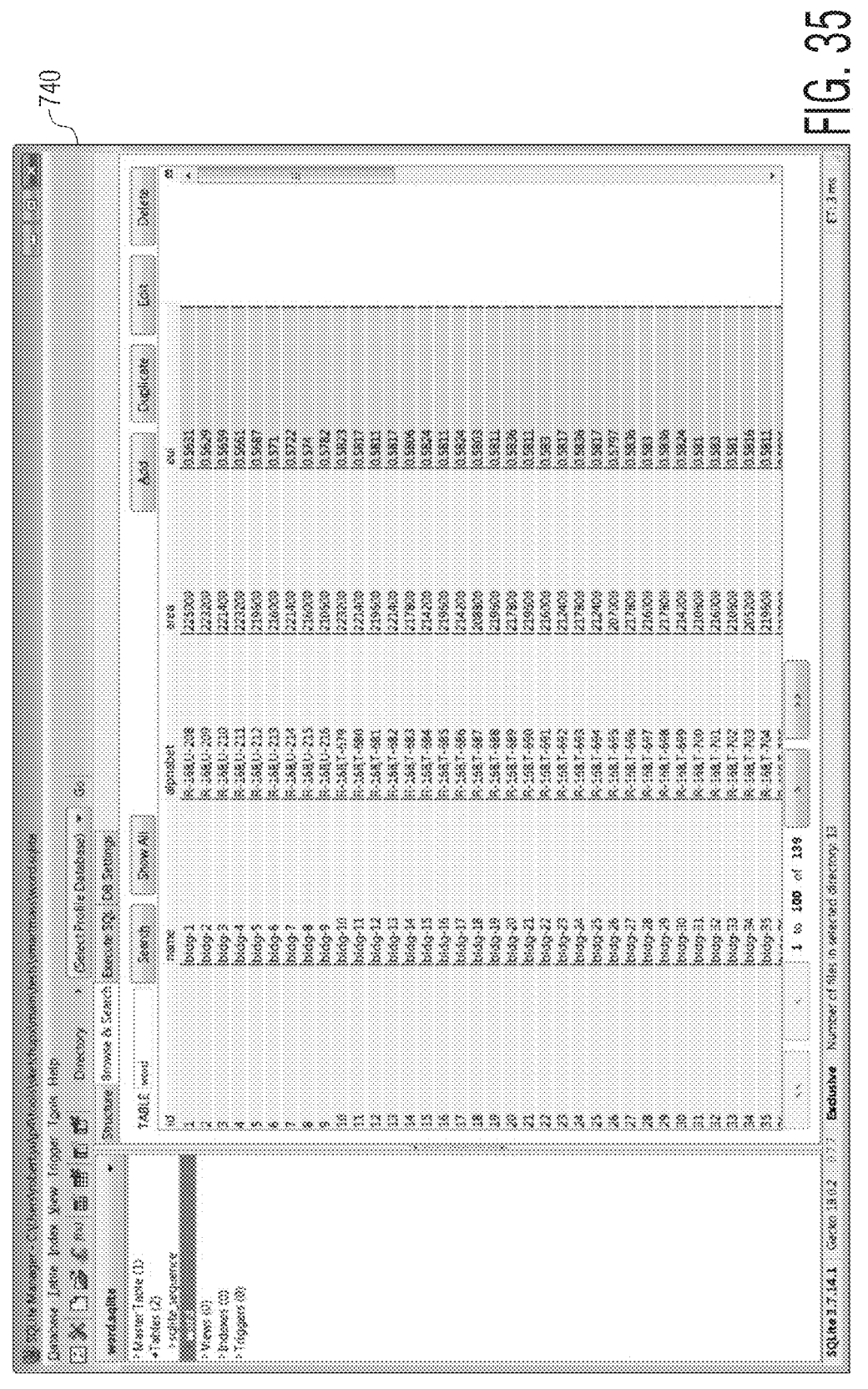

As described above with reference to the building alphabet, generated building massing configurations in the building word form can also be stored in a database. FIG. 35 depicts a graphical user interface 740 of different building massing configurations that are formed by a combination of the building letters. As shown in FIG. 35, the database includes 139 different building massing configurations having a particular combination of building letters, of which building massing configurations 1-35 are displayed. Building massing configurations 1-35 include "RU" (R+U) building words and "RT" (R+T) building words. The graphical user interface includes an id column, a name column, an alphabet column, an area column, and an EUI column. The id column associates the building word with a unique identifier, the name column associates the building word with a unique building name, the alphabet column indicates which primitives from the building alphabet were used to form the building word, the area column is the total area in terms of floor space of the building word (e.g., assuming each letter represents a different floor), and the word EUI represents the combined normalized EUI, nEUI, of the building word, where the word EUI is calculated on a proportional basis, e.g., relative to footprint area using the nEUIs from the corresponding building primitives. For example, the nEUI for building word id=1 is calculated as: area(R−168)·nEUI(R−168)/225,000+area(U−208)·nEUI (U−208)/225,000.

Figure 36:
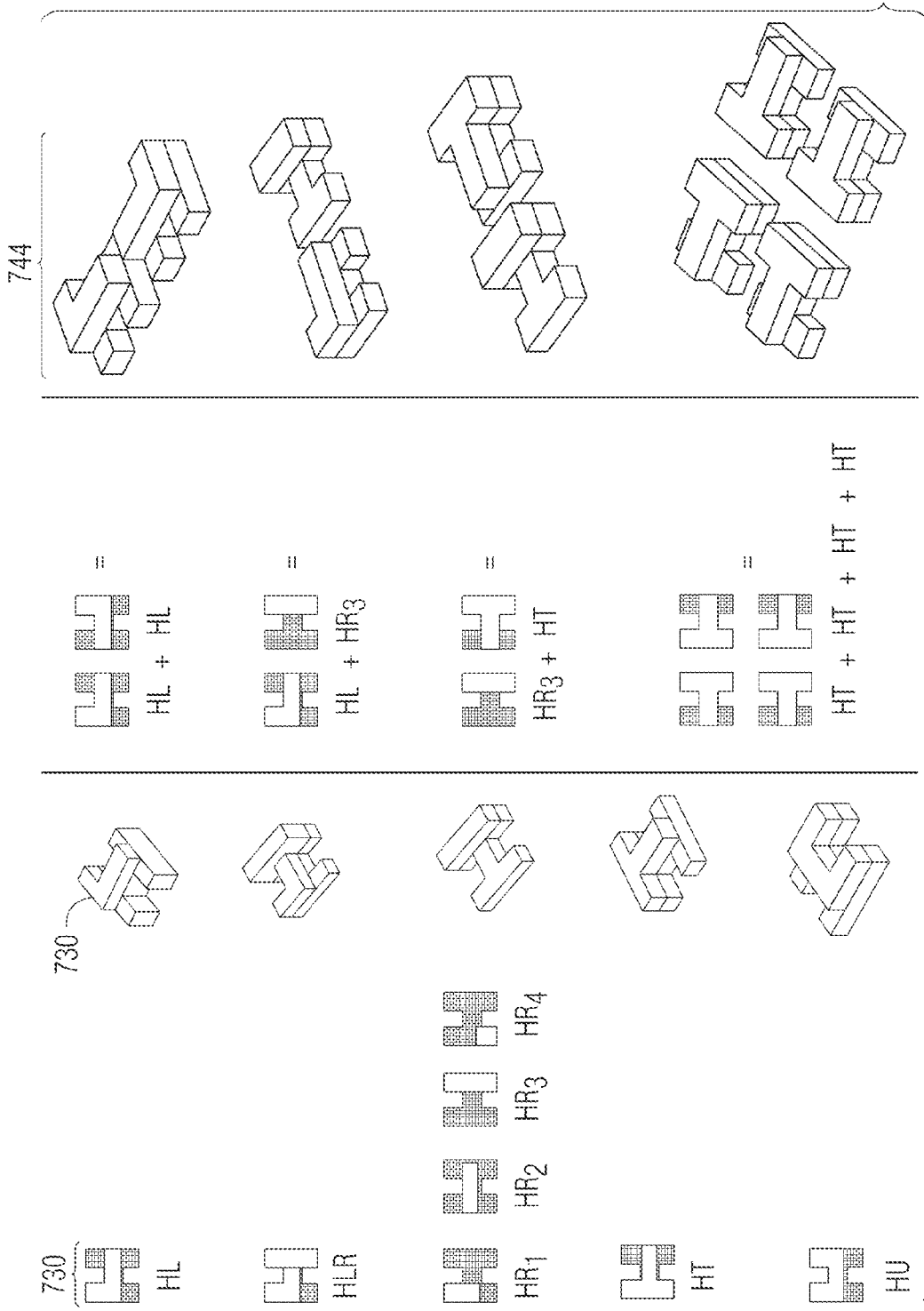
FIG. 36 illustrates the application of shape grammar to a set of building words to generate building sentences.

As described above, building massing configurations can be generated and referred to as building letters of a building alphabet or building words. In each case, a particular building massing configuration is one contiguous mass, e.g., a single contiguous building. In another embodiment, a shape grammar can be applied to the building alphabet and/or to building words to generate multi-building configurations in which the buildings are not physically connected to each other. Keeping with the "building alphabet" and "building word" taxonomy, multiple building massing configurations can be associated with each other to form a "building sentence." In an embodiment, the association of multiple buildings into a building sentence is a physical association or nearness. However, the association of multiple buildings into a building sentence may be a functional association instead of, or in addition to, the physical association. A building sentence is applicable to a multi-building complex such as a healthcare services complex. FIG. 36 illustrates the application of shape grammar to a set of building words 730 to generate building sentences 744, e.g., HL+HL. As illustrated across the top row of FIG. 36, two HL (H+L) building words are associated with each other to form a building sentence. In the embodiment of FIG. 36, the two HL building words (HL+HL) are associated with each other in that the buildings are understood to be located together at the same physical site at a known spacing and in the orientation as shown. Building sentences can also be generated from a building letter and a building word or from a building letter and another building letter, e.g., R+U.

Figure 37:
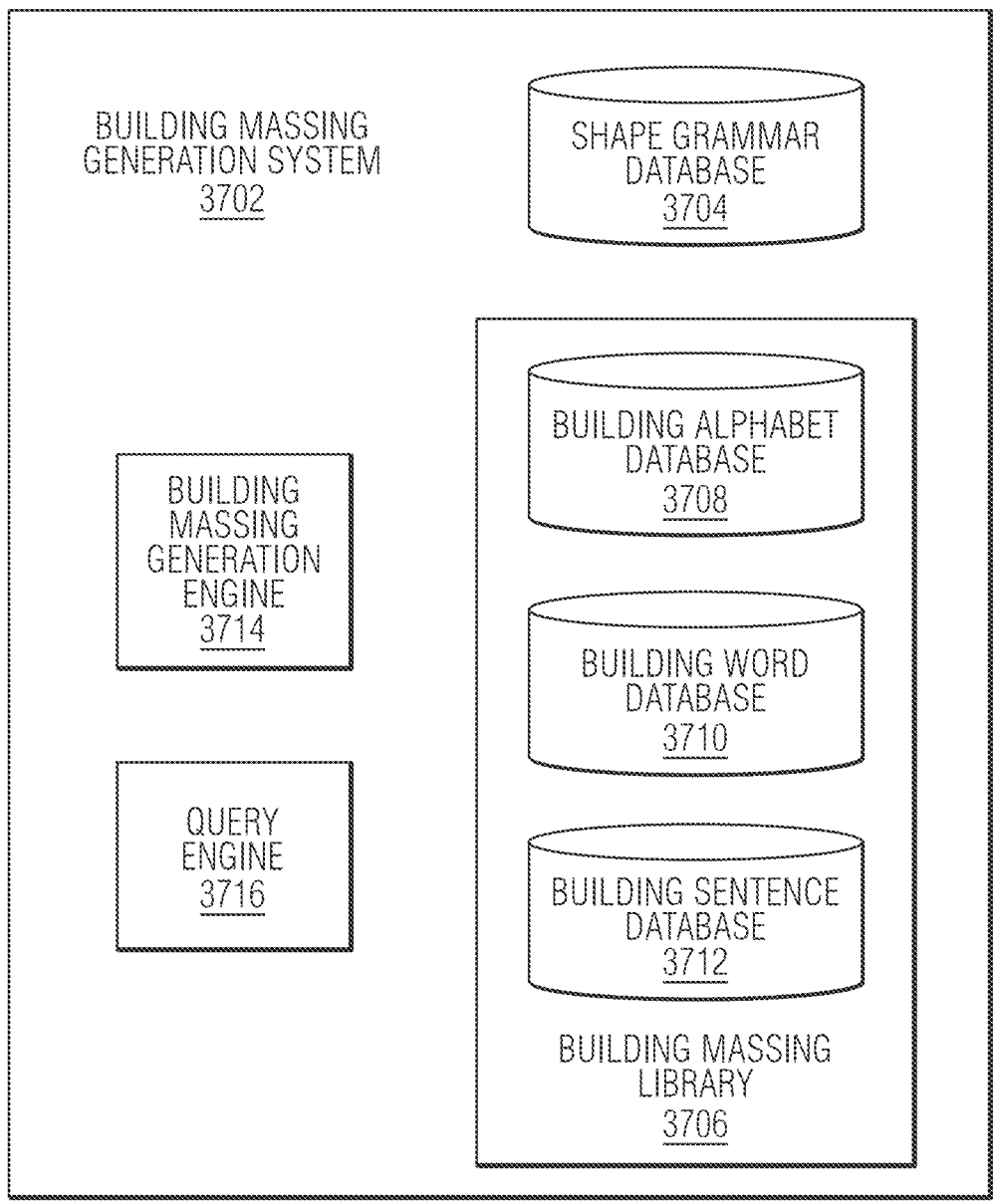
FIG. 37 depicts an embodiment of a system for implementing the building massing configuration generation and management techniques as described above.

FIG. 37 depicts an embodiment of a system 3702 for implementing the building massing configuration generation and management techniques as described above. The system of FIG. 37 includes a shape grammar database 3704, a building massing library 3706 that includes a building alphabet database 3708, a building word database 3710, and a building sentence database 3712, a building massing generation engine 3714, and a query engine 3716. The shape grammar database includes rules for generating the building alphabet, the building words, and/or the building sentences. The building alphabet database stores a set or sets of building letters, or primitives, as described, for example with reference to FIGS. 29 and 30. The building word database stores a set, or sets, of building words as described for example with reference to FIGS. 33 and 34. The building sentence database stores a set, or sets, of building sentences as described, for example, with reference to FIG. 36. The building mass generation engine applies the appropriate shape grammar, e.g., mass generation rules, to the appropriate shape database to form additional building massing configurations. The query engine enables the various shape databases to be searched and managed to generate a set of building massing configurations that may be desirable for evaluation in a particular building project. For example, the query engine enables the building massing library to be searched according to a parameter, or set of parameters, to reduce the set of different building massing configurations to set of building massing configurations that is a subset of the original set. For example, the building massing library is searched to find only those building massing configurations that meet certain project requirements, e.g., bounding box size, total square footage, number of floors, architectural parti, and/or energy efficiency. The reduced set of building massing configurations is then used to evaluate an aspect of a building design.

In an embodiment, the building massing generation system is a component of the Building Realization Program (BRP), which is implemented through a combination of software and hardware, such as computer executable instructions stored in memory and executed by the computer 500 of FIG. 18. In an embodiment, the generated building massing configurations are stored in the building massing library and can be used to support other functions in the Building Realization Program (BRP). For example, the building massing configurations in the building massing library can be used for energy analysis (as described in detail above), structural sizing (e.g., ETABS), structural detailing (e.g., Telka), block and stack, and façade generation.

In accordance with an embodiment of the invention, systems and methods for realizing a complex building system are disclosed. The systems and methods utilize computer-based techniques to rapidly explore large numbers of pattern matching scenarios on a scale which heretofore has not been attempted. In an embodiment, the computer-based technique performs large-scale pattern matching operations to find the best fit between functional patterns and spatial patterns. For example, with reference to a particular building system, the technique involves operational modeling to identify the types and volumes of services to provide (functional patterns) and to characterize the physical relationships between the services (e.g., adjacency preferences), along with establishing libraries of three dimensional spaces (spatial patterns), in the form of room and department libraries and building massing configuration libraries. Large numbers of functional patterns and spatial patterns are then matched to each other using cost-based algorithms to find the best match or matches between the form and function. The best matches between the form and the function correspond to a building design in which many of the functional and spatial aspects of the building system are defined. In a further embodiment, once defined, the spatial arrangement of a particular building can be used to perform additional operational modeling to see how the proposed spatial arrangement supports the desired types and volumes of services to be delivered in the building system. For example, the actual dimensions determined by the spatial arrangement are used to operationally model the types and volumes of service that were identified in the business model domain. In an embodiment, actual dimensions include dimensions between department blocks as defined by the spatial arrangement. Using actual spatial dimensions in the operational modeling enables the building designer to evaluate how a physically realized building will perform. Operationally modeling with actual spatial dimensions also allows for further design iterations that can adjust the functional patterns and/or the spatial patterns early on in the building design process.

Figure 38:
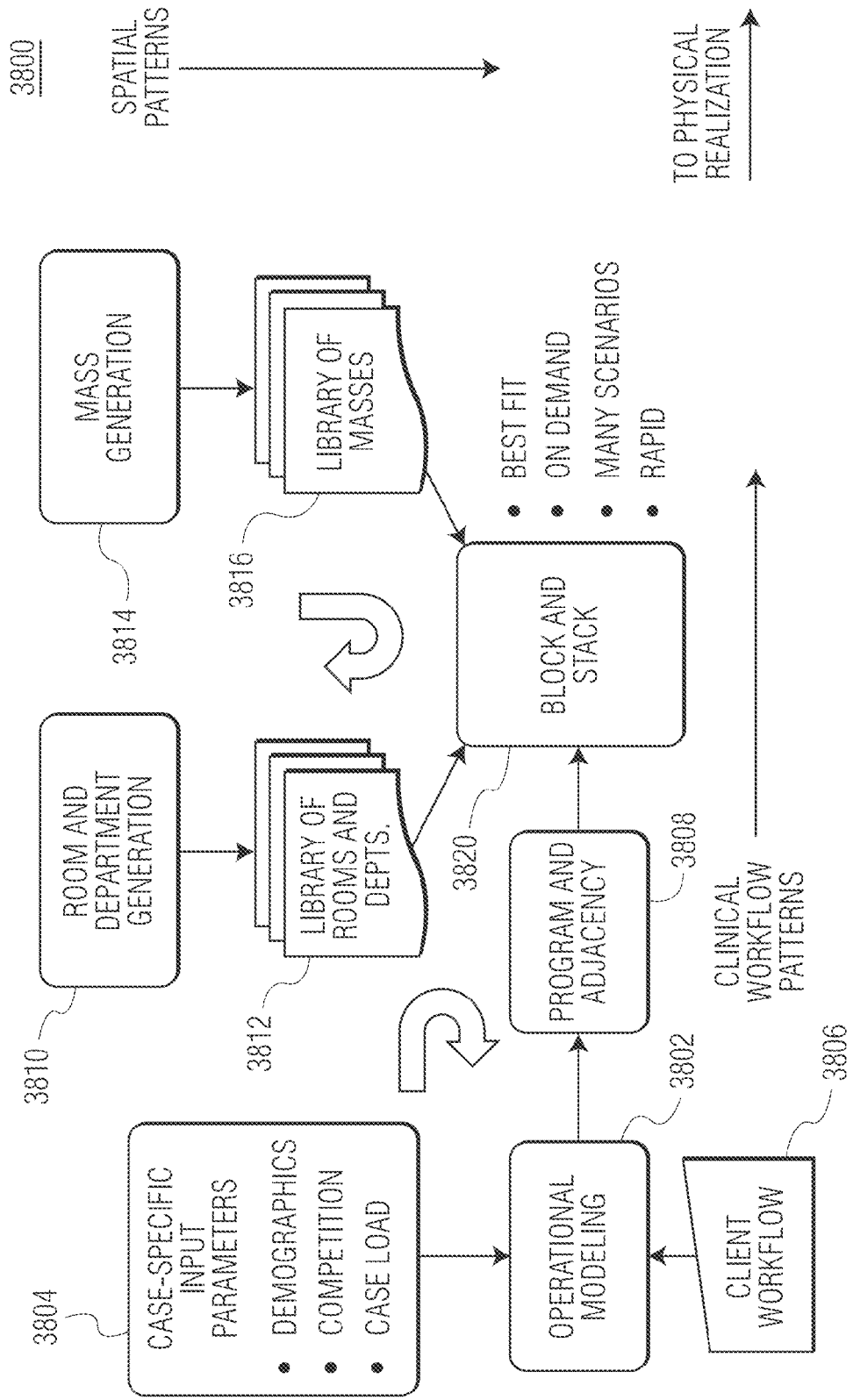
FIG. 38 is a process flow diagram of an iterative building realization process that illustrates an embodiment of a design flow that involves computer-based pattern matching.

FIG. 38 is a process flow diagram of an iterative building realization process 3800 that illustrates an embodiment of a design flow that involves computer-based pattern matching. As illustrated in FIG. 38, clinical workflow patterns are matched to spatial patterns (e.g., room/department libraries and building massing configuration libraries) to produce a physical realization, e.g., a spatial arrangement (SA), of a building system.

At the "operational modeling" block 3802, various inputs are used to operationally model the functions of a particular building system. One aspect of the input relates to identifying the types and volumes of services that are to be provided in the specific case. Case-specific input parameters 3804 that may affect the types and volumes of services to be provided include, for example, the demographics and the location of the building system, the amount of competition in the area around which the building is to be located, and the case load of the building owner or operator. In addition to the types and volumes of services, another aspect of the operational modeling input is the client workflow 3806, which defines the processes related to the building system, including the processes involved in providing the actual healthcare services and the processes involved in running the building system. For example, the client workflow may define the steps required to perform functions and sub-functions related to administration, admitting, diagnostic, imaging, acute care, observation, rehabilitation, surgery, laboratory, emergency, pharmacy, neonatal, delivery, information technology, sanitation, facilities, cafeteria, kitchen, etc. In an embodiment, the client workflow has a task aspect (e.g., what is being done and by whom), a temporal aspect (e.g., how long does the task take), and a spatial aspect (e.g., where is the task taking place).

Given the above described inputs, the operational modeling block can produce outputs that are used by a program and adjacency block 3808 to specify the "program" and "adjacency" for a particular building. In an embodiment, the "program" of a building defines the types and volumes of services to be provided within the building. The types and volumes of services to be provided within the building can be expressed as, for example, the number of surgery patients expected per month, the number of trauma patients expected per month, the number of baby deliveries expected per month, etc. In an embodiment, the types and volumes of services are defined in terms of functional groupings. For example, the functional groupings of the building are defined by unique functional identifiers that represent a specific type and a specific volume of service. For example, the functional grouping "surgery_10" represents a surgery function with ten surgery rooms and the functional grouping "surgery_12" represents a surgery function with twelve surgery rooms. The functional groupings may also include sub-functions that specify additional types and volumes of services that are necessary to support the primary function. Functional groupings can be defined for any type and volume of services that are performed within the building system.

In an embodiment, the "adjacency" of functional groupings describes the spatial relationship between functional groupings. That is, the adjacency provides an indication of how important it is for certain functional groupings to be located spatially close to other functional groupings. For example, an adjacency preference can be envisioned as a heat map in which the color red represents a relatively strong adjacency preference between functional groupings and the color blue represents a relatively weak adjacency preference between functional groupings, with a transition from red to blue representing the degree of adjacency preference between the extremes. In an embodiment, the adjacency preference of the functional groupings is represented in an adjacency matrix in which the importance of spatial closeness between functional groupings is identified. In an embodiment, the adjacency of pairs of functional groupings is defined by certain adjacency types, identified as:

A—Strong Connection: Adjacent/Abutment;
B—Strong Connection: Different Floor Acceptable/Stacked;
C—Close: Same Floor Required;
D—Close: Different Floor Acceptable;
E—Separation: Required—non-adjacent, same floor acceptable;
F—Separation: Preferred; and
G—Indifferent.

To implement a cost analysis of a particular spatial arrangement, the adjacency types can be quantified as numeric cost values, e.g., values from 0 to 100, where 0 represents a relatively low cost and 100 represents a relatively high cost. For example, an adjacency of type "A," between two functional groupings will have a relatively high cost function when two such type "A" department blocks are located relatively far away from each other in a building system. Adjacency is described in more detail below.

With reference to FIG. 38, the "room and department generation" block 3810 is configured to generate a library of rooms and departments 3812. The library of rooms and departments defines spatial aspects of rooms and departments. In an embodiment, a department, referred to herein as a department block, DEPBLOCK, or Dblock, defines the spatial parameters of a functional grouping. For example, a department block is a three-dimensional object with x, y, and z dimensions, or dimension ranges, a number of specific room types, a circulation pattern or patterns, and a corresponding functional grouping. A department block may also have a defined column grid pattern and certain perimeter edge requirements. In an embodiment, a department block is a data set that can be graphically displayed using a three-dimensional graphics programs such as SKETCHUP or REVIT. An example list of department blocks and corresponding functional groupings (identified as "FuntionName") includes:

"MEDSURG_24"
FunctionName: "function_patient"
SubFunction: "acute"
ProgramBeds: 24
"MEDSURG_16"
FunctionName: "function_patient"
SubFunction: "acute"
ProgramBeds: 16
"MEDSURG_12"
FunctionName: "function_patient"
SubFunction: "acute"
ProgramBeds: 12
"OBSERV_10"
FunctionName: "function_patient"
SubFunction: "observation"
ProgramBeds: 10
"IPRHAB"
FunctionName: "function_treatment"
SubFunction: "rehab"
"CLINLAB"
FunctionName: "function_lab"
SubFunction: "clinical"
"ED"
FunctionName: "function_emergency"
"IMAGING"
FunctionName: "function_imaging"
"INTERVENT"
FunctionName: "function_treatment"
SubFunction: "surgery"
"SURGERY"
FunctionName: "function_treatment"
SubFunction: "surgery"
"PRE_POST"
FunctionName: "function_prepost"
"ICU_12"
FunctionName: "function_patient"
SubFunction: "critical"
ProgramBeds: 12
"CAFETERIA"
FunctionName: "function_food_prep"
SubFunction: "dining"
"STEPDOWN_9"
FunctionName: "function_patient"
SubFunction: "acute"
ProgramBeds: 9
"KITCHEN"
FunctionName: "function_food_prep"
SubFunction: "kitchen"
"GYNUNIT_8"
FunctionName: "function_patient"
SubFunction: "acute"
ProgramBeds: 8

"PHARMACY"
FunctionName: "function_drug_prep"
SubFunction: "pharmacy_main"
"STERILE_PROC"
FunctionName: "function_clinical_support"
SubFunction: "sterile_processing"
"BLDG_SVCS"
FunctionName: "function_bldg"
"BIOMED"
FunctionName: "function_clinical_support"
SubFunction: "biomedical_engineering"
"IT_DATA"
FunctionName: "function_bldg"
"MAT_MGNT"
FunctionName: "function_clinical_support"
"EVS"
FunctionName: "function_clinical_support"
SubFunction: "materials_management"
"SECURITY"
FunctionName: "function_bldg"
SubFunction: "security"
"ADMIT"
FunctionName: "function_admin"
SubFunction: "reception"
"VOLUNTEERS"
FunctionName: "function_admin"
"HIM"
FunctionName: "function_admin"
"ADMIN"
FunctionName: "function_admin"
"TRANS_LIFT"
FunctionName: "function_bldg"
SubFunction: "employee"
"STAFF_LOCKERS"
FunctionName: "function_bldg"
SubFunction: "employee"
"MULTI_TESTING"
FunctionName: "function_exam"
SubFunction: "testing"
"ON_CALL"
FunctionName: "function_bldg"
SubFunction: "employee"
"LDRP_9"
FunctionName: "function_patient"
SubFunction: "womens"
ProgramBeds: 9
"POSTPARTUM_16"
FunctionName: "function_patient"
SubFunction: "womens"
ProgramBeds: 16

In an embodiment, the above-provided list of department blocks defines the space program of a building system. That is, the list of department blocks defines both the type and volume of services ("program") that are to be provided and the spatial arrangement ("space") of the individual department blocks. The list of department blocks does not define the spatial arrangement of the department blocks relative to each other within a particular building massing configuration.

The "mass generation" block 3814 is configured to generate a library of masses 3816, where a mass is a building massing configuration, also referred to as a building envelope or a building "form and shell." The building massing configuration defines a three dimensional building space as described above with reference to FIGS. 29-37. In an embodiment, the mass generation block is configured to perform mass generation, evaluation, and pre-filtering as described above with reference to FIGS. 19a-37 and the library of masses corresponds to the building massing library 3706 of FIG. 37 and includes multiple different building massing configurations.

With the building "program" and "adjacency" defined and the library of rooms and departments 3812 and the library of masses 3816 defined, a "block and stack" block 3820, also referred to as the "block and stack tool," is configured to perform a computer-based pattern matching algorithm. For example, the pattern matching algorithm involves placing a defined set of department blocks into multiple different building massing configurations to find the best arrangement, where the arrangement has a defined building massing configuration and all of the department blocks are placed in a specific location within each different building massing configuration. In an embodiment, the block and stack tool implements a cost function algorithm to identify combinations of the functional patterns and spatial patterns that have the lowest cost. As is described in more detail below, cost is measured relative to how well the arrangement of the department blocks meets a certain set of constraints related to, for example, adjacency preferences, floor location, department overlap, excess capacity, and perimeter needs. Using a cost function algorithm, tens of thousands of different pattern arrangements can be rapidly evaluated to converge on spatial arrangements that have the lowest cost, wherein a low cost solution indicates a good match between form and function. Low cost solutions can then be further evaluated in the building realization process to design a building that meets, for example, the defined customer needs. In an embodiment, the spatial arrangements can be used in further operational modeling to determine how well a particular building is able to implement the program that was defined by the operational modeling block. That is, the dimensions defined by the spatial arrangement (SA) can be used as input for further operational modeling using specific spatial dimensions.

Figure 39:
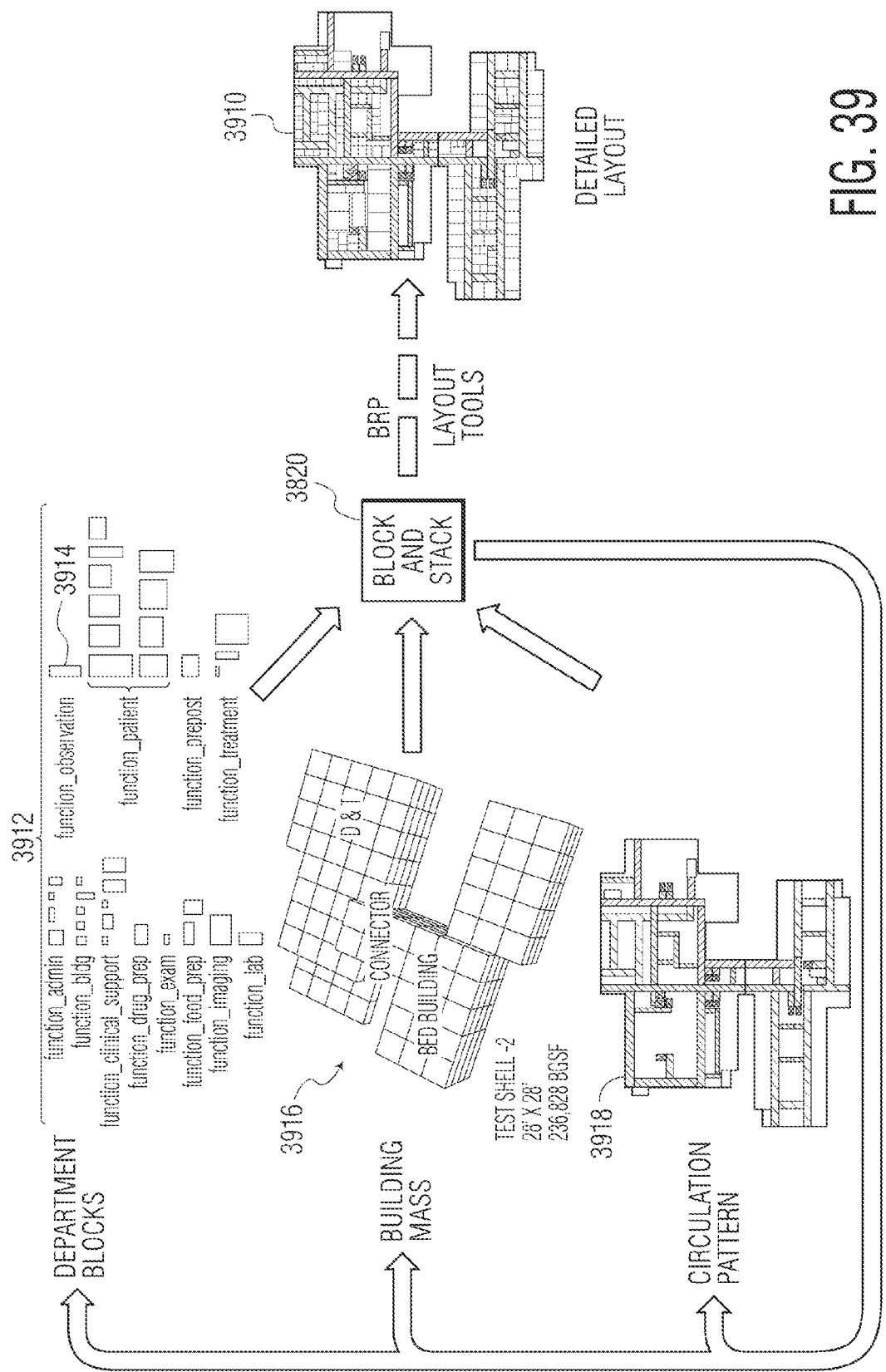
FIG. 39 represents a block and stack tool that receives input related to "department blocks," "building mass," and "circulation pattern," and outputs at least one block and stack arrangement in which the building massing configuration and the location of the department blocks within the building massing configuration are spatially defined.
Figure 40C:
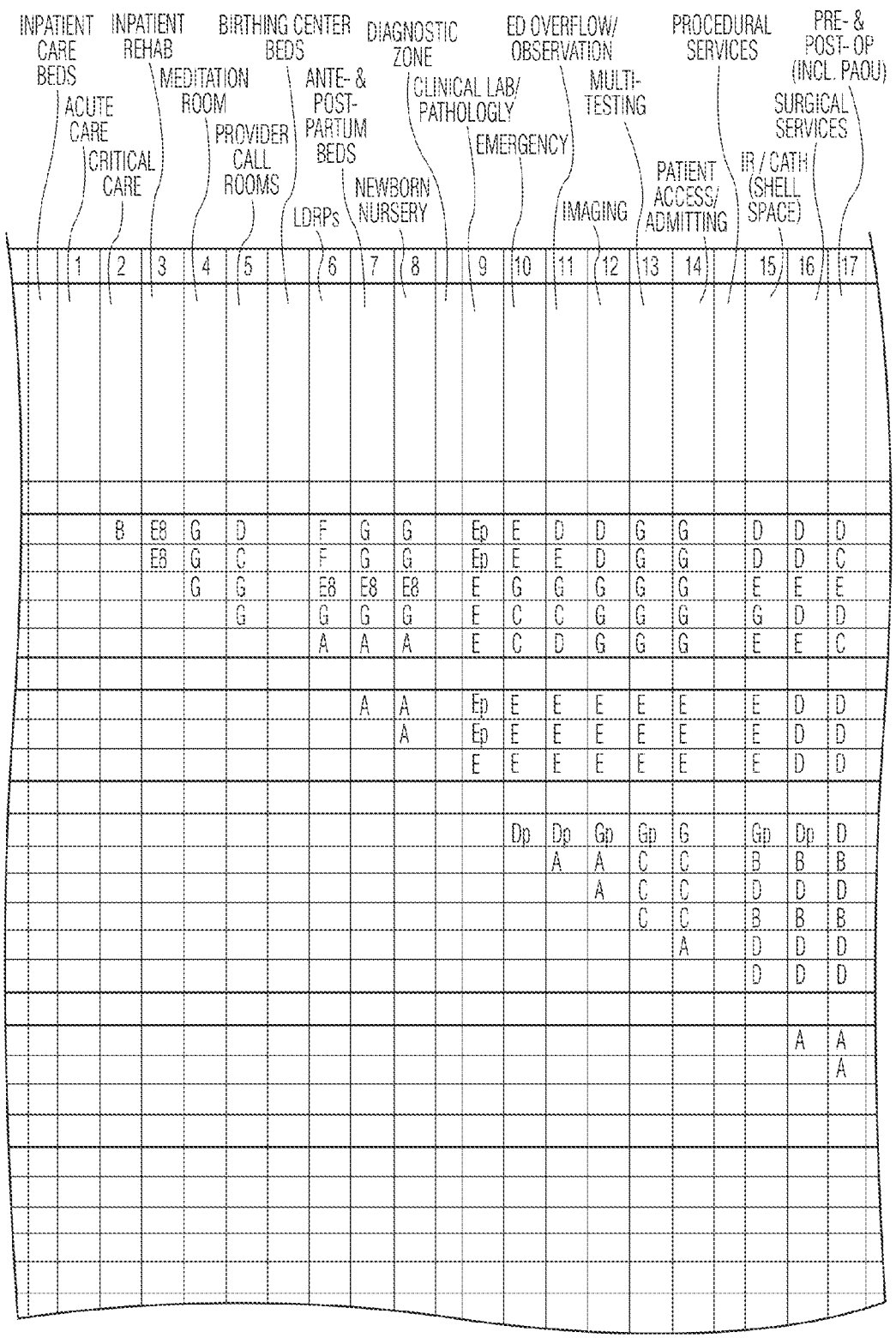
Figure 40E:
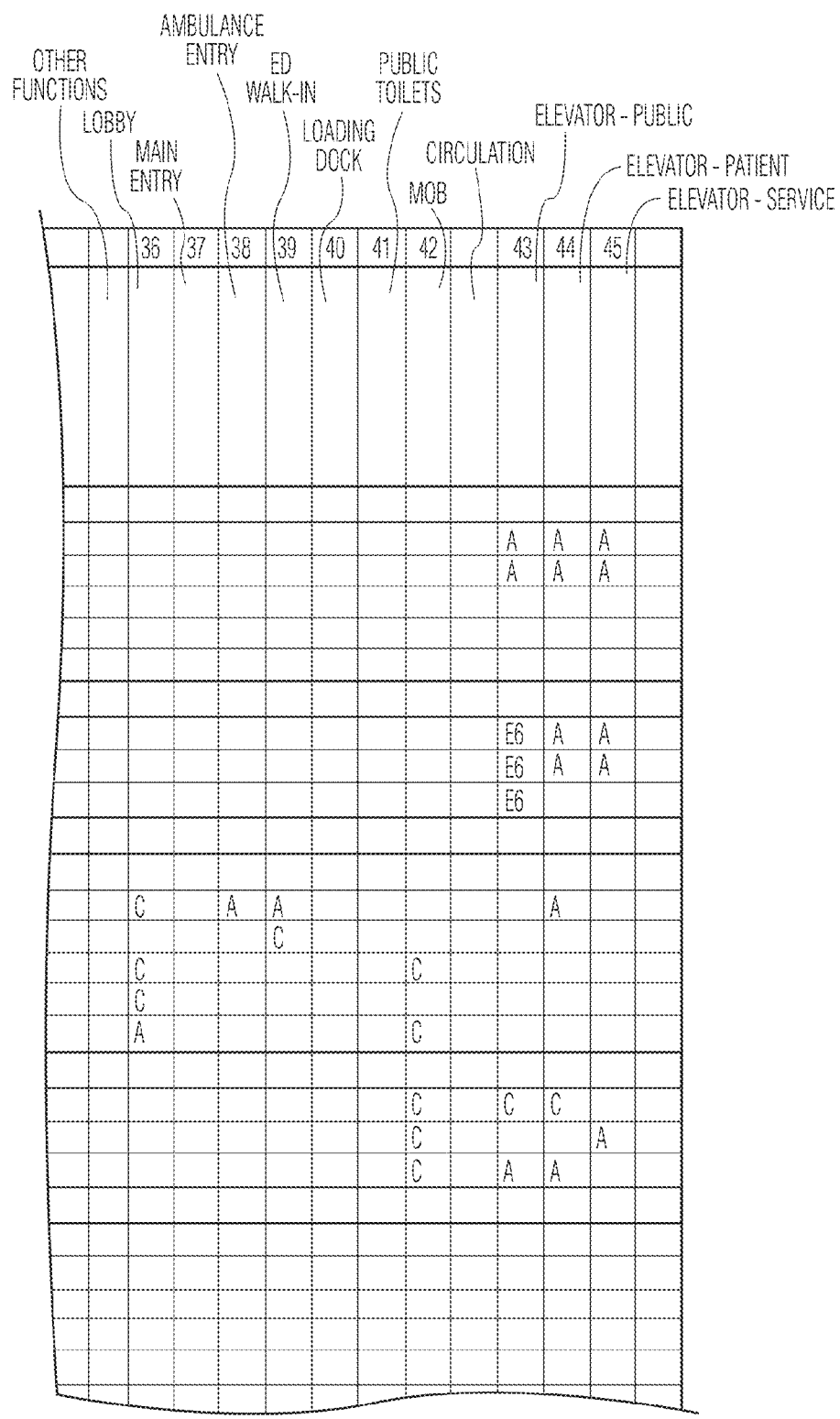
Figure 40G:
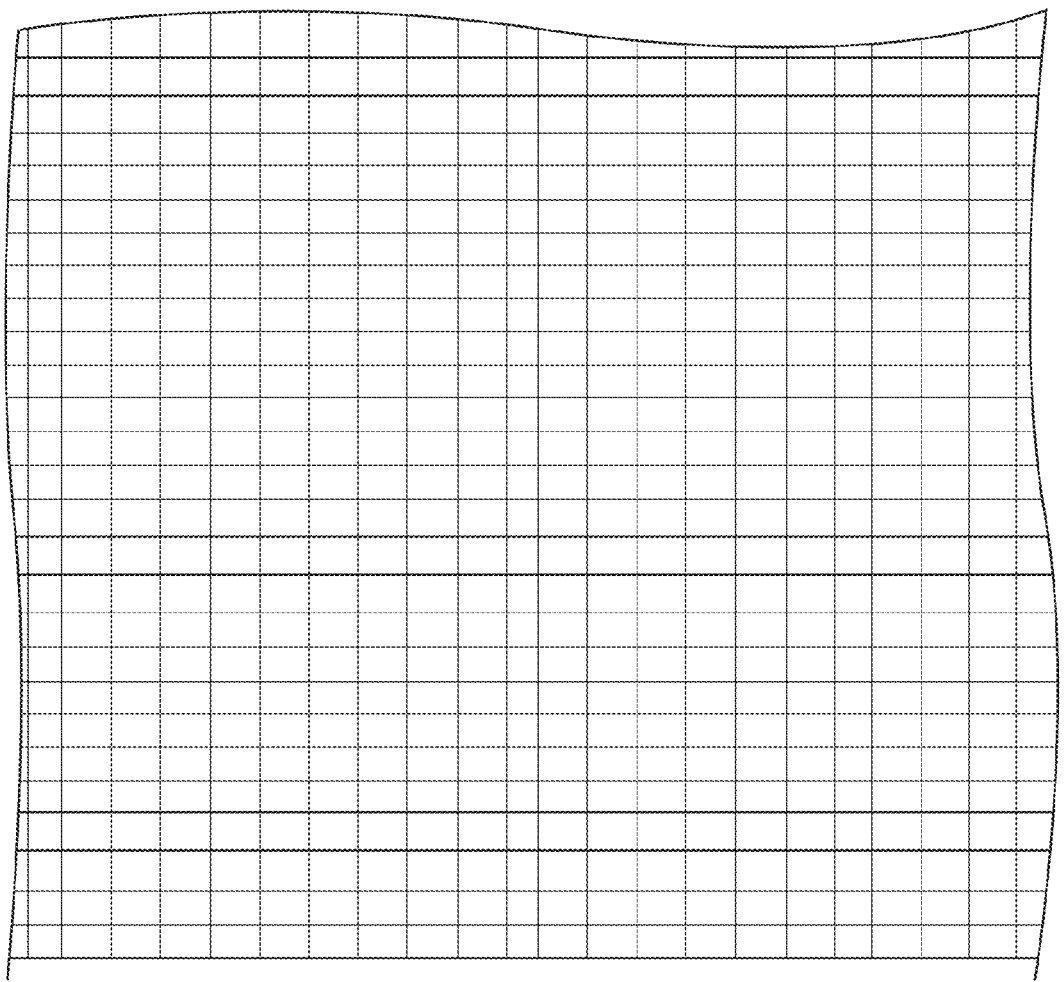
Figure 40H:
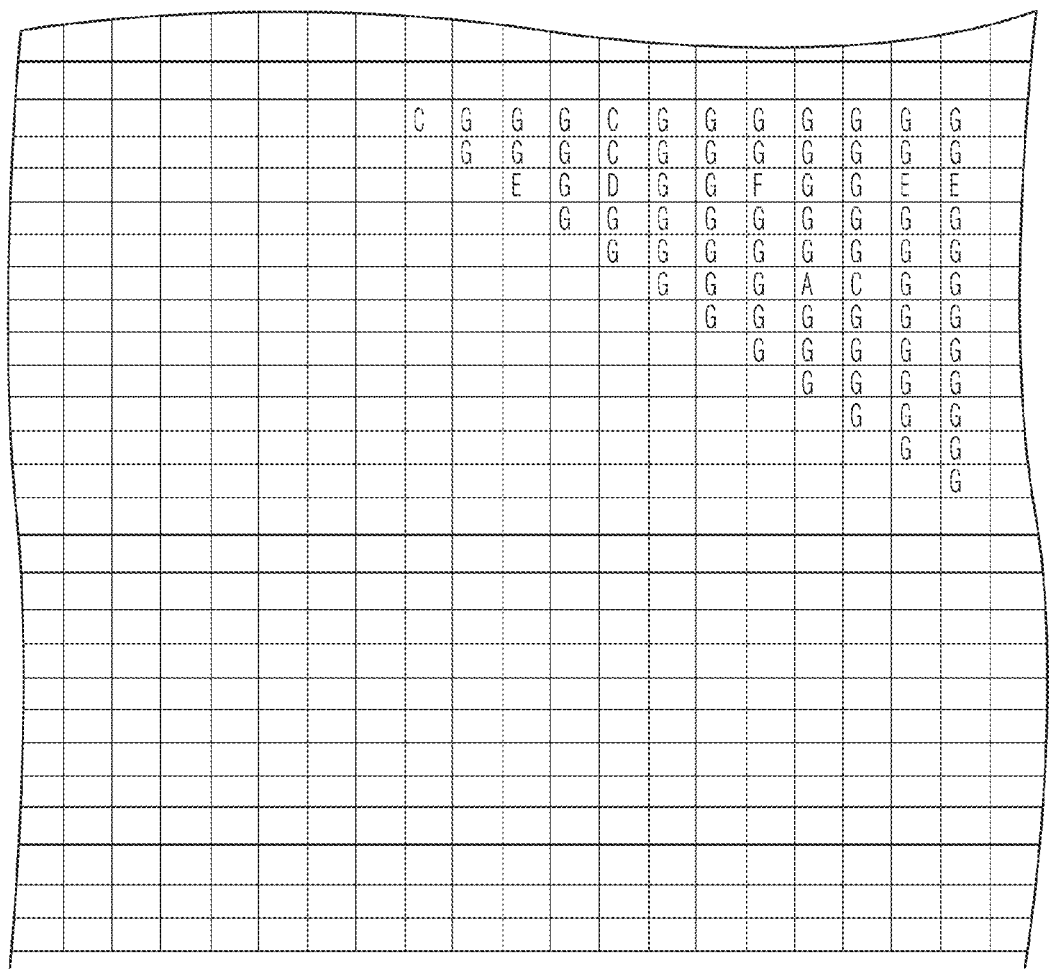
Figure 40I:
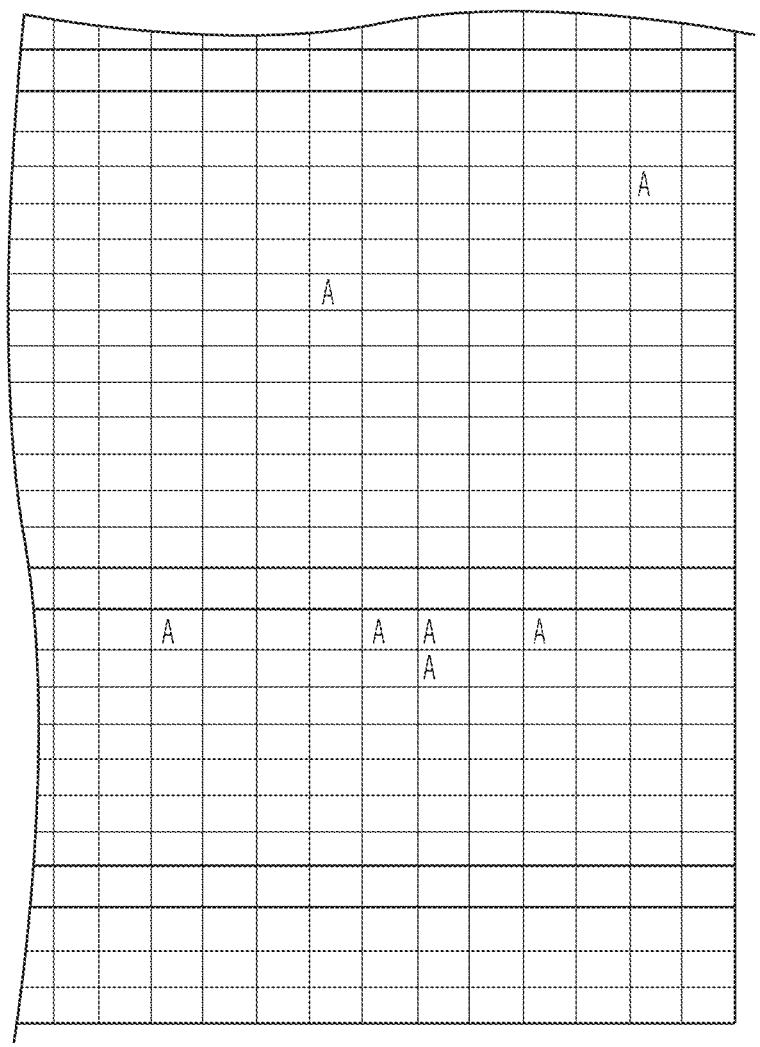
Figure 41B:
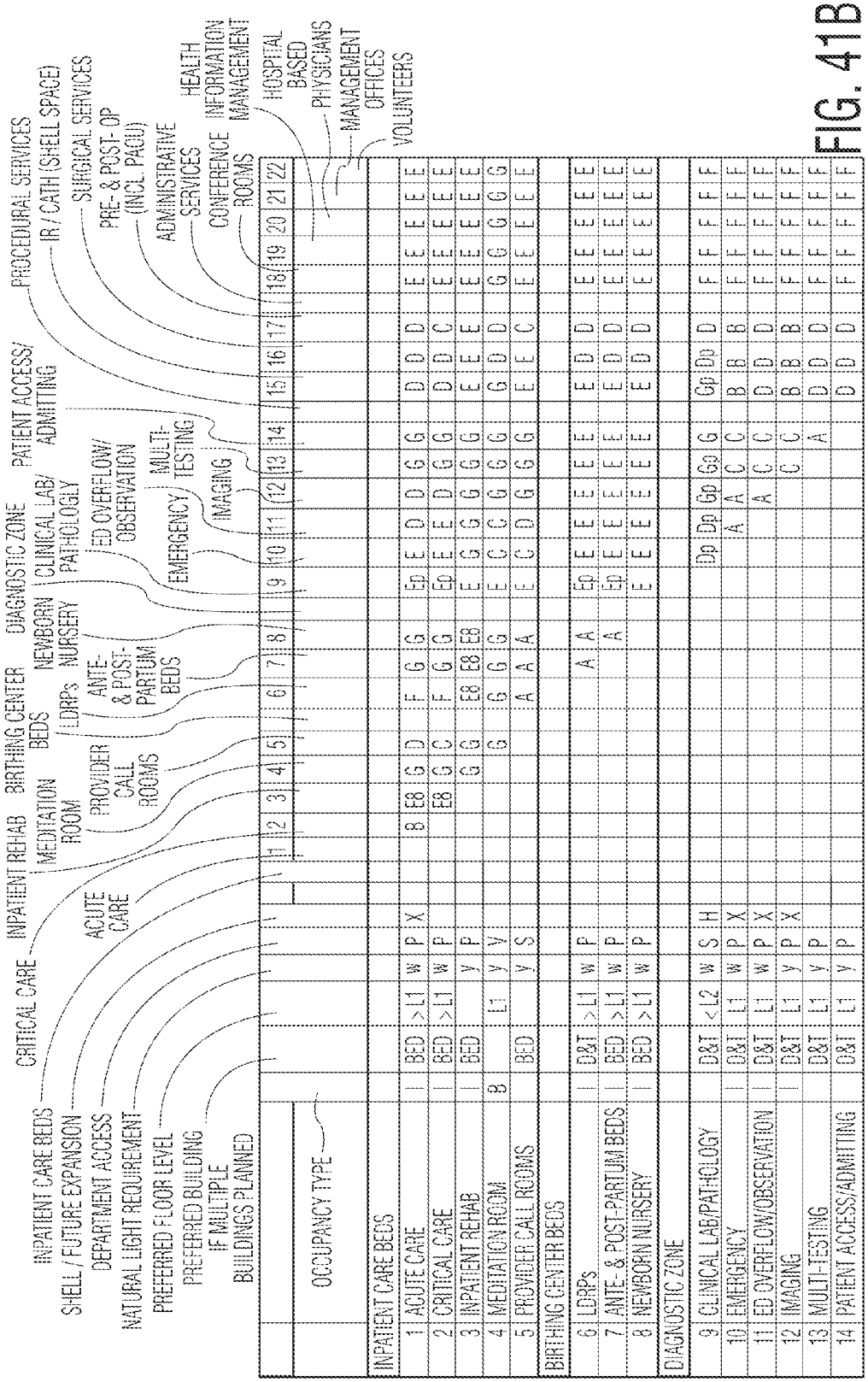

The process flow 3800 of FIG. 38 is now described in a more concrete example with reference to FIG. 39. FIG. 39 represents a block and stack tool 3820 that receives input related to "department blocks," "building mass," and "circulation pattern," and outputs at least one block and stack arrangement 3910 in which the building massing configuration and the location of the department blocks within the building massing configuration are spatially defined. The block and stack output can be used to produce a more detailed spatial arrangement (SA), e.g., including placed rooms and/or a system integration (SI).

With reference to the "department blocks" input, a particular set of department blocks 3912 is specified. The set of department blocks is graphically represented by the blocks 3914, where each block represents a separate department block. In the embodiment of FIG. 39, relative sizes of the department blocks are representative of the actual spatial dimensions of the department blocks. The functional groupings corresponding to the department blocks of FIG. 39 are "function_admin" (4 blocks), "function_bldg" (5 blocks), "function_clinical_support" (5 blocks), "function_drug_prep" (1 block), "function_exam" (1 block), "function_food_prep" (2 blocks), "function_imaging" (1 block), "function_lab" (1 block), "function_observation" (1 block), "function_patient" (10 blocks), "function_prepost" (1 block), and "function_treatment" (3 blocks), where the functional descriptive terms relate to the type of functions supported by the department blocks. Note that different department blocks can have the same functional grouping.

In the block and stack operation, it is expected that each department block will be placed within the building massing configuration.

With reference to the "building mass" input, a particular building massing configuration 3916 is specified for this particular block and stack operation. For example, the building massing configuration has the name "Test Shell-2," it is formed of 28'×28' bays, and it has a Building Gross Square Footage (BGSF) of 236,828. The building massing configuration of Test Shell-2 includes a "diagnostic and treatment" (D&T) portion, a "bed building" portion, and a "connector" portion, with each portion ranging from 3-5 stories/floors. In an embodiment, the building massing configuration was selected from a library of building massing configurations based on pre-filtering criteria as described above. In other embodiments, multiple different building massing configurations from the library of building massing configurations are evaluated by the block and stack tool in the block and stack operation.

With reference to the "circulation pattern" input, a particular circulation pattern 3918 is provided. In the embodiment of FIG. 39, the circulation pattern is a building wide circulation pattern that is indicated by the cross-hatching. The circulation pattern may define the overall circulation pattern within the building massing configuration, the location of travel corridors, the location of building entries/exits, stairs, elevators, shafts, and the structural column pattern. In an embodiment, circulation patterns define the horizontal circulation (e.g., corridors on the same floor) and vertical circulation (e.g., stairways, elevators, and shafts that provide access between floors).

Although not shown in FIG. 39, input to the block and stack tool 3820 also includes information related to adjacency. For example, the block and stack tool is provided with an adjacency matrix that characterizes the importance of spatial closeness between the department blocks, e.g., adjacency preferences. An example of an adjacency matrix is provided below with reference to FIGS. 40A-40I and 41A-41B.

Given the above described inputs, in an embodiment, the goal of the block and stack tool 3820 is to find an optimal, or best fit or best match, arrangement of all of the department blocks in the set of department blocks 3912 within the building massing configuration 3916 taking into consideration the circulation pattern 3918 and given specified adjacency preferences. In an embodiment, a cost function algorithm is implemented to find the best arrangement or arrangements, or best match, of the department blocks in terms of cost. For example, a best fit or best match is an arrangement that has a low cost relative to the costs of other arrangements, for example, a cost in the bottom 25% of all costs or a cost in the bottom 10% of all costs. In an embodiment, the best fit or best match arrangement is selected by a user of the BRP for display on a graphical user interface of a computer system. The selection may be made, for example, from a list of arrangements that are sorted by cost and/or a list of arrangements that are sorted by building massing configuration and cost.

An implementation of a cost function algorithm is now described. As stated above, the cost function algorithm is used to find spatial arrangements that have a relatively low cost. In an embodiment, the cost function is expressed as:

$$\text{Cost} = \Sigma\text{constraint costs} + \Sigma\text{violation costs} + \Sigma\text{overlap costs} + \Sigma\text{excess capacity costs} + \Sigma\text{excess perimeter costs}.$$

In the cost function expression, the "constraint costs" parameter relates to the adjacency preferences of the department blocks. That is, a pair of blocks has an associated cost depending on how close or how far the two blocks are placed from each other. In an embodiment, the costs are characterized by adjacency type and given a value in the range of 0 to 100, where a 0 cost is the most desirable, e.g., meets the adjacency preference, and 100 is the least desirable, e.g., doesn't meet the adjacency preference. This cost parameter leads to arrangements that reflect the adjacency preferences of the department blocks.

The "violation costs" parameter is a parameter that relates to a violation of a specific block assignment. For example, a department block can be specifically assigned to a particular building or portion of the building and a violation occurs if the department block is not placed as assigned. In another example, a department block can be required to be located entirely on the same floor and a violation occurs if subsets of the department block are placed on different floors. This cost parameter leads to arrangements that honor location and floor assignments.

The "overlap costs" parameter relates to whether or not placed department blocks spatially overlap with each other on the same floor. For example, a high cost is registered if two department blocks are placed in a building such that boundaries of the department blocks spatially overlap with each other. This cost parameter leads to arrangements in which department blocks do not overlap.

The "excess capacity costs" parameter relates to whether or not the footprint area of placed blocks exceeds the available footprint area as defined by the building massing configuration. For example, a high cost is assigned when the total area of the placed department blocks exceeds the available footprint area. This cost parameter leads to arrangements in which the building massing configuration is not overpopulated with department blocks. This cost parameter can also lead to selection of building massing configurations from the library of building massing configurations that fit the "program" of the building.

The "excess perimeter costs" parameter relates to whether or not the window perimeter needs of placed department blocks exceed the available window perimeter of the corresponding floor/story. A higher cost is given to arrangements in which the window perimeter needs of placed department blocks exceed the available window perimeter of the corresponding floor/storey. This cost parameter leads to an arrangement in which the need for window space is met.

The relative magnitude of the above described cost parameters determines the degree of influence that each parameter has on the total cost of a particular arrangement. In an embodiment, the cost parameters are ordered from lowest-cost to highest cost as: constraint costs, violation costs, overlap costs, excess capacity costs, excess perimeter costs. The magnitude of the cost parameters can be controlled by assigning cost values, or weights, to the parameters.

In addition to the cost structure, a technique for identifying the possible locations of each individual department block is implemented. The technique involves taking a particular building massing configuration and breaking each floor of the building massing configuration into a set of possible sub-rectangles. For example, sub-rectangles of a building massing configuration are enumerated such that each sub-rectangle has a unique index with a corresponding location and spatial dimensions. For example, a floor plan having a 3×2 grid of 30'×30' bays has three columns (0, 1, 2) and two rows (0, 1) of bays. With a sub-rectangle size of one bay, there are 16 possible sub-rectangles, each with a unique index, location, and spatial dimensions. For example, the 16 possible sub-rectangles can be identified as:

| Shape | Lower Left | Upper Right | Index |
|---|---|---|---|
| 1 × 1 | 0, 0 | 0, 0 | 0 |
|  | 1, 0 | 1, 0 | 1 |
|  | 2, 0 | 2, 0 | 2 |
|  | 1, 0 | 1, 0 | 3 |
|  | 1, 1 | 1, 1 | 4 |
|  | 2, 1 | 2, 1 | 5 |
| 1 × 2 | 0, 0 | 1, 0 | 6 |
|  | 1, 0 | 2, 0 | 7 |
|  | 0, 1 | 1, 1 | 8 |
|  | 1, 1 | 2, 1 | 9 |
| 2 × 1 | 0, 0 | 0, 1 | 10 |
|  | 1, 0 | 1, 1 | 11 |
|  | 2, 0 | 2, 1 | 12 |
| 2 × 2 | 0, 0 | 1, 1 | 13 |
|  | 1, 0 | 2, 1 | 14 |
| 3 × 2 | 0, 0 | 2, 1 | 15 |

In a building that is designed to provide healthcare services, there may be hundreds to thousands of enumerated sub-rectangles. For each sub-rectangle, it is also possible to determine the corresponding sub-rectangle area and total window perimeter of the sub-rectangle. The enumerated sub-rectangles are stored as a data structure, where each sub-rectangle can be found through its unique index. Although enumerated sub-rectangles are described, sub-spaces with shapes other than rectangles are possible.

Once all of the sub-rectangles have been enumerated, each department block is compared to the set of enumerated sub-rectangles to see which sub-rectangles will support the department block. For example, the minimum area and perimeter requirements of a department block are compared to the area and perimeter of each sub-rectangle to find all of the sub-rectangles that meet the minimum requirements of the department block. Additional considerations may include the department block shape and any building/floor assignments. All of the sub-rectangles that meet the minimum requirements of a department block are identified as the set of valid sub-rectangles for that department block. The process is performed for each department block to produce a set of valid sub-rectangles for each department block. A set of department blocks and valid sub-rectangles can be provided as:
  Dblock 1—list of valid sub-rectangles for Dblock 1;
  Dblock 2—list of valid sub-rectangles for Dblock 2;
  Dblock 3—list of valid sub-rectangles for Dblock 3; and
  Dblock n—list of valid sub-rectangles for Dblock n.

In a building system with two main building portions and 27 department blocks, which are similar to the building system depicted in FIG. 39, the total number of sub-rectangles is 19,815. If all 27 department blocks have multiple valid sub-rectangles (that is, there are multiple locations within the building in which the department block could be located), the total possible number of department block arrangements quickly becomes a huge number. In this example, the number of possible arrangements can be on the order of $10^{54}$ different possibilities, which is too large a number to calculate the cost of each possible arrangement.

In an embodiment, the concept of a "genetic algorithm" is applied to find low cost arrangements. In the computer science field of artificial intelligence, a genetic algorithm (GA) is a search heuristic that mimics the process of natural evolution. This heuristic is used to generate useful solutions to optimization and search problems. Genetic algorithms belong to the larger class of evolutionary algorithms (EA), which generate solutions to optimization problems using techniques inspired by natural evolution, such as inheritance, mutation, selection, and crossover. In a genetic algorithm, a single "chromosome" is generated by assigning a value to each entity and multiple chromosomes are generated to explore a universe of possibilities. In the application of a genetic algorithm as described herein, each department block of a building's space program is assigned to a valid sub-rectangle to create a single chromosome. That is, each chromosome represents a specific department block arrangement within a specific building massing configuration, where the department blocks are identified by a unique sub-rectangle identifier. Two different chromosomes can be expressed as:
  Chromosome 1
    Dblock 1 (sub-rectangle 578);
    Dblock 2 (sub-rectangle 934);
    Dblock 3 (sub-rectangle 22);
    Dblock n (sub-rectangle 896);
  Chromosome 2
    Dblock 1 (sub-rectangle 35);
    Dblock 2 (sub-rectangle 874);
    Dblock 3 (sub-rectangle 49);
    Dblock n (sub-rectangle 741).

In an embodiment, an initial set of chromosomes, e.g., 200, is generated for a particular space program. The initial set of chromosomes may be randomly generated by randomly selecting a valid sub-rectangle for each department block. A chromosome fitness value is calculated for each chromosome to quantify the cost of the chromosome. The chromosome cost is similar to the above-described cost function, and can be expressed as:

$$\text{Chromosome Fitness} = \Sigma\text{constraint costs} + \Sigma\text{violation costs} + \Sigma\text{overlap costs} + \Sigma\text{excess capacity costs} + \Sigma\text{excess perimeter costs};$$

where the chromosome fitness value of a particular chromosome represents the "cost" of the chromosome's corresponding spatial arrangement (e.g., placement of department blocks within a particular building massing configuration). With such a large number of possible different chromosomes, it is unlikely that the first set of chromosomes is near to the best fitness value (e.g., the lowest cost or a low cost relative to costs of the other chromosomes). In order to improve the fitness values and move towards a best fitness value, the chromosome fitness values that are calculated for the initial set of chromosomes are sorted and then random pairs of chromosomes are selected and new chromosomes are generated. The new chromosomes are generated through, for example, crossover and mutation using heuristics. Chromosome fitness values are calculated for the offspring chromosomes and the offspring chromosomes (and corresponding fitness values) are added to the set, while keeping the size of the set fixed, e.g., at 200, by removing the chromosomes with the worst fitness values. The process of generating new offspring chromosomes can be repeated until improvement of the chromosome fitness values (e.g., a reduction in cost) diminishes to a satisfactory level. At that point, the most desirable chromosomes, e.g., those with the lowest fitness value (lowest cost), can be selected, displayed on a graphical user interface, saved in the BRP, and/or further examined. In an embodiment, the chromosomes with the lowest fitness values represent the best matches between the types and volumes of services and the spatial patterns. At any point, adjustments can be made to any of the inputs and the block and stack process can be repeated.

An implementation of an embodiment of the block and stack flow diagram of FIG. 39 is now described. FIG. 40 (presented in sub-portions 40A-40I) depicts an adjacency matrix that identifies the adjacency type between pairs of department blocks. FIG. 41 (presented in sub-portions 41A-41B) is an expanded view of a portion of the adjacency matrix of FIG. 40. With reference to FIG. 41, the adjacency type between the acute-care department block (row 1) and the critical care department block (column 2) is adjacency type "B." In the embodiment of FIGS. 40 and 41, the adjacency matrix includes other cost parameters, such as building assignments, floor assignments, and natural lighting (window) requirements, which can be utilized in the cost function as described above.

FIG. 42 depicts an expanded view of the building massing configuration 3916 of FIG. 39. The building massing configuration of FIG. 42 includes a building system with a "diagnostic and treatment" (D&T) portion 4220, a "bed building" portion 4222, and a "connector" portion 4224, with each portion ranging from 3-5 stories/floors. The building massing configuration is formed of 28'×28' bays and has 236,828 BGSF. In an embodiment, details of the building massing configuration are stored in a library of building massing configurations as described above.

Figure 43:
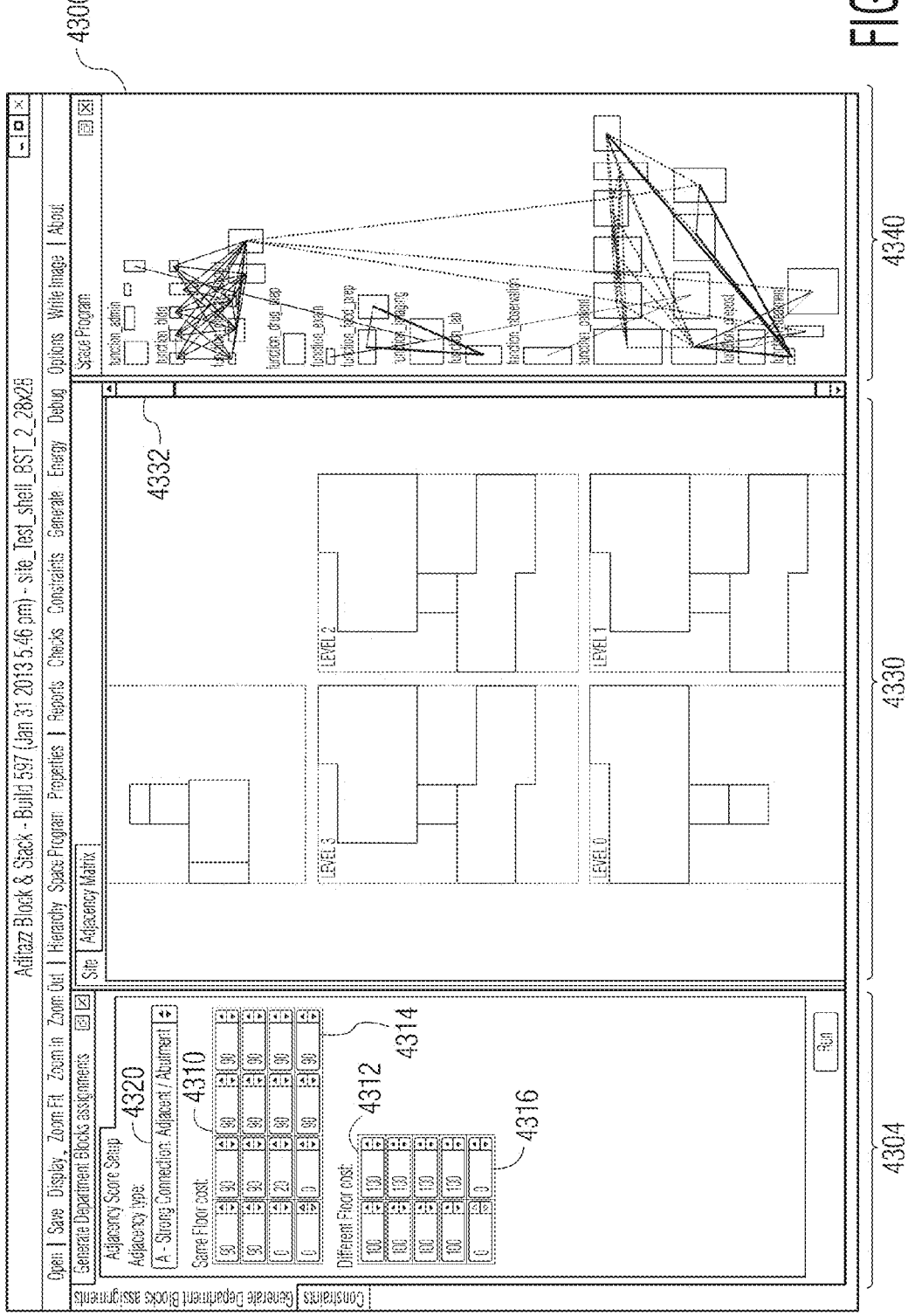
FIG. 43 depicts an embodiment of a graphical user interface of the block and stack tool.

FIG. 43 depicts an embodiment of a graphical user interface 4300 of the block and stack tool. The left side of the graphical user interface includes an input graphical user interface 4304 for setting adjacency costs. For example, the "Same Floor" and "Different Floor" adjacency costs are provided in matrices 4310 and 4312 of adjustable fields 4314 and 4316, e.g., fields that are adjustable by up/down arrows or by direct input. With respect to the "Same Floor" cost, the cost associated with placement of two different blocks is distributed as indicated relative to the lower left menu field. For example, the matrix of same floor costs corresponds to spatial relationships relative to the lower left corner of the matrix. With reference to FIG. 43, costs "0" and "20" are entered into the adjustable fields for locations in the matrix that are relatively close to the lower left corner and costs of "90" are entered into the adjustable fields for all of the other locations in the matrix. With respect to the "Different floor" cost, the cost associated with placement of two different department blocks on different floors is indicated relative to the lower left adjustable field. For example, the five rows of costs correspond to five floors of the building and the two rows correspond to two different floor access features (e.g., different stairwells or elevators in the building). In an embodiment, the adjacency costs are selectable numeric values, e.g., values from 0 to 100, where 0 represents a relatively low cost and 100 represents a relatively high cost. The adjacency costs can be adjusted individually for each adjacency type using the drop/pull down menu. In the embodiment of FIG. 43, the adjacency type is selected from the drop/pull down menu 4320 as adjacency type "A," where the adjacency types identified in FIGS. 40A-40I are included as selectable items in the drop/pull down menu of adjacency types.

The center of the graphical user interface 4300 includes a floor plan graphical user interface 4330 that identifies the floor plan outline of each floor of the building massing configuration of FIG. 42. At this point, the department blocks have not been placed within the building. The floor plan graphical user interface includes a scroll bar 4332 that enables the floor plan of each floor to be viewed if there is not enough room in the current view.

The right side of the graphical user interface 4300 includes a space plan graphical user interface 4340 that identifies the department blocks that are to be placed within the floors of the building massing configuration as displayed in the floor plan graphical user interface 4330 of the graphical user interface. In an embodiment, the different department blocks are color-coded and labeled. For example, each department block is displayed in a different color. In the embodiment of FIG. 43, the adjacency types are indicated by, for example, the color and/or type of connecting lines. For example, the coded adjacency lines help to graphically display the adjacency preferences of the different department blocks.

Figure 44:
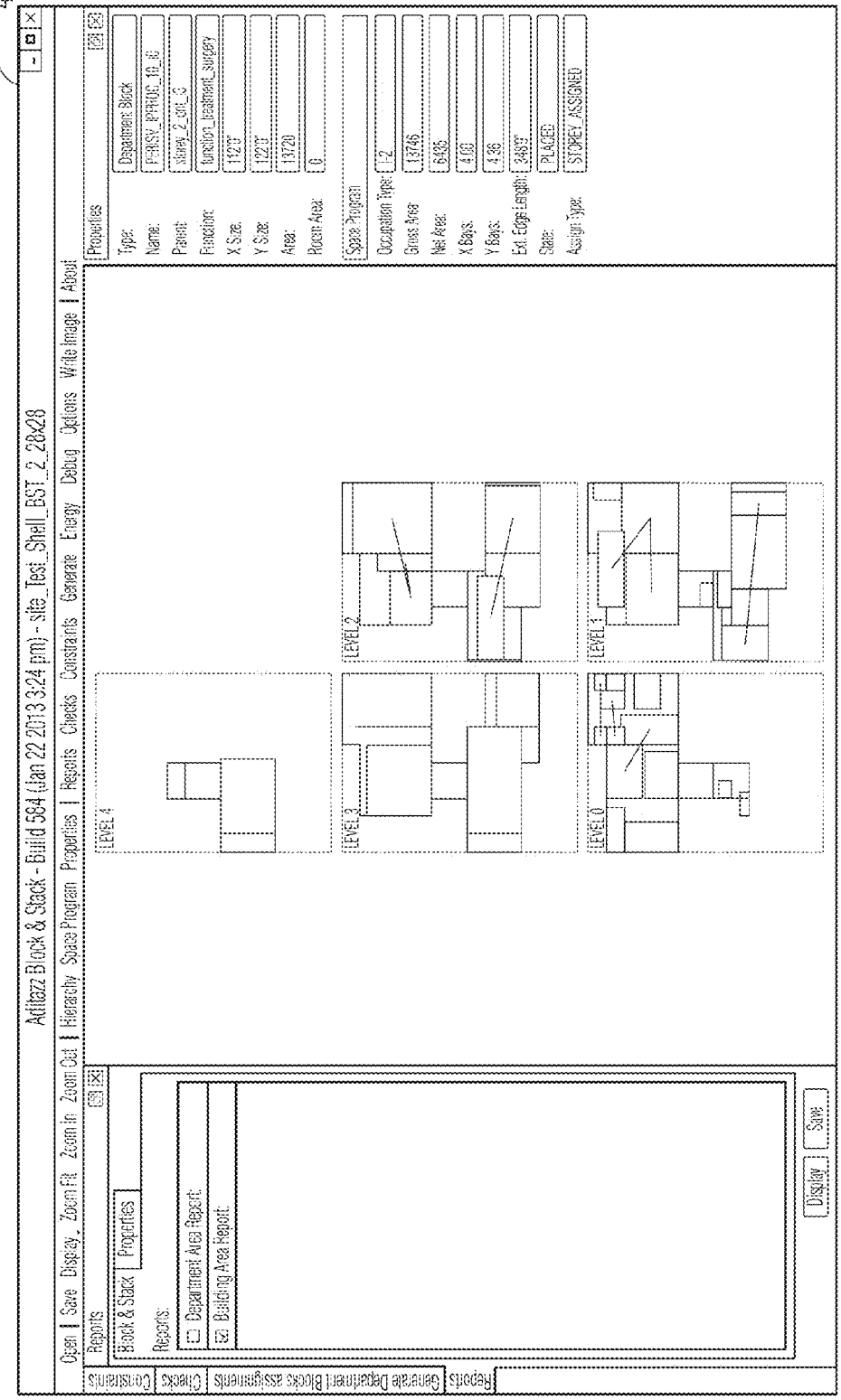
FIG. 44 is a graphical user interface that depicts a selected one of the arrangements of the department blocks within the building.

After the block and stack tool 3820 performs the placement operation, which includes implementing the above described cost function algorithm, the different department blocks are placed in a building having a specific building massing configuration. For example, each department block is located at a specific x and y position on a specific storey/floor of a building having a specific building massing configuration. FIG. 44 is a graphical user interface (which is displayed on a display of a computer system) that depicts a selected one of the arrangements of the department blocks within the specific building massing configuration. In an embodiment, the left side of the graphical user interface includes an input graphical user interface 4404 that enables the input of control information, such as information related to reports, department block assignments, checks, and constraints. In an embodiment, the center of the graphical user interface includes a floor plan graphical user interface 4430 that graphically depicts a spatial arrangement of department blocks within a specific building massing configuration. In the embodiment of FIG. 44, the floor plan graphical user interface graphically depicts the placement of department blocks within each floor of the building massing configuration 3916 shown in FIG. 42. In an embodiment, the right side of the graphical user interface includes an information graphical user interface 4440 that displays information about, for example, properties of department blocks and information about the space program.

In an embodiment, an arrangement is selected based on its cost from a list of arrangements that is sorted and ordered by increasing cost. It should be understood that FIG. 44 represents only one of multiple possible arrangements that can be generated using the block and stack tool. In an embodiment, the arrangement of FIG. 44 is the arrangement that has the lowest cost, e.g., the lowest chromosome fitness value, of the generated arrangements. Of course, multiple different arrangements can be selected by a user, displayed, saved, and evaluated as desired. As described above, the block and stack tool can place a set of department blocks in multiple different building massing configurations that are stored in the library of building massing configurations. In one embodiment, a set of filtered building massing configurations is established based on various criteria as described above and the same set of department blocks is placed in each different building massing configuration of the filtered set of building massing configurations. Placing the department blocks in multiple different building massing configurations enables multiple different building massing configurations to be rapidly evaluated on a cost basis and compared amongst the different building massing configurations in the set.

Figure 45:
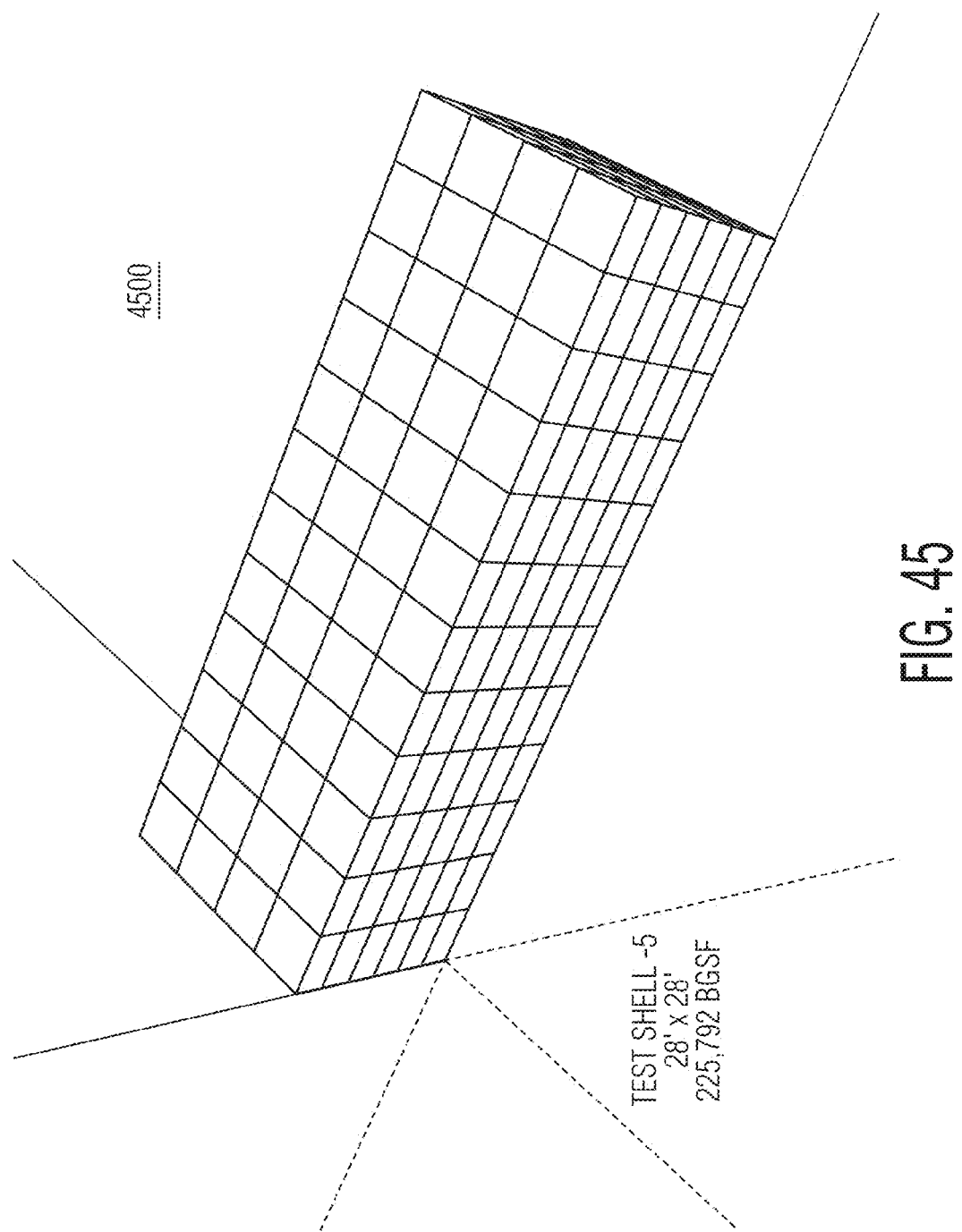
FIG. 45 depicts an alternative building massing configuration that could be evaluated to incorporate the same set of department blocks as those incorporated into the building massing configuration of FIG. 39.
Figure 46:
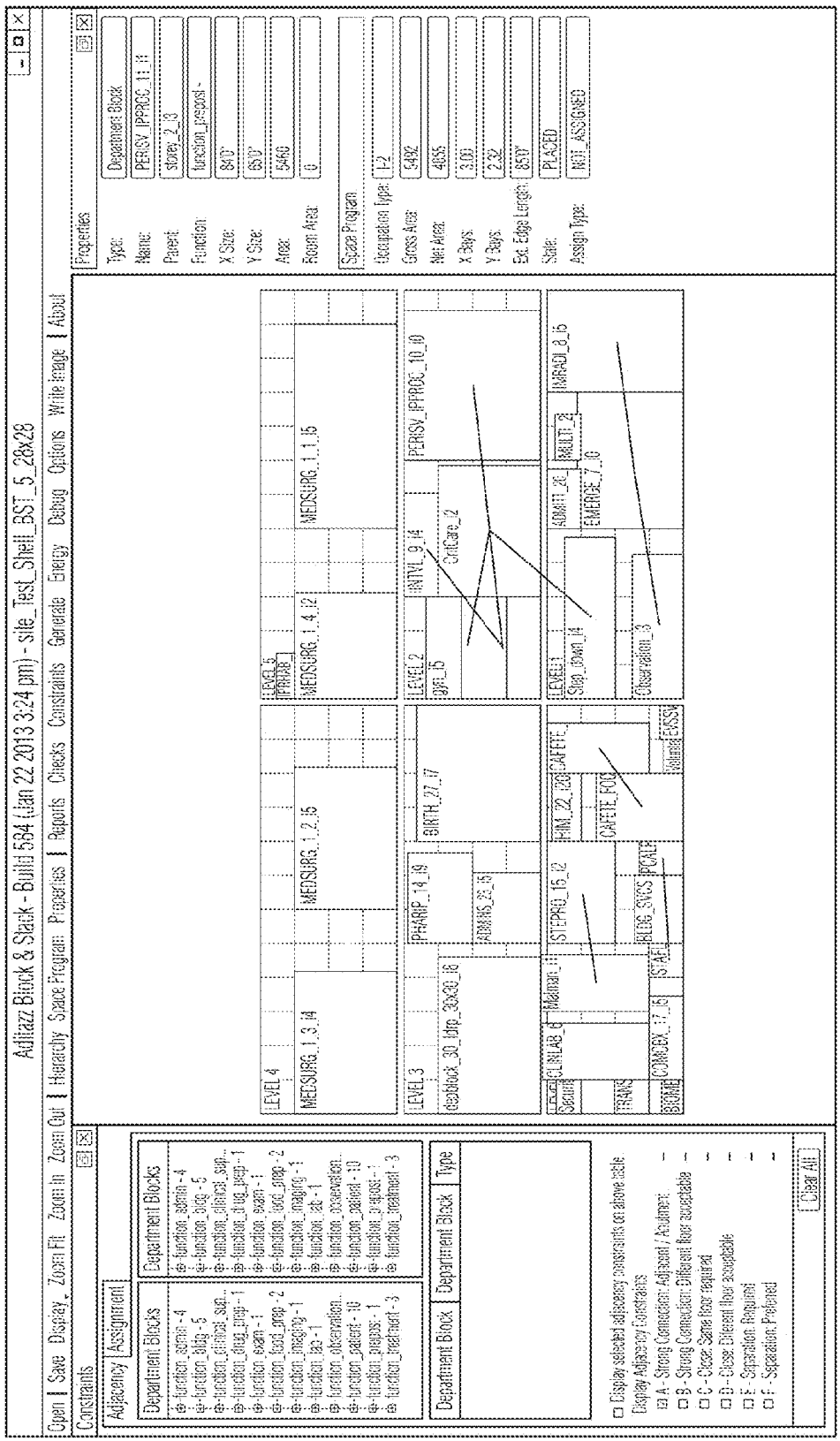
FIG. 46 is a graphical user interface that depicts a selected one of the arrangements of the department blocks within the building floors of the building massing configuration of FIG. 45.

FIG. 45 depicts an alternative building massing configuration 4500 that could be evaluated to incorporate the same set of department blocks as those incorporated into the building massing configuration 3916 of FIGS. 39 and 42. The building massing configuration of FIG. 45 includes a single rectangular building, referred to as "Test Shell-5," and having dimensions of Bx=12, By=4, and Bz=6, with each bay being 28'×28'×15', for a total of 225,792 BGSF. FIG. 46 is a graphical user interface that depicts a selected one of the arrangements of the department blocks within the building floors of the building massing configuration of FIG. 45. For example, the arrangement of FIG. 46 was selected from a listing of arrangements (e.g., chromosomes) that was ordered by fitness value. In an embodiment, the left side of the graphical user interface includes an input graphical user interface 4604 that enables the input of control information, such as information related to constraints related to department block adjacency and/or department block assignment. In an embodiment, the center of the graphical user interface includes a floor plan graphical user interface 4630 that graphically depicts a spatial arrangement of department blocks within a building massing configuration. In the embodiment of FIG. 46, the floor plan graphical user interface graphically depicts the placement of department blocks within each floor of the building massing configuration 4500 shown in FIG. 45. In an embodiment, the right side of the graphical user interface includes an information graphical user interface 4640 that displays information about, for example, properties of department blocks and information about the space program.

Because the generated block and stack arrangements have certain spatial dimensions, various reports and analysis can be performed. FIG. 47 depicts a graphical user interface 4700 of a report that identifies certain characteristics of the block and stack arrangement of FIG. 44 within the building massing configuration 3916 of FIG. 42. In FIG. 47, the top portion 4750 of the graphical user interface is a table that includes statistics for the "bed building" portion 4222 of the building massing configuration, the middle portion 4752 of the graphical user interface is a table that includes statistics for the "D&T" portion 4220 of the building massing configuration, and the bottom portion 4754 of the graphical user interface is a table that includes statistics for the "connector" portion 4224 of the building massing configuration. In an embodiment, the statistics include overall BGSF, external wall area, corridors area, designed department net square feet (DNSF), designed department gross square feet (DGSF), utilization, and available area.

Figure 48:
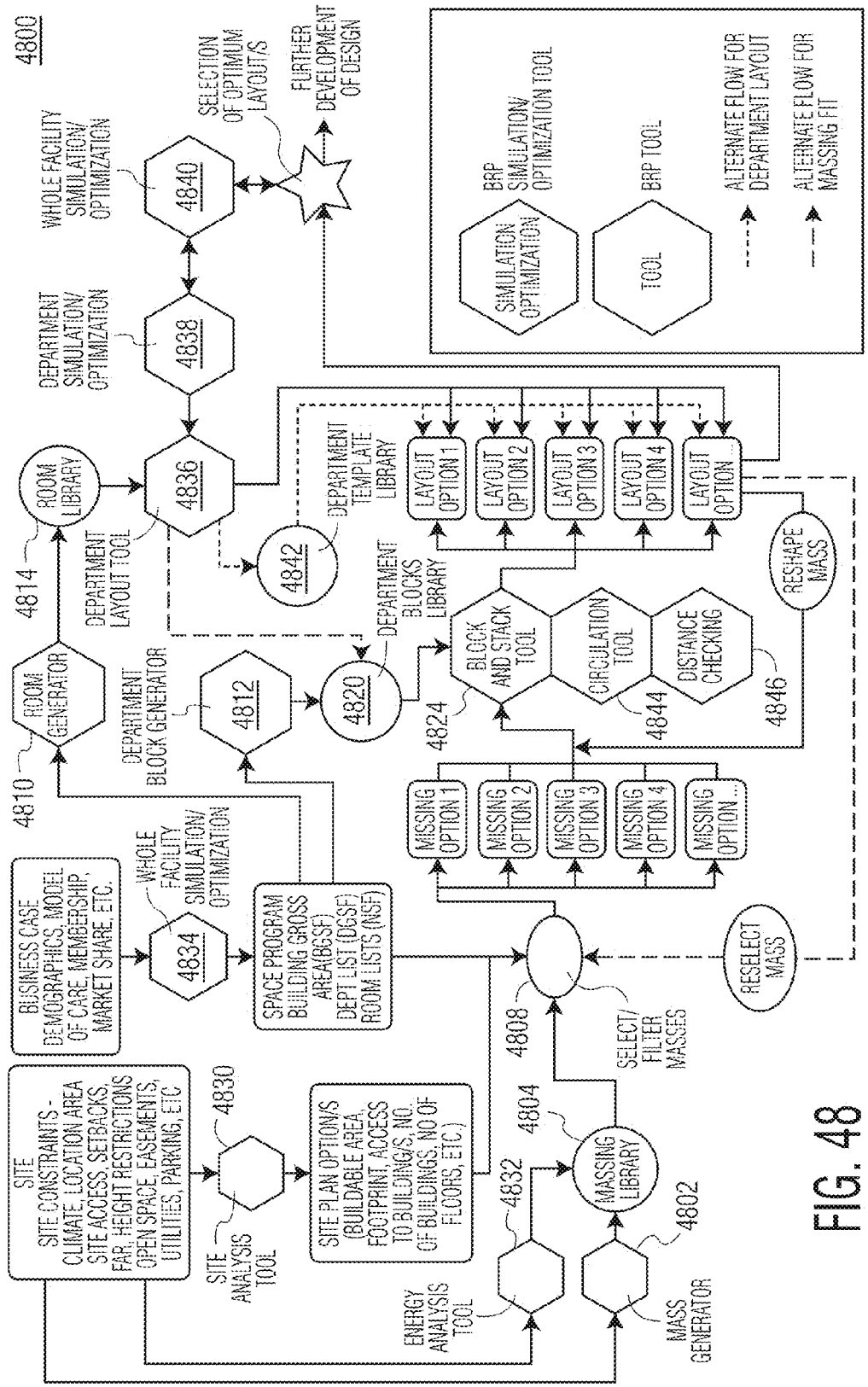
FIG. 48 is a process flow diagram of a method for realizing a building system.

FIG. 48 is a process flow diagram 4800 of a method for realizing a building system. FIG. 48 includes a "mass generator" 4802 that is similar to the building massing generation system 3702 of FIG. 37, a "massing library" 4804 that is similar to the building massing library 3706 of FIG. 37, a "select/filter masses" module 4808 that is similar to the query engine 3716 of FIG. 37, a "room generator" 4810 and "department block generator" 4812 that are similar to the room and department generation block 3810 of FIG. 38, a "room library" 4814 and "department blocks" library 4820 that are similar to the "library of rooms and depts." 3812 of FIG. 38, and a "block and stack tool" 4824 that is similar to the block and stack tool 3820 of FIG. 38. The process flow diagram of FIG. 48 also depicts a site analysis tool 4830. FIG. 48 illustrates that multiple different building massing configurations (massing options) can be provided as input to the block and stack tool to create multiple spatial arrangements (layout options). In an embodiment, the multiple different building massing configurations are evaluated in parallel by the block and stack tool using cloud-based HP2 computing resources to quickly and efficiently evaluate multiple different building massing configurations.

As described above, pattern matching can be implemented using a cost function algorithm to find spatial arrangements that have relatively low cost. An embodiment of a cost function algorithm is described in more detail below.

In general, inputs to the cost function algorithm include: Parti (number of buildings, shape, structural grid and number of stories for each building); program (size and content of each department block); allowed variations for stories and department blocks; block shape variants based on the building structural grid, coefficients to take into account reserved space for circulation (corridors, elevators, stairs, shafts) as well as future expansion, and preliminary horizontal (corridors) and vertical (shafts) circulation (if provided), defined as blockages. In an embodiment, outputs include several suggested solutions for architects/medical planners to evaluate. In an embodiment, each solution contains: selection of building massing configurations, assignment of department blocks to building massing configurations and stories within the building massing configurations; relative positions of department blocks within the stories and their suggested dimensions; graphical and textual representations of block and stack diagrams; distance, travel time, and behavior simulation reports; area reports; and a modified BRP model, which includes block and stack results.

A mathematical formulation of the block and stack optimization problem satisfying the specified constraints is presented below. The mathematical model relies on a simplified geometry representation—stories and department blocks are represented as rectangles. More complex stories geometries could be accommodated.

1. Input data.
  a) Buildings
    $B_i$, i∈[0, NB],
    where NB is number of buildings in the facility.
  b) Storeyis
    $S_{ij}$, i∈[0, NB], j∈[0, NS(i)],
    where NS(i) is number of storeys in building i in the facility.
    The following data are defined for each storey (rectangular approximation):
  $XS_{ij}$—X size;
  $YS_{ij}$—Y size;
  $ZS_{ij}$—Z size;
  $(x_{ij}, y_{ij}, z_{ij})$—storey location (origin) in the facility (global) system of coordinates;
  $R_{ij}$—orientation of the storey (if required). Most likely it will be 0.
  c) Department Blocks
    $D_k$, k∈[0, ND],
    where ND is number of department blocks in the facility.
  The following data are defined for each department block (rectangular approximation):

AD(k)—Department Block area;
ND(k)—number of variants of the block (different aspect ratio) based on the structural grid size;
$XD_{k1}$—X size of the 1 variant of department block k;
$YD_{k1}$—Y size of the 1 variant of department block k; ($XD_{k1} * YD_{k1} = AD(k)$)
$ZD_{k1}$—Z size of the 1 variant of department block k;
$1 \epsilon [0, ND(k)]$.
The additional data used for optimization criteria calculation:
$a_{mn}$—department block adjacency coefficient. The higher the coefficient the stronger the attraction between the department blocks $D_m$ and $D_n$. Negative $a_{mn}$ indicates repulsion between department blocks.
$c_{ij}(k)$—attraction coefficient between department block $D_k$ and storey $S_{ij}$.
d) Fixed Blockages (corridors, shafts, cut-outs, fences) $BL_1$, $1 \epsilon [0, NBL(i,j)]$,
where NBL(i,j) is number of blockages in the storey $S_{ij}$.
$XBL_1(i,j)$—X size of the blockage BL(i,j);
$YBL_1(i,j)$—Y size of the blockage BL(i,j);
$(x_1,y_1,z_1)$—location(origin) of the blockage in the $S_{ij}$ local system of coordinates;
$P_{ij}(l)$—penalties for overlapping with blockage object 1 on the storey $S_{ij}$.
2. Optimization Variables
The goal of optimization is to find:
Assignment of department blocks to the stories:
$w_{ij}(k)$={1 if $D_k$ is assigned to the storey $S_{ij}$, 0 otherwise}
$(x_k,y_k,z_k)$—location (origin) of the department block in the $S_{ij}$ local system of coordinates;
$R_k$—orientation of the department block;
$l_k$—variant of the department block $D_k$.
3. Constraints
Sum of the departments assigned to the storey does not exceed area of the storey $$\sum_{k=1}^{k<=ND} w_{ij}(k) * AD(k) <= AS_{ij} \text{ (where } AS_{ij} = XS_{ij} * YS_{ij}\text{);}$$

Block is inside the storey
if $w_{ij}(k)=1$:
$x_k + XD_{k1} <= XS_{ij}$
$y_k + YD_{k1} <= YS_{ij}$
$ZD_{k1} <= ZS_{ij}$
Blocks within same storey do not overlap.
if $w_{ij}(m)=1$ and $w_{ij}(n)=1$:
$x_m + XD_{ml1} <= x_n$; $x_m - XD_{nl2} >= x_n$;
$y_m + YD_{ml1} <= y_n$; $y_m - YD_{nl2} >= y_n$;
where l1 and l2 are variants of department blocks $D_m$ and $D_n$, respectively
Predefined department block assignment to stories:
$w_{ij}(k)=1$
department block $D_k$ is assigned to the storey $S_{ij}$.
Predefined department block assignment to building:
$w_i(k)=1$
department block $D_k$ is assigned to the Building B.
Predefined (restricted) department block location and orientation
$x_{mink} <= x_k <= x_{maxk}$;
$y_{mink} <= y_k <= y_{maxk}$;
$R_k \epsilon [r_k]$,
Where $x_{mink}$, $x_{maxk}$ and $y_{mink}$, $y_{maxk}$ allowed ranges for x and y coordinates of $D_k$ department block. If $x_{mink}=x_{maxk}$ or $y_{mink}=y_{maxk}$ the respective coordinate of the block is fixed. $[r_k]$—allowed orientations for the block.
4. Optimization criteria
In an embodiment, the optimization goal of the block and stack operation is to minimize travelling time between departments, subject to adjacency constraints and to minimize the penalty for not placing department on the preferred storey (if specified):

$$\min \sum_{m=1}^{m<=ND} \sum_{n=1}^{n<=ND} a_{mn} * t_{mn} + \sum_{i,j} \sum_{k=1}^{k<=ND} c_{ij}(k) * d_{ij}(k) + \sum_{k=1}^{k<=ND} \sum_{l=1}^{l<=NBL(i,j)} p_{ij}(l) * A_{ij}(k,l),$$

where $a_{mn}$ and $c_{ij}(k)$ attraction coefficients defined in 3 c),
$p_{ij}(l)$ penalty for overlapping with blockage object 1 on the storey $S_{ij}$.
$w_{ij}(k)=1$,
$t_{mn}$—travel time between department blocks $D_m$ and $D_n$ (for typical traveler),
$t_{mn} = vh * dh_{mn} + vv * dv_{mn}$,
vh—horizontal speed,
$dh_{mn}$—horizontal distance between department blocks $D_m$ and $D_n$,
vv—vertical speed,
$dh_{mn}$—equivalent vertical distance between department blocks $D_m$ and $D_n$;
$d_{ij}(k)$—distance between department block $D_k$ and storey $S_{ij}$,
$d_{ij}(k) = dh_{ij}(k) + dv_{ij}(k)$,
$dh_{ij}(k)$—horizontal distance between department block $D_k$ and storey $S_{ij}$,
$dV_{ij}(k)$—equivalent vertical distance between department block $D_k$ and storey $S_{ij}$,
$A_{ij}(k,l)$—overlap of the department block $D_k$ and blockage BL(i,j).
In an embodiment, the block and stack tool is implemented in software using, for example, a computer described with reference to FIG. 18.
In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.
Although specific embodiments of the invention have been described and illustrated, the invention is not to be limited to the specific forms or arrangements of parts so described and illustrated. The scope of the invention is to be defined by the claims appended hereto and their equivalents.
In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.
Although specific embodiments of the invention have been described and illustrated, the invention is not to be limited to the specific forms or arrangements of parts so described and illustrated. The scope of the invention is to be defined by the claims appended hereto and their equivalents.

APPENDIX

Nomenclatures:

$N_s$ = Number of stories $B_x$ = Number of bays in X direction $B_y$ = Number of bays in Y direction $B_{fp}$ = Total number of bays in the footprint $B_e$ = Number of bays along the exposed perimeter $R_s = B_e/B_{fp}$ $EUI_n$ = Energy Use Index normalized with respect to the EUI of 2x2 bay 3 story building.

Formulations derived in this document are based on approximately 30,000 Energy Plus runs of a typical hospital environment. In order to determine the relative energy use index, nEUI, of various building massing options, the following parameters are varied but all others are fixed.

- Number of bays in X and Y directions ($B_x$, $B_y$)
- Void area expressed in terms of $B_x$, $B_y$, $H$ and $W$ in the diagrams appeared in this document
- Number of stories Each bay is set to 30'x30' for the EnergyPlus runs.

The formulas presented in this document have been verified with the EnergyPlus runs for the following ranges.

| | |
|---|---|
| • Number of floors: | 1 – 20 floors |
| • Minimum number of bays of narrow section: | 1 (no restriction) |
| • Minimum number of bays in X or Y direction of void area: | 1 (no restriction) |
| • Total square footage: | 1,000 sf ~ 1,000,000 sf |

Formulas for Single-Storey, Two-Storey and 3+ Storey Building

1. Footprint R (Rectangle)

$$EUI_n = \sum_{i=0}^{3}\left(C_i \cdot R_s^{\,i}\right) + e_c$$

where $$R_s = \frac{B_e}{B_{fp}}$$

$$B_e = 2 \times \left(B_x + B_y\right)$$

$$B_{fp} = B_x B_y$$

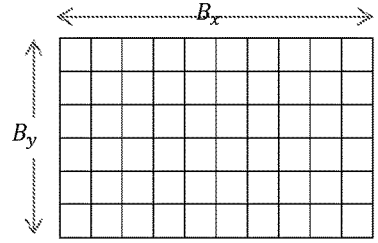

Figure A1a. Rectangular Shape Footprint

Table A1. Coefficients for Rectangular Shape Footprints

|  | 1 Storey | | | | 2 Stories | | | | 3+ Stories | |
|---|---|---|---|---|---|---|---|---|---|---|
|  | Bx > By | | Bx <= By | | Bx > By | | Bx <= By | | Bx > By | Bx <= By |
|  | Rs <= 2 | Rs > 2 | Rs <= 2 | Rs > 2 | Rs <= 2 | Rs > 2 | Rs <= 2 | Rs > 2 | | |
| $C_0$ | 0.5670 | -0.2316 | 0.6436 | 0.7833 | 0.4959 | 0.4529 | 0.4636 | 0.4993 | 0.4482 | 0.4377 |
| $C_1$ | -0.0146 | 0.6106 | -0.3841 | 0.2356 | 0.0654 | 0.0591 | 0.1531 | 0.2669 | 0.086 | 0.1031 |
| $C_2$ | 0.1294 | 0.0506 | 0.6620 | 0.0542 | 0.0864 | 0.0895 | 0.0551 | 0.0303 | 0.09367 | 0.1119 |
| $C_3$ | 0.0320 | -0.0124 | -0.1650 | -0.0046 | 0 | | 0 | | 0 | |
| $e_c$ | 0 | | 0 | | 0 | | 0 | | formula | |

$$e_c = 0 \qquad \text{for } N_s \leq 2$$

$$e_c = 0.002\sqrt{\frac{B_{fp}}{N_s - 2}} + e_d \qquad \text{for } N_s > 2$$

$$e_d = \frac{1}{B_y}\left(0.1 - \frac{0.288}{\sqrt{N_s - 2}}\right) \qquad \text{for } B_x \leq 2 \text{ and } B_y \leq 4$$

$$e_d = 0 \qquad \text{for others}$$

2. Footprint L $$EUI_n = \sum_{i=0}^{3}(C_i \cdot R_s^{\,i}) + e_c$$

where $$R_s = \frac{B_e}{B_{fp}}$$

$$B_e = 2 \times (B_x + B_y)$$

$$B_{fp} = B_x H + B_y W - WH$$

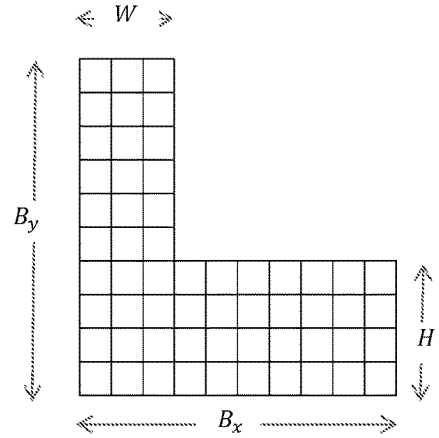

Figure A2a. "L" Shape Footprint

Table A2a. Coefficients for "L" Shape Footprints

|       | 1 Storey | 2 Stories | 3-20 Stories |
|-------|----------|-----------|--------------|
| $C_0$ | 0.5936   | 0.4904    | 0.4199       |
| $C_1$ | -0.1382  | 0.0832    | 0.1814       |
| $C_2$ | 0.3351   | 0.0853    | 0.01715      |
| $C_3$ | -0.0525  | 0         | 0.02082      |
| $e_c$ | 0        | 0         | formula      |

For $B_x \leq 2$ or $B_y \leq 2$ $$e_c = \sum_{i=0}^{3}(D_i \cdot N_s^{\,i})$$

Table A2b. Secondary Coefficients for "L" Shape Footprints

| $D_0$ | -0.2736   |
|-------|-----------|
| $D_1$ | 0.0628    |
| $D_2$ | -4.264E-03 |
| $D_3$ | 9.398E-05 |

For $B_x > 2$ or $B_y > 2$ $$e_c = 0.00167\sqrt{\frac{B_{fp}}{N_s - 2}}$$

3. Footprint Z $$EUI_n = \sum_{i=0}^{2}(C_i \cdot R_s^{i}) + e_c$$

where $$R_s = \frac{B_e}{B_{fp}}$$

$$B_e = 2 \times (B_x + B_y)$$

$$B_{fp} = B_x B_y - 2WH$$

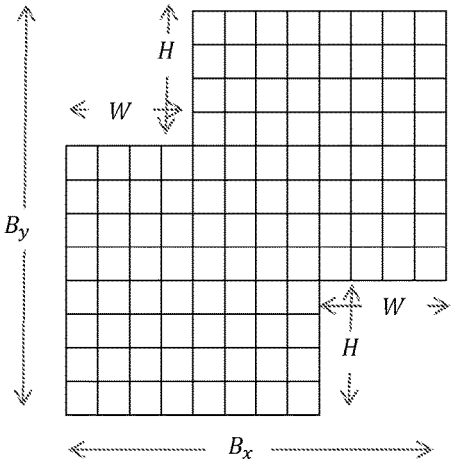

Figure A3a. "Z" Shape Footprint

Table A3. Coefficients for "Z" Shape Footprints

|  | 1 Storey | | 2 Stories | | 3+ Stories | |
|---|---|---|---|---|---|---|
|  | $Rs < 0.4$ | $Rs >= 0.4$ | $Rs < 0.4$ | $Rs >= 0.4$ | $Rs < 0.4$ | $Rs >= 0.4$ |
| $C_0$ | 0.7343 | 0.7638 | 0.6727 | 0.6925 | 0.655 | 0.645 |
| $C_1$ | -0.3412 | -0.1762 | -0.2909 | -0.1606 | -0.4158 | -0.1704 |
| $C_2$ | 0.7649 | 0.2157 | 0.6232 | 0.1558 | 0.8138 | 0.1641 |
| $e_c$ | 0 | 0 | 0 | 0 | formula | formula |

For $N_s > 2$ and $R_s < 0.4$ $$e_c = 0.0012 \sqrt{\frac{B_{fp}}{N_s - 2}}$$

For $N_s > 2$ and $0.4 \leq R_s < 1.25$ $$e_c = 0.004 \sqrt{\frac{B_{fp}}{N_s - 2}}$$

For $N_s > 2$ and $R_s \geq 1.25$ $$e_c = 0.075 \sqrt{\frac{N_s - 2}{B_{fp}}}$$

4. Footprint K $$EUI_n = \sum_{i=0}^{2}\left(C_i \cdot R_s^{\,i}\right) + e_c$$

where $$R_s = \frac{B_e}{B_{fp}}$$

$$B_e = 2 \times \left(B_x + B_y\right)$$

$$B_{fp} = B_x B_y - 3WH$$

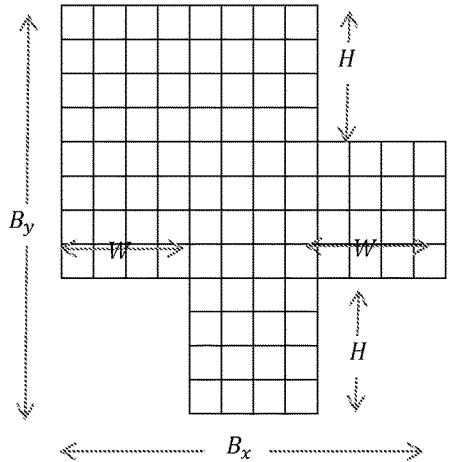

Figure A4a. "K" Shape Footprint

Table A4. Coefficients for "K" Shape Footprints

|  | 1 Storey | | 2 Stories | | 3+ Stories | |
| --- | --- | --- | --- | --- | --- | --- |
|  | Rs < 0.4 | Rs >= 0.4 | Rs < 0.4 | Rs >= 0.4 | Rs < 0.4 | Rs >= 0.4 |
| $C_0$ | 0.7199 | 0.7493 | 0.6651 | 0.6928 | 0.6628 | 0.6720 |
| $C_1$ | -0.2576 | -0.1391 | -0.2379 | -0.1291 | -0.4824 | -0.2119 |
| $C_2$ | 0.6466 | 0.1895 | 0.5373 | 0.1357 | 0.9273 | 0.1986 |
| $e_c$ | 0 | 0 | 0 | 0 | formula | formula |

For $N_s > 2$ and $R_s < 0.4$ $$e_c = 0.0015\sqrt{\frac{B_{fp}}{N_s - 2}}$$

For $N_s > 2$ and $0.4 \leq R_s < 1.25$ $$e_c = 0.002\sqrt{\frac{B_{fp}}{N_s - 2}}$$

For $N_s > 2$ and $R_s \geq 1.25$ $$e_c = 0.045\sqrt{\frac{N_s - 2}{B_{fp}}} - \frac{0.106}{\sqrt{N_s - 2}}$$

5. Footprint X $$EUI_n = \sum_{i=0}^{2}\left(C_i \cdot R_s^{\,i}\right) + e_c$$

where $$R_s = \frac{B_e}{B_{fp}}$$

$$B_e = 2 \times \left(B_x + B_y\right)$$

$$B_{fp} = B_x H + B_y W - WH$$

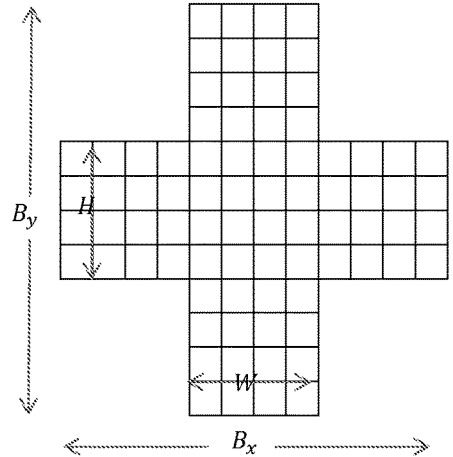

Figure A5a. "X" Shape Footprint

Table A5. Coefficients for "X" Shape Footprints

|  | 1 Storey | | 2 Stories | | 3+ Stories | |
|---|---|---|---|---|---|---|
|  | Rs < 0.45 | Rs >= 0.45 | Rs < 0.4 | Rs >= 0.4 | Rs < 0.4 | Rs >= 0.4 |
| $C_0$ | 0.6987 | 0.7517 | 0.6529 | 0.6805 | 0.5369 | 0.6608 |
| $C_1$ | -0.1259 | -0.1373 | -0.1643 | -0.1245 | 0.2045 | -0.1219 |
| $C_2$ | 0.4424 | 0.1826 | 0.4286 | 0.1347 | 0 | 0.1378 |
| $e_c$ | 0 | 0 | 0 | 0 | formula | formula |

For $N_s > 2$ and $R_s < 0.4$ $$e_c = 0.0015 \sqrt{\frac{B_{fp}}{N_s - 2}}$$

For $N_s > 2$ and $0.4 \leq R_s < 1.25$ $$e_c = 0.0012 \times R_s \sqrt{\frac{B_{fp}}{N_s - 2}} - 0.005 \sqrt{\frac{N_s - 2}{R_s}}$$

For $N_s > 2$ and $R_s \geq 1.25$ $$e_c = \frac{0.045}{R_s^{\,2}} \sqrt{\frac{N_s - 2}{B_{fp}}} + \left\{0.13 - 0.00018 \times R_s^{\,2}(N_s - 15)^2\right\}$$

6. Footprint T $$EUI_n = \sum_{i=0}^{3}\left(C_i \cdot R_s{}^i\right) + e_c + e_d$$

where $$R_s = \frac{B_e}{B_{fp}}$$

$$B_e = 2 \times \left(B_x + B_y\right)$$

$$B_{fp} = B_x \times (B_y - H) + WH$$

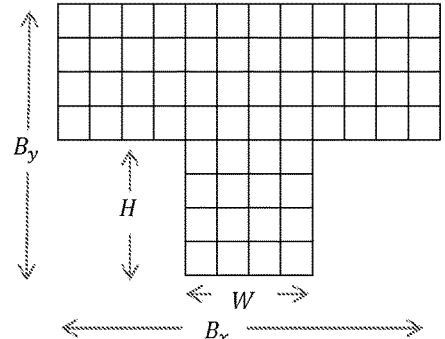

Figure A6a. "T" Shape Footprint

Table A6. Coefficients for "T" Shape Footprints

|  | 1 Storey | | 2 Stories | | 3+ Stories | |
|---|---|---|---|---|---|---|
|  | Rs < 0.4 | Rs >= 0.4 | Rs < 0.4 | Rs >= 0.4 | Rs < 0.4 | Rs >= 0.4 |
| $C_0$ | 0.7004 | 0.7922 | 0.6705 | 0.6782 | 0.5667 | 0.6750 |
| $C_1$ | -0.1452 | -0.3110 | -0.2653 | -0.1244 | 0.1200 | -0.1654 |
| $C_2$ | 0.4309 | 0.3461 | 0.5579 | 0.1301 | 0 | 0.1762 |
| $C_3$ | 0 | -0.0453 | 0 | 0 | 0 | 0 |
| $e_c$ | 0 | 0 | 0 | 0 | formula | formula |
| $e_d$ | 0 | 0 | 0 | 0 | 0 | formula |

For $N_s > 2$ and $R_s < 0.4$ $$e_c = 0.015\sqrt{\frac{1}{N_s - 2}}, \qquad e_d = 0$$

For $N_s > 2$ and $R_s \geq 0.4$ $$e_c = 0.03\sqrt{\frac{1}{N_s - 2}} - 0.0375$$

$$e_d = 0 \qquad \qquad \text{for } R_s < 1.25$$

$$e_d = 0.06\sqrt{R_s'}\left\{1 + \sin^2\left(\frac{\theta}{180}\pi\right) - 1.542\, R_s'\sqrt{\frac{N_s - 2}{B_{fp}}}\right\} \quad \text{for } R_s \geq 1.25$$

$R_s' = R_s - 1.25$, $\qquad \theta = $ building orientation degrees in clockwise

7. Footprint U
$$EUI_n = \sum_{i=0}^{2} \left(C_i \cdot R_s^{\,i}\right) + e_c$$
where
$$R_s = \frac{B_e}{B_{fp}}$$
$$B_e = 2 \times (B_x + B_y) + 2 \times (B_y - H)$$
$$B_{fp} = B_x \times B_y - (B_x - 2W) \times (B_y - H)$$
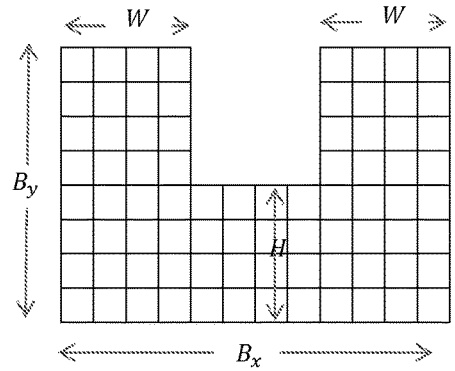
Figure A7a. "U" Shape Footprint
Table A7. Coefficients for "U" Shape Footprints
|       | 1 Storey | 2 Stories | 3+ Stories |
|-------|----------|-----------|------------|
| $C_0$ | 0.5052   | 0.4750    | 0.42786    |
| $C_1$ | 0.1121   | 0.1190    | 0.1385     |
| $C_2$ | 0.1231   | 0.0675    | 0.06788    |
| $e_c$ | 0        | 0         | formula    |
For $H > 1$ or $W > 1$
$$e_c = 0.002 \sqrt{\frac{B_{fp}}{N_s - 2}}$$

8. Footprint H
$$EUI_n = \sum_{i=0}^{3}\left(C_i \cdot R_s^{\,i}\right) + e_c$$
where
$$R_s = \frac{B_e}{B_{fp}}$$
$$B_e = 2 \times \left(B_x + B_y\right) + 2 \times \left(B_y - H\right)$$
$$B_{fp} = B_x \times B_y - (B_x - 2W) \times (B_y - H)$$
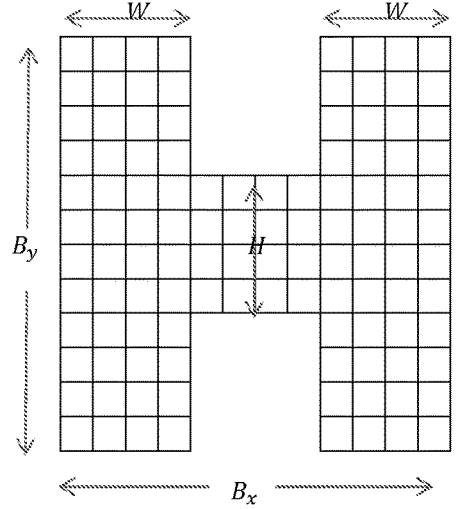
Figure A8a. "H" Shape Footprint
Table A8. Coefficients for "H" Shape Footprints
|       | 1 Storey | 2 Stories | 3+ Stories |
|-------|----------|-----------|------------|
| $C_0$ | 0.5952   | 0.4813    | 0.4421     |
| $C_1$ | -0.1785  | 0.1115    | 0.1092     |
| $C_2$ | 0.4032   | 0.0727    | 0.0876     |
| $C_3$ | -0.0731  | 0         | 0          |
| $e_c$ | 0        | 0         | formula    |
For $H > 1$ or $W > 1$
$$e_c = 0.0015\sqrt{\frac{B_{fp}}{N_s - 2}}$$

9. Footprint O $$EUI_n = \sum_{i=0}^{3}\{C_i \cdot (e_H + e_O)^i\} + e_c$$

where $$e_H = \{\,|H-2| + (H-2)\,\} + \{\,|W-2| + (W-2)\,\}$$

$$e_O = 5 \times \left(1 - \sqrt{H/W}\right) + \frac{4}{\sqrt[3]{V_x^2 V_y}}$$

$$V_x = B_x - 2W$$

$$V_y = B_y - 2H$$

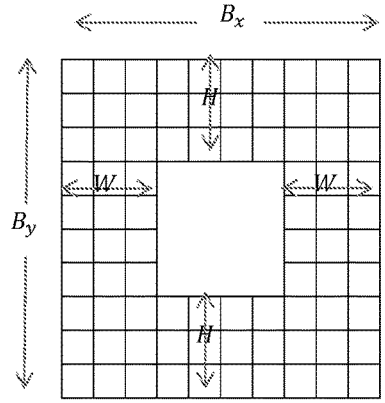

Figure A9a. "O" Shape Footprint

Table A9. Coefficients for "O" Shape Footprints

|       | 1 Storey   | 2 Stories | 3+ Stories |
|-------|------------|-----------|------------|
| $C_0$ | 0.6518     | 0.6950    | 0.6592     |
| $C_1$ | -0.0164    | -0.0122   | -0.01936   |
| $C_2$ | 0.00107    | 0.00037   | 0.001197   |
| $C_3$ | -2.480E-05 | 0         | -2.800E-05 |

For $N_s \leq 2$ $$e_C = \frac{N_s R_s}{B_{fp} + (B_x B_y - 36)}$$

For $N_s > 2$ $$e_C = \frac{0.6}{\sqrt{N_s - 2}} \left\{\frac{R_s}{B_{fp} + (B_x B_y - 36)} + \frac{0.1 B_{fp}}{B_x B_y}\right\} + e_d$$

$$e_d = 0.036\, R_s^2 \qquad \text{for } R_s > 0.75 \text{ and } H < 3$$

$$R_s = \frac{B_e}{B_{fp}}$$

$$B_{fp} = B_x B_y - (B_x - 2W) \times (B_y - 2H)$$

$$B_e = 2 \times (B_x + B_y) + 2 \times \{(B_x - 2W) + (B_y - 2H)\}$$

Alternate Formulas for the Buildings Higher than Two-Stories

Footprint R (Rectangle)

A. For $B_x \geq 4$ and $B_y \geq 4$ $$EUI_n = \left(\frac{1}{\sqrt{N_s - 2}} - 0.2\right) \times \frac{e_a - e_b}{0.8} + e_b$$

where $$\left. \begin{array}{l} e_a = \frac{1}{\sqrt{B_{fp}}} + 0.425 \\ \\ e_b = \frac{1.22}{\sqrt{B_{fp}}} + 0.371 \end{array} \right\} \quad if \ B_x > B_y$$

$$\left. \begin{array}{l} e_a = \frac{1.225}{\sqrt{B_{fp}}} + 0.395 \\ \\ e_b = \frac{1.52}{\sqrt{B_{fp}}} + 0.35 \end{array} \right\} \quad if \ B_x \leq B_y$$

$$B_{fp} = B_x B_y$$

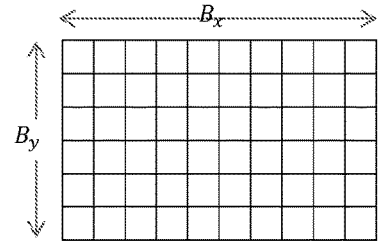

Footprint L
A. For $W \geq 2$ and $H \geq 2$
$$EUI_n = \left(\frac{1}{\sqrt{N_s - 2}} - 0.2\right) \times \frac{e_{a-}e_b}{0.8} + e_b + e_c$$
where
$e_a = 0.63$
$e_b = 0.6$
$e_c = \frac{3.0}{B_x B_y WH} + 0.2 \times (R_s - 0.905)$
$B_e = 2 \times (B_x + B_y)$
$B_{fp} = B_x H + B_y W - WH$
$R_s = \frac{B_e}{B_{fp}}$
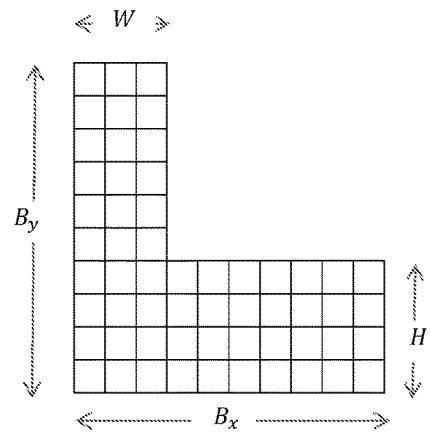
Footprint Z
A. For $B_{fp} \geq 16$ and $W \geq 2$ and $H \geq 2$
$$EUI_n = \left(\frac{1}{\sqrt{N_s - 2}} - 0.2\right) \times \frac{e_{a-}e_b}{0.8} + e_b + e_c$$
where
$e_a = 0.63$
$e_b = 0.605$
$e_c = \frac{3.0}{B_x B_y WH}$
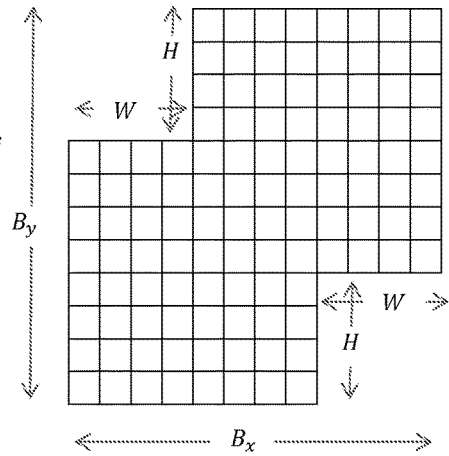

Footprint K
A. For $B_{fp} \geq 16$ and $W \geq 2$ and $H \geq 2$
$$EUI_n = \left(\frac{1}{\sqrt{N_s - 2}} - 0.2\right) \times \frac{e_a - e_b}{0.8} + e_b + e_c$$
where
$e_a = 0.63$
$e_b = 0.6$
$e_c = \dfrac{0.07}{(B_x - 2W) \times (B_y - 2H)} + \dfrac{3.6}{B_x B_y W H}$
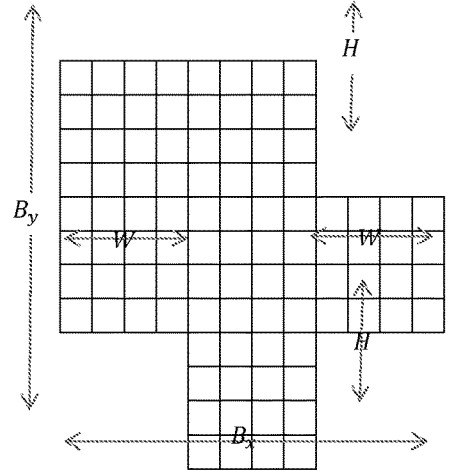
Footprint X
A. For $(H + W) \geq 4$
$$EUI_n = \left(\frac{1}{\sqrt{N_s - 2}} - 0.2\right) \times \frac{e_a - e_b}{0.8} + e_b + e_c$$
where
$e_a = 0.63$
$e_b = 0.6$
$e_c = \dfrac{3.0}{B_x B_y W H} + 0.06 \times \{(R_s - 0.6) + abs(R_s - 0.6)\}$
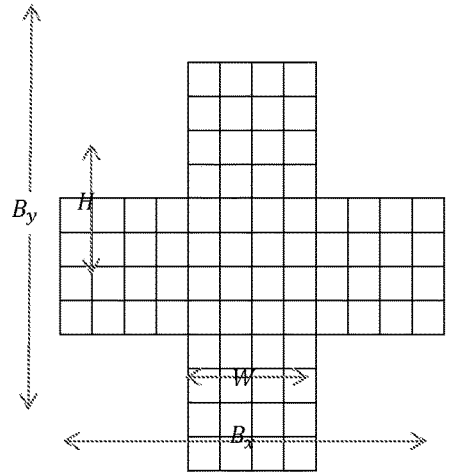

Footprint T

A. For $B_{fp} \geq 20$ $$EUI_n = \left(\frac{1}{\sqrt{N_s - 2}} - 0.2\right) \times \frac{e_a - e_b}{0.8} + e_b + e_c$$

where $e_a = 0.63$ $e_b = 0.6$ $e_c = \dfrac{3.0}{B_x B_y WH} + 0.1 \times \{(R_s - 0.75) + abs(R_s - 0.75)\}$ $B_e = 2 \times (B_x + B_y)$ $B_{fp} = B_x \times (B_y - H) + WH$ $R_s = \dfrac{B_e}{B_{fp}}$

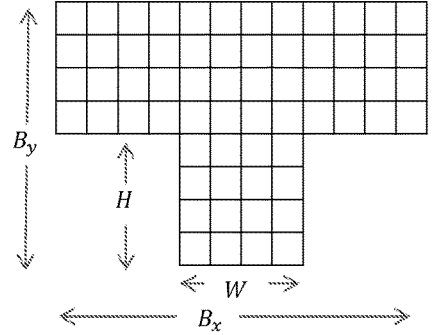

Footprint U

B. For $W \geq 2$ and $H \geq 2$ $$EUI_n = \left(\frac{1}{\sqrt{N_s - 2}} - 0.2\right) \times \frac{e_a - e_b}{0.8} + e_b + e_c$$

where $e_a = 0.63$ $e_b = 0.6$ $e_c = \dfrac{3.0}{B_x B_y WH} + 0.2 \times (R_s - 0.905)$ $B_e = 2 \times (B_x + B_y) + 2 \times (B_y - H)$ $B_{fp} = B_x \times B_y - (B_x - 2W) \times (B_y - H)$ $R_s = \dfrac{B_e}{B_{fp}}$

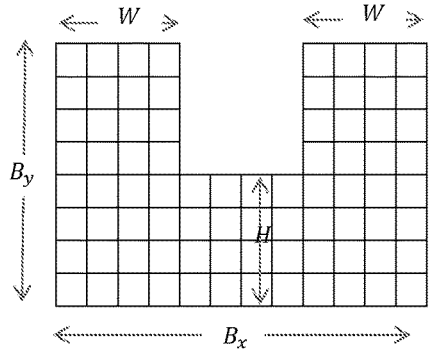

Footprint H
A. For $W \geq 2$ and $H \geq 2$
$$EUI_n = \left(\frac{1}{\sqrt{N_s - 2}} - 0.2\right) \times \frac{e_a - e_b}{0.8} + e_b + e_c$$
where
$e_a = 0.63$
$e_b = 0.6$
$e_c = \dfrac{3.0}{B_x B_y W H} + 0.2 \times (R_s - 0.95) + e_H$
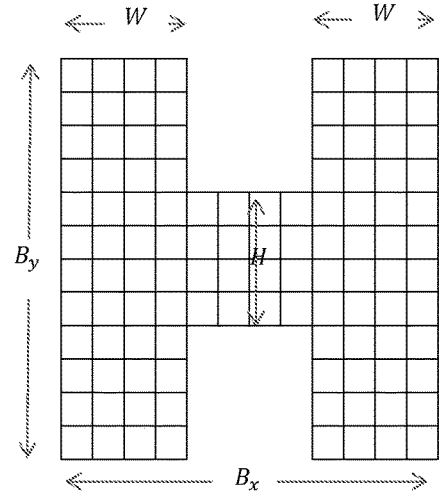
$B_e = 2 \times (B_x + B_y) + 2 \times (B_y - H)$
$B_{fp} = B_x \times B_y - (B_x - 2W) \times (B_y - H)$
$R_s = \dfrac{B_e}{B_{fp}}$
$e_H = 0.005 \times [\,\{\,|H - 3| + (H - 3)\,\} + \{\,|W - 3| + (W - 3)\,\}\,]$

Footprint O
A. *For $W \geq 2$ and $H \geq 2$*
$$EUI_n = \left(\frac{1}{\sqrt{N_s-2}} - 0.2\right) \times \frac{e_a - e_b}{0.8} + e_b + e_c$$
where
$e_a = 0.62$
$e_b = 0.593$
$e_c = \dfrac{3.0}{B_x B_y W H} + 0.2 \times (R_s - 0.75) + e_H + e_o$
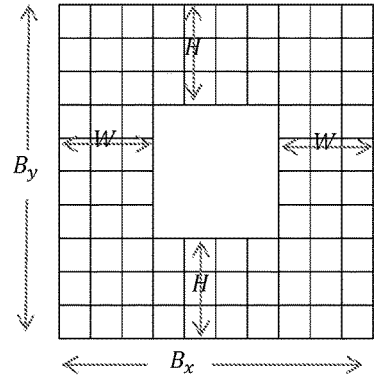
$B_e = 2(B_x + B_y) + 2(B_y - 2W) + 2(B_y - 2H)$
$B_{fp} = B_x \times B_y - (B_x - 2W) \times (B_y - 2H)$
$R_s = \dfrac{B_e}{B_{fp}}$
$e_H = 0.005 \times [\,\{\,|H-3| + (H-3)\,\} + \{\,|W-3| + (W-3)\,\}\,]$
$e_o = 0.025 \times \left(1 - \sqrt{H/W}\right) + \dfrac{0.02}{\sqrt[3]{V_x^2 V_y}}$
$V_x = B_x - 2W$
$V_y = B_y - 2H$

What is claimed is:

1. A computer based method for realizing a building system within which healthcare services will be provided, the method comprising:
    accessing types and volumes of healthcare services to be provided within the building system from memory of a computer system;
    accessing adjacency preferences between pairs of service types from memory of the computer system;
    matching, using the computer system, the accessed types and volumes of healthcare services to department blocks stored in a library of department blocks and to building massing configurations stored in a library of building massing configurations, the matching being performed as a function of the accessed adjacency preferences between pairs of service types;
    selecting, using the computer system, for display on a graphical user interface, an arrangement of department blocks within a building massing configuration that reflects a best match between the accessed types and volumes of healthcare services and the department blocks and the building massing configuration; and
    displaying the selected arrangement on the graphical user interface;
    wherein the matching comprises:
    defining, using the computer system, a set of department blocks to be placed within the building massing configuration;
    enumerating, using the computer system, sub-spaces within the building massing configuration;
    evaluating, using the computer system, multiple different department block arrangements within the enumerated sub-spaces by application of a genetic algorithm, wherein application of the genetic algorithm results in a fitness value for each of the multiple different department block arrangements;
    wherein the fitness value is a function of at least one cost parameter;
    wherein the at least one cost parameter is a constraint cost parameter that is representative of adjacency preferences of department blocks;
    wherein the adjacency preferences are represented by values that fall within a range of values, in which values at one end of the range are indicative of meeting an adjacency preference and values at the opposite end of the range are indicative of not meeting an adjacency preference.

2. The computer based method of claim 1, wherein the at least one cost parameter is a violation cost parameter that is representative of a violation of a specific block assignment.

3. The computer based method of claim 2, wherein the specific block assignment indicates that a particular department block is specifically assigned to a particular building or portion of the building and a violation occurs if the department block is not placed as assigned.

4. The computer based method of claim 2, wherein the specific block assignment indicates that a particular department block should be located entirely on the same floor and a violation occurs if subsets of the block are placed on different floors.

5. The computer based method of claim 1, wherein the at least one cost parameter is an overlap cost parameter that is representative of whether or not placed department blocks spatially overlap with each other on the same floor.

6. The computer based method of claim 5, wherein a high cost is registered if two department blocks are placed in a building system such that boundaries of the department blocks spatially overlap with each other.

7. The computer based method of claim 1, wherein the at least one cost parameter is an excess capacity cost parameter that is representative of whether or not a footprint area of placed blocks exceeds an available footprint area as defined by the building massing configuration.

8. The computer based method of claim 7, wherein a high cost is assigned to the excess capacity cost parameter when the footprint area of the placed department blocks exceeds the available footprint area.

9. The computer based method of claim 1, wherein the at least one cost parameter is an excess perimeter cost parameter that is representative of whether or not window perimeter needs of placed department blocks exceed available window perimeter of a corresponding floor.

10. The computer based method of claim 1, further comprising using spatial dimensions of the selected arrangement of department blocks in operational modeling to evaluate how the selected arrangement supports the accessed types and volumes of healthcare services to be provided within the building system.

11. The computer based method of claim 1, wherein the accessed types and volumes of healthcare services are matched to the department blocks for multiple different building massing configurations that are stored in the library of building massing configurations.

12. A computer based method for arranging department blocks in a building massing configuration of a building system within which healthcare services will be provided, the method comprising:
    accessing a set of department blocks to be placed within the building massing configuration from memory of a computer system, wherein the department blocks correspond to types and volumes of healthcare services to be provided within the building system and wherein the department blocks have spatial parameters;
    enumerating, using the computer system, sub-spaces within the building massing configuration;
    evaluating, using the computer system, multiple different department block arrangements within the enumerated sub-spaces by application of a genetic algorithm, wherein application of the genetic algorithm results in a fitness value for each of the multiple different department block arrangements;
    selecting using the computer system, for display on a graphical user interface, one of the multiple different department block arrangements based on its fitness value;
    wherein the fitness value is a function of at least one cost parameter;
    wherein the at least one cost parameter is a constraint cost parameter that is representative of adjacency preferences of department blocks;
    wherein the adjacency preferences are represented by values that fall within a range of values, in which values at one end of the range are indicative of meeting an adjacency preference and values at the opposite end of the range are indicative of not meeting an adjacency preference.

13. The computer based method of claim 12, wherein each department block is associated with a specific functional grouping, wherein the functional grouping relates to a function that is to be performed within the building system.

14. The computer based method of claim 12, wherein the at least one cost parameter is a violation cost parameter that is representative of a violation of a specific block assignment.

15. The computer based method of claim 14, wherein the specific block assignment indicates that a particular department block is specifically assigned to a particular building or portion of the building and a violation occurs if the department block is not placed as assigned.

16. The computer based method of claim 15, wherein the specific block assignment indicates that a particular department block should be located entirely on the same floor and a violation occurs if subsets of the block are placed on different floors.

17. The computer based method of claim 12, wherein the at least one cost parameter is an overlap cost parameter that is representative of whether or not placed department blocks spatially overlap with each other on the same floor.

18. The computer based method of claim 17, wherein a high cost is registered if two department blocks are placed in a building system such that boundaries of the department blocks spatially overlap with each other.

19. The computer based method of claim 12, wherein the at least one cost parameter is an excess capacity cost parameter that is representative of whether or not a footprint area of placed blocks exceeds an available footprint area as defined by the building massing configuration.

20. The computer based method of claim 19, wherein a high cost is assigned to the excess capacity cost parameter when the footprint area of the placed department blocks exceeds the available footprint area.

21. The computer based method of claim 12, wherein the at least one cost parameter is an excess perimeter cost parameter that is representative of whether or not window perimeter needs of placed department blocks exceed available window perimeter of a corresponding floor.

22. The computer based method of claim 12, wherein the fitness value is a function of multiple cost parameters including: a constraint cost parameter that is representative of adjacency preferences of department blocks; a violation cost parameter that is representative of a violation of a specific block assignment; an overlap cost parameter that is representative of whether or not placed department blocks spatially overlap with each other on the same floor; an excess capacity cost parameter that is representative of whether or not the footprint area of placed blocks exceeds the available footprint area as defined by the building massing configuration; and an excess perimeter cost parameter that is representative of whether or not window perimeter needs of placed department blocks exceed available window perimeter of a corresponding floor.

23. The computer based method of claim 12, further comprising using spatial dimensions of the selected department block arrangement in operational modeling to evaluate how the selected department block arrangement supports a pre-defined set of types and volumes of services to be provided within the building system.

24. A non-transitory computer readable medium that stores computer readable instructions, which when executed by at least one processor, implement a method for realizing a building system within which healthcare services will be provided, the method comprising:

accessing types and volumes of services to be provided within the building system from memory of a computer system;

accessing adjacency preferences between pairs of service types from memory of the computer system;

matching the accessed types and volumes of services to department blocks in a library of department blocks and to building massing configurations in a library of building massing configurations, the matching being performed as a function of the defined adjacency preferences between pairs of service types;

selecting, for display on a graphical user interface, an arrangement of department blocks within a building massing configuration that reflects a best match between the accessed types and volumes of services and the department blocks and building massing configuration; and displaying the selected arrangement on the graphical user interface;

wherein the matching comprises:

receiving a set of department blocks to be placed within the building massing configuration;

enumerating sub-spaces within the building massing configuration;

evaluating multiple different department block arrangements within the enumerated sub-spaces by application of a genetic algorithm, wherein application of the genetic algorithm results in a fitness value for each of the multiple different department block arrangements;

wherein the fitness value is a function of at least one cost parameter;

wherein the at least one cost parameter is a constraint cost parameter that is representative of adjacency preferences of department blocks;

wherein the adjacency preferences are represented by values that fall within a range of values, in which values at one end of the range are indicative of meeting an adjacency preference and values at the opposite end of the range are indicative of not meeting an adjacency preference.

25. A computer based method for realizing a building system within which healthcare services will be provided, the method comprising:

accessing types and volumes of healthcare services to be provided within the building system from memory of a computer system;

accessing adjacency preferences between pairs of service types from memory of the computer system;

matching, using the computer system, the accessed types and volumes of healthcare services to department blocks stored in a library of department blocks and to building massing configurations stored in a library of building massing configurations, the matching being performed as a function of the accessed adjacency preferences between pairs of service types;

selecting, using the computer system, for display on a graphical user interface, an arrangement of department blocks within a building massing configuration that reflects a best match between the accessed types and volumes of healthcare services and the department blocks and the building massing configuration; and displaying the selected arrangement on the graphical user interface;

wherein the matching comprises:

defining a set of department blocks to be placed within the building massing configuration;

enumerating sub-spaces within the building massing configuration;

evaluating multiple different department block arrangements within the enumerated sub-spaces by application of a genetic algorithm, wherein application of the genetic algorithm results in a fitness value for each of the multiple different department block arrangements;

wherein the fitness value is a function of at least one cost parameter;

wherein the at least one cost parameter is a violation cost parameter that is representative of a violation of a specific block assignment;

wherein the specific block assignment indicates that a particular department block is specifically assigned to a particular building or portion of the building and a violation occurs if the department block is not placed as assigned.

26. A computer based method for realizing a building system within which healthcare services will be provided, the method comprising:

accessing types and volumes of healthcare services to be provided within the building system from memory of a computer system;

accessing adjacency preferences between pairs of service types from memory of the computer system;

matching, using the computer system, the accessed types and volumes of healthcare services to department blocks stored in a library of department blocks and to building massing configurations stored in a library of building massing configurations, the matching being performed as a function of the accessed adjacency preferences between pairs of service types;

selecting, using the computer system, for display on a graphical user interface, an arrangement of department blocks within a building massing configuration that reflects a best match between the accessed types and volumes of healthcare services and the department blocks and the building massing configuration; and displaying the selected arrangement on the graphical user interface;

wherein the matching comprises:

defining a set of department blocks to be placed within the building massing configuration;

enumerating sub-spaces within the building massing configuration;

evaluating multiple different department block arrangements within the enumerated sub-spaces by application of a genetic algorithm, wherein application of the genetic algorithm results in a fitness value for each of the multiple different department block arrangements;

wherein the fitness value is a function of at least one cost parameter;

wherein the at least one cost parameter is a violation cost parameter that is representative of a violation of a specific block assignment;

wherein the specific block assignment indicates that a particular department block should be located entirely on the same floor and a violation occurs if subsets of the block are placed on different floors.

27. A computer based method for realizing a building system within which healthcare services will be provided, the method comprising:

accessing types and volumes of healthcare services to be provided within the building system from memory of a computer system;

accessing adjacency preferences between pairs of service types from memory of the computer system;

matching, using the computer system, the accessed types and volumes of healthcare services to department blocks stored in a library of department blocks and to building massing configurations stored in a library of building massing configurations, the matching being performed as a function of the accessed adjacency preferences between pairs of service types;

selecting, using the computer system, for display on a graphical user interface, an arrangement of department blocks within a building massing configuration that reflects a best match between the accessed types and volumes of healthcare services and the department blocks and the building massing configuration; and displaying the selected arrangement on the graphical user interface;

wherein the matching comprises:

defining a set of department blocks to be placed within the building massing configuration;

enumerating sub-spaces within the building massing configuration;

evaluating multiple different department block arrangements within the enumerated sub-spaces by application of a genetic algorithm, wherein application of the genetic algorithm results in a fitness value for each of the multiple different department block arrangements;

wherein the fitness value is a function of at least one cost parameter;

wherein the at least one cost parameter is an excess capacity cost parameter that is representative of whether or not a footprint area of placed blocks exceeds an available footprint area as defined by the building massing configuration.

28. A computer based method for realizing a building system within which healthcare services will be provided, the method comprising:

accessing types and volumes of healthcare services to be provided within the building system from memory of a computer system;

accessing adjacency preferences between pairs of service types from memory of the computer system;

matching, using the computer system, the accessed types and volumes of healthcare services to department blocks stored in a library of department blocks and to building massing configurations stored in a library of building massing configurations, the matching being performed as a function of the accessed adjacency preferences between pairs of service types;

selecting, using the computer system, for display on a graphical user interface, an arrangement of department blocks within a building massing configuration that reflects a best match between the accessed types and volumes of healthcare services and the department blocks and the building massing configuration; and displaying the selected arrangement on the graphical user interface;

wherein the matching comprises:

defining a set of department blocks to be placed within the building massing configuration;

enumerating sub-spaces within the building massing configuration;

evaluating multiple different department block arrangements within the enumerated sub-spaces by application of a genetic algorithm, wherein application of the genetic algorithm results in a fitness value for each of the multiple different department block arrangements;

wherein the fitness value is a function of at least one cost parameter;

wherein the at least one cost parameter is an excess perimeter cost parameter that is representative of whether or not window perimeter needs of placed department blocks exceed available window perimeter of a corresponding floor.

29. A computer based method for arranging department blocks in a building massing configuration of a building system within which healthcare services will be provided, the method comprising:
  accessing a set of department blocks to be placed within the building massing configuration from memory of a computer system, wherein the department blocks correspond to types and volumes of healthcare services to be provided within the building system and wherein the department blocks have spatial parameters;
  enumerating, using the computer system, sub-spaces within the building massing configuration;
  evaluating, using the computer system, multiple different department block arrangements within the enumerated sub-spaces by application of a genetic algorithm, wherein application of the genetic algorithm results in a fitness value for each of the multiple different department block arrangements;
  selecting, using the computer system, for display on a graphical user interface, one of the multiple different department block arrangements based on its fitness value;
  wherein the fitness value is a function of at least one cost parameter;
  wherein the at least one cost parameter is a violation cost parameter that is representative of a violation of a specific block assignment;
  wherein the specific block assignment indicates that a particular department block is specifically assigned to a particular building or portion of the building and a violation occurs if the department block is not placed as assigned.

30. A computer based method for arranging department blocks in a building massing configuration of a building system within which healthcare services will be provided, the method comprising:
  accessing a set of department blocks to be placed within the building massing configuration from memory of a computer system, wherein the department blocks correspond to types and volumes of healthcare services to be provided within the building system and wherein the department blocks have spatial parameters;
  enumerating, using the computer system, sub-spaces within the building massing configuration;
  evaluating, using the computer system, multiple different department block arrangements within the enumerated sub-spaces by application of a genetic algorithm, wherein application of the genetic algorithm results in a fitness value for each of the multiple different department block arrangements;
  selecting, using the computer system, for display on a graphical user interface, one of the multiple different department block arrangements based on its fitness value;
  wherein the fitness value is a function of at least one cost parameter;
  wherein the at least one cost parameter is an excess capacity cost parameter that is representative of whether or not a footprint area of placed blocks exceeds an available footprint area as defined by the building massing configuration.

31. A computer based method for arranging department blocks in a building massing configuration of a building system within which healthcare services will be provided, the method comprising:
  accessing a set of department blocks to be placed within the building massing configuration from memory of a computer system, wherein the department blocks correspond to types and volumes of healthcare services to be provided within the building system and wherein the department blocks have spatial parameters;
  enumerating, using the computer system, sub-spaces within the building massing configuration;
  evaluating, using the computer system, multiple different department block arrangements within the enumerated sub-spaces by application of a genetic algorithm, wherein application of the genetic algorithm results in a fitness value for each of the multiple different department block arrangements;
  selecting, using the computer system, for display on a graphical user interface, one of the multiple different department block arrangements based on its fitness value;
  wherein the fitness value is a function of at least one cost parameter;
  wherein the at least one cost parameter is an excess perimeter cost parameter that is representative of whether or not window perimeter needs of placed department blocks exceed available window perimeter of a corresponding floor.

* * * * *